(12) United States Patent
Altman

(10) Patent No.: US 10,774,143 B1
(45) Date of Patent: Sep. 15, 2020

(54) MODULATION OF T CELL SIGNALING VIA SLAT ASSOCIATION WITH IP3R1

(71) Applicant: LA JOLLA INSTITUTE FOR ALLERGY AND IMMUNOLOGY, La Jolla, CA (US)

(72) Inventor: Amnon Altman, La Jolla, CA (US)

(73) Assignee: LA JOLLA INSTITUTE FOR ALLERGY AND IMMUNOLOGY, La Jolla, CA (US)

( * ) Notice: Subject to any disclaimer, the term of this patent is extended or adjusted under 35 U.S.C. 154(b) by 193 days.

(21) Appl. No.: 14/702,059

(22) Filed: May 1, 2015

Related U.S. Application Data

(60) Provisional application No. 61/988,028, filed on May 2, 2014.

(51) Int. Cl.
| | | |
|---|---|---|
| *C07K 16/18* | (2006.01) | |
| *C07K 16/28* | (2006.01) | |
| *C07K 14/205* | (2006.01) | |
| *A61K 38/00* | (2006.01) | |
| *A61K 38/17* | (2006.01) | |
| *C07K 14/705* | (2006.01) | |

(52) U.S. Cl.
CPC ............... *C07K 16/28* (2013.01); *A61K 38/00* (2013.01); *A61K 38/17* (2013.01); *A61K 38/177* (2013.01); *C07K 14/705* (2013.01); *C07K 16/18* (2013.01); *A61K 2300/00* (2013.01); *C07K 2317/34* (2013.01); *C07K 2317/76* (2013.01)

(58) Field of Classification Search
CPC ........ A61K 38/00; A61K 38/17; A61K 37/17; A61K 2300/00; C07K 14/705; C07K 16/28; C07K 16/40; C07K 2317/34; C07K 2317/76
See application file for complete search history.

(56) References Cited

U.S. PATENT DOCUMENTS

| | | | | |
|---|---|---|---|---|
| 7,041,440 | B2 * | 5/2006 | Mikoshiba | C07K 14/705 435/4 |
| 2003/0096780 | A1 * | 5/2003 | Mikoshiba | C07K 14/705 514/44 R |
| 2009/0048168 | A1 * | 2/2009 | Distelhorst | C07K 14/705 514/1.1 |

OTHER PUBLICATIONS

Millet, F. Cell-penetrating peptides: classes, origin, and currently landscape. Drug Discovery Today, 2012, vol. 17, No. 15/16, p. 850-860.*
Feske, S. Calcium signalling in lymphocyte activation and disease. Nature Reviews Immunology, 2007, vol. 7, p. 690-702.*
Chamarthy, S.P., et al., Gene delivery to dendritic cells facilitated by a tumor necrosis factor alpha-competing peptide, Molecular Immunology, 2004, 41:741-749.
Dinauer, N., et al., Selective targeting of antibody-conjugated nanoparticles to leukemic cells and primary T-lymphocytes, Biomaterials, 2005, 26:5898-5906.
Gray, B.P., et al., Combinatorial Peptide Libraries: Mining for Cell-Binding Peptides, Chem. Rev. 2014, 114:1020-1081.

* cited by examiner

*Primary Examiner* — Joanne Hama
*Assistant Examiner* — Bruce D. Hissong
(74) *Attorney, Agent, or Firm* — Pillsbury Winthrop Shaw Pittman LLP

(57) ABSTRACT

Methods of modulating immune responses are provided, including contacting SLAT or IP3R1 with an agent that modulates binding of SLAT to IP3R1. Methods of modulating activation or differentiation of CD4+ T cells are also provided, including contacting SLAT or IP3R1 with an agent that modulates binding of SLAT to IP3R1. Peptides and fragments of an IP3R1 amino acid sequence that binds to a SLAT amino acid sequence, and peptides and fragments of a SLAT amino acid sequence that binds to am IP3R1 amino acid sequence, are further provided.

11 Claims, 20 Drawing Sheets

Specification includes a Sequence Listing.

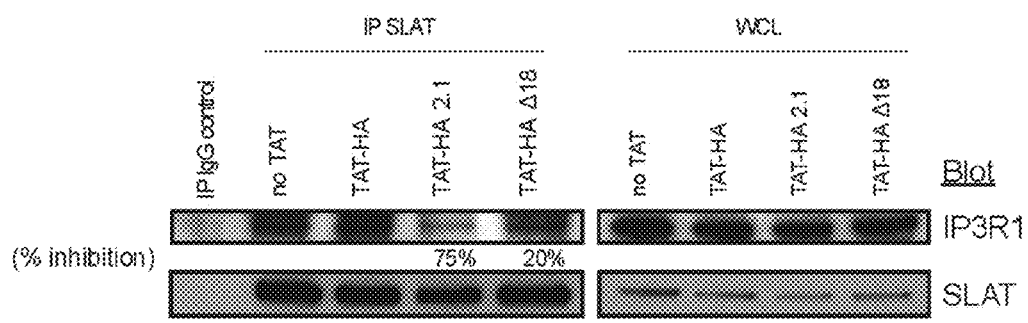
FIG. 6A
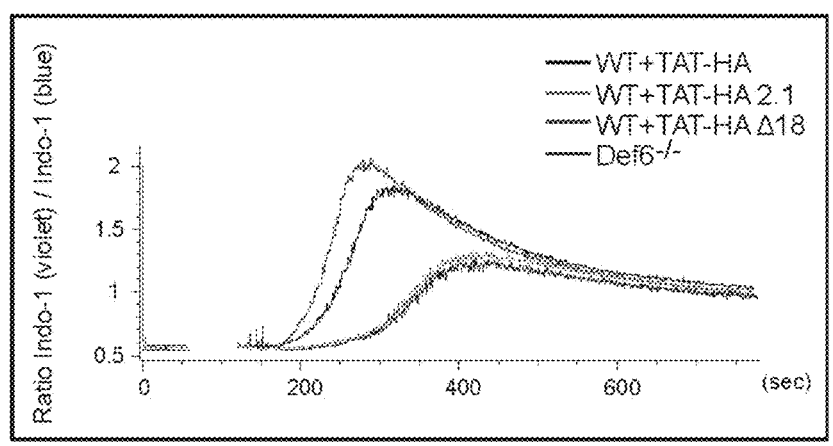
FIG. 6B
FIG. 6C

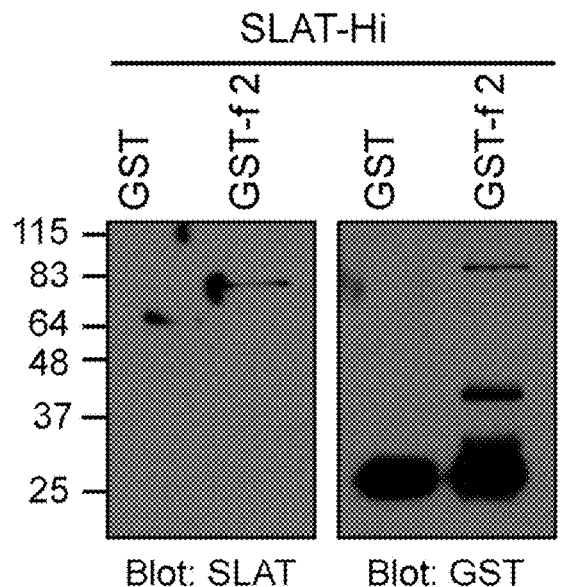

The SLAT-IP3R1 interaction is direct. Far-western blots were performed as described[1]. Recombinant proteins corresponding to the GST or GST-IP3R1-f2 were resolved by SDS-PAGE and transferred to nitrocellulose membranes. Proteins were denatured, renatured, and incubated with purified His-SLAT recombinant protein. After washing, bound proteins were detected by anti-SLAT, followed by anti-GST Ab immunoblotting.

1. Wu, Y., Q. Li, et al. (2007). "Detecting protein-protein interactions by Far western blotting." Nat Protoc 2(12): 3278-3284.

FIG. 7

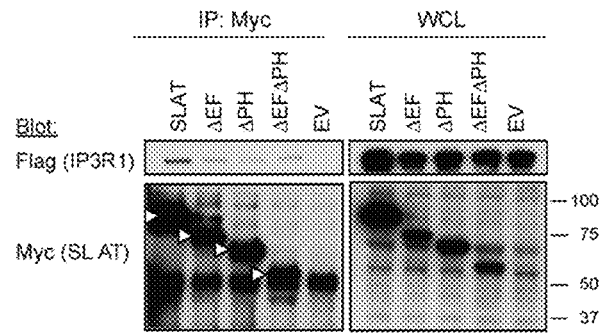

FIG. 8A

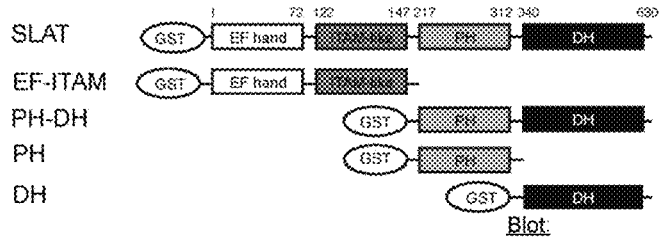

FIG. 8B

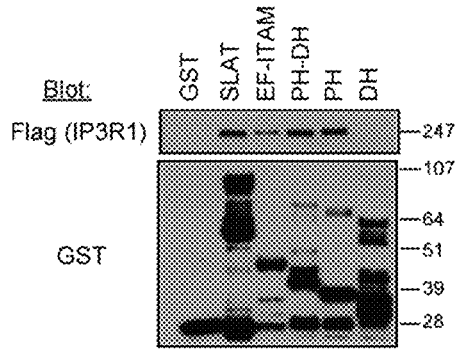

FIG. 8C

The EF and PH domains of SLAT bind IP3R1.
(a) Immunoblots of anti-Myc SLAT IPs (*IP: Myc*; left panels) or whole cell lysates (*WCL*; right panels). HEK-293T cells cotransfected with the indicated Myc-tagged SLAT (or empty; EV) vectors plus Flag-tagged IP3R1. Arrowheads indicate the position of the Myc-SLAT proteins. (b) Schematic representation of GST-SLAT recombinant proteins. (c) Cell lysates from HEK-293T overexpressing Flag-tagged IP3R1 were precleared and incubated with gluthatione-bound GST fusion proteins for 1 h at 4°C. Eluted proteins were subjected to SDS-PAGE and immunoblotted with the indicated antibodies. Data shown are representative of 2 experiments.

| | | | |
|---|---|---|---|
| M.musculus IP3R1 | (400-417) | NP_034715 IP3R1 | HSTNIPIDKEEEKPVM--MLK (SEQ ID NO:4) |
| M.musculus IP3R2 | (399-416) | NP_064307 IP3R2 | TSTTIPIDTEEERPV--MLK (SEQ ID NO:17) |
| M.musculus IP3R3 | (399-416) | NP_542120 IP3R3 | QSTNAPIDVEEERPRLMLG (SEQ ID NO:18) |
| H.sapiens | (400-417) | Q14643 | HSTNIPIDKEEEKPVMLK (SEQ ID NO:19) |
| C.lupus | (385-402) | XP_005632286 | HSTNIPIDKEEEKPVMLK (SEQ ID NO:20) |
| R.norvegicus | (400-417) | NP_001007236 | HSTNIPIDKEEEKPVMLK (SEQ ID NO:21) |
| C.porcellus | (386-403) | XP_003473502 | HSTNIPIDKEEEKPVMLK (SEQ ID NO:22) |
| Orcinus orca | (385-402) | XP_004274825 | HSTNIPIDKEEEKPVMLK (SEQ ID NO:23) |
| G.gallus | (400-417) | NP_001167530 | HSTNIPIDKEEEKPVMLK (SEQ ID NO:24) |
| D.rerio | (410-427) | XP_005172967 | HSTNIPIDKEEEKPVMLK (SEQ ID NO:25) |

Alignment of the 18-amino acid IP3R1 motif critical for the interaction with SLAT in mouse IP3R1, IP3R2 and IP3R3 (top), and IP3R1 proteins from the indicated organisms (bottom). Motifs were aligned using the T-Coffee program, and residues were shaded according to % of similarity using the Boxshade software. Black shading indicates amino acid identity.

FIG. 9

Intact IP3R1 expression in Def6 /- T cells. IP3R1 mRNA and protein expression were analyzed by RT-qPCR (a) and immunoblotting (b), respectively. Equal amounts of protein were resolved by SDS-PAGE and immunoblotted with the indicated Abs. Data shown are representative of 3 experiments.

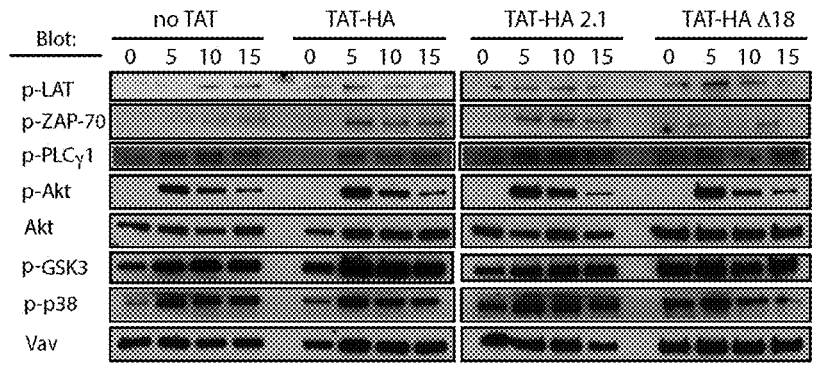

FIG. 11A

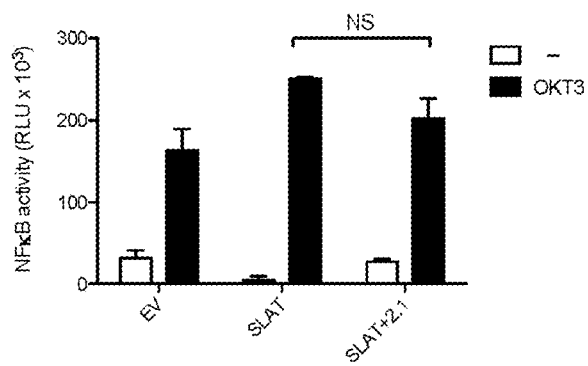

FIG. 11B

(a) B6 CD4+ T cells were pre-incubated with TAT fusion proteins and stimulated as in Fig. 6e for the indicated times (min). Equal protein amounts were resolved by SDS-PAGE and immunoblotted with the indicated Abs. Data shown are representative of 2 experiments. (b) TAT fusion peptide transduction does not alter proximal TCR signaling. Jurkat (JA16) T cells were cotransfected with empty vector (EV), or with Myc-tagged SLAT in the absence or presence of a pEF vector expressing TAT-HA 2.1, together with NF-κB-Luc and β-Gal reporter plasmids. Cells were stimulated or not, and normalized Luc activity was determined as in Fig. 6f. Data shown are representative of 3 experiments.

SEQUENCE LISTING

```
<160> NUMBER OF SEQ ID NOS: 25

<210> SEQ ID NO 1
<211> LENGTH: 72
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Met Ala Leu Arg Lys Glu Leu Leu Lys Ser Ile Trp Tyr Ala Phe Thr
1               5                   10                  15

Ala Leu Asp Val Glu Lys Ser Gly Lys Val Ser Lys Ser Gln Leu Lys
            20                  25                  30

Val Leu Ser His Asn Leu Tyr Thr Val Leu His Ile Pro His Asp Pro
        35                  40                  45

Val Ala Leu Glu Glu His Phe Arg Asp Asp Asp Gly Pro Val Ser
    50                  55                  60

Ser Gln Gly Tyr Met Pro Tyr Leu
65                  70

<210> SEQ ID NO 2
<211> LENGTH: 96
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Val Leu Lys Gln Gly Tyr Leu Trp Lys Arg Gly His Leu Arg Arg Asn
1               5                   10                  15

Trp Ala Glu Arg Trp Phe Gln Leu Gln Pro Ser Cys Leu Cys Tyr Phe
            20                  25                  30
```

```
Gly Ser Glu Glu Cys Lys Glu Lys Arg Gly Ile Ile Pro Leu Asp Ala
            35                  40                  45

His Cys Cys Val Glu Val Leu Pro Asp Arg Asp Gly Lys Arg Cys Met
 50                  55                  60

Phe Cys Val Lys Thr Ala Asn Arg Thr Tyr Glu Met Ser Ala Ser Asp
 65                  70                  75                  80

Thr Arg Gln Arg Gln Glu Trp Thr Ala Ala Ile Gln Met Ala Ile Arg
                85                  90                  95

<210> SEQ ID NO 3
<211> LENGTH: 145
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Asn Ala Gln Glu Lys Met Val Tyr Ser Leu Val Ser Val Pro Glu Gly
 1               5                  10                  15

Asn Asp Ile Ser Ser Ile Phe Glu Leu Asp Pro Thr Thr Leu Arg Gly
                20                  25                  30

Gly Asp Ser Leu Val Pro Arg Asn Ser Tyr Val Arg Leu Arg His Leu
            35                  40                  45

Cys Thr Asn Thr Trp Val His Ser Thr Asn Ile Pro Ile Asp Lys Glu
 50                  55                  60

Glu Glu Lys Pro Val Met Leu Lys Ile Gly Thr Ser Pro Val Lys Glu
 65                  70                  75                  80

Asp Lys Glu Ala Phe Ala Ile Val Pro Val Ser Pro Ala Glu Val Arg
                85                  90                  95

Asp Leu Asp Phe Ala Asn Asp Ala Ser Lys Val Leu Gly Ser Ile Ala
            100                 105                 110

Gly Lys Leu Glu Lys Gly Thr Ile Thr Gln Asn Glu Arg Arg Ser Val
            115                 120                 125

Thr Lys Leu Leu Glu Asp Leu Val Tyr Phe Val Thr Gly Gly Thr Asn
        130                 135                 140

Ser
145

<210> SEQ ID NO 4
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

His Ser Thr Asn Ile Pro Ile Asp Lys Glu Glu Glu Lys Pro Val Met
 1               5                  10                  15

Leu Lys

<210> SEQ ID NO 5
<211> LENGTH: 16
<212> TYPE: PRT
<213> ORGANISM: Artificial Sequence
<220> FEATURE:
<223> OTHER INFORMATION: Description of Artificial Sequence: Cell-
      penetrating moiety
```

```
<400> SEQUENCE: 5

Arg Gln Ile Lys Ile Trp Phe Gln Asn Arg Arg Met Lys Trp Lys Lys
1               5                   10                  15

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Cell-
      penetrating moiety

<400> SEQUENCE: 6

Arg Arg Arg Arg Arg Arg Arg Arg Arg
1               5

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Cell-
      penetrating moiety

<400> SEQUENCE: 7

Lys Lys Lys Lys Lys Lys Lys Lys Lys
1               5

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: Cell-
      penetrating moiety

<400> SEQUENCE: 8

Arg Arg Gln Arg Arg Thr Ser Lys Leu Met Lys Arg
1               5                   10

<210> SEQ ID NO 9
<211> LENGTH: 27
<212> TYPE: PRT
<213> ORGANISM: Artificial Sequence
<220> FEATURE:
<223> OTHER INFORMATION: Description of Artificial Sequence: Cell-
      penetrating moiety

<400> SEQUENCE: 9

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 10
<211> LENGTH: 30
<212> TYPE: PRT
<213> ORGANISM: Artificial Sequence
<220> FEATURE:
<223> OTHER INFORMATION: Description of Artificial Sequence: Cell-
      penetrating moiety
```

```
<400> SEQUENCE: 10

Trp Glu Ala Lys Leu Ala Lys Ala Leu Ala Lys Ala Leu Ala Lys His
1               5                   10                  15

Leu Ala Lys Ala Leu Ala Lys Ala Leu Lys Ala Cys Glu Ala
            20                  25                  30

<210> SEQ ID NO 11
<211> LENGTH: 76
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Met Ala Leu Arg Lys Glu Leu Leu Lys Ser Ile Trp Tyr Ala Phe Thr
1               5                   10                  15

Ala Leu Asp Val Glu Lys Ser Gly Lys Val Ser Lys Ser Gln Leu Lys
            20                  25                  30

Val Leu Ser His Asn Leu Tyr Thr Val Leu Asn Ile Pro His Pro Val
        35                  40                  45

Ala Leu Glu Glu His Phe Arg Asp Asp Asp Gly Pro Val Ser Ser
    50                  55                  60

Gln Gly Tyr Met Pro Tyr Leu Asn Lys Tyr Ile Leu
65                  70                  75

<210> SEQ ID NO 12
<211> LENGTH: 64
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Met Ala Leu Arg Lys Glu Leu Leu Lys Ser Ile Trp Tyr Ala Phe Thr
1               5                   10                  15

Ala Leu Leu Lys Val Leu Ser His Asn Leu Tyr Thr Val Leu Asn Ile
            20                  25                  30

Pro His Pro Val Ala Leu Glu Glu His Phe Arg Asp Asp Asp Asp Gly
        35                  40                  45

Pro Val Ser Ser Gln Gly Tyr Met Pro Tyr Leu Asn Lys Tyr Ile Leu
    50                  55                  60

<210> SEQ ID NO 13
<211> LENGTH: 64
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Met Ala Leu Arg Lys Glu Leu Leu Lys Ser Ile Trp Tyr Ala Phe Thr
1               5                   10                  15

Ala Leu Leu Lys Val Leu Ser His Asn Leu Tyr Thr Val Leu Asn Ile
            20                  25                  30

Pro His Pro Val Ala Leu Glu Glu His Phe Arg Asp Asp Asp Asp Gly
        35                  40                  45

Pro Val Ser Ser Gln Gly Tyr Met Pro Tyr Leu Asn Lys Tyr Ile Leu
    50                  55                  60
```

```
<210> SEQ ID NO 14
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide TAT-HA

<400> SEQUENCE: 14

Tyr Gly Arg Lys Lys Arg Arg Gln Arg Arg Tyr Pro Tyr Asp Val
1               5                   10                  15

Pro Asp Tyr Ala
            20

<210> SEQ ID NO 15
<211> LENGTH: 165
<212> TYPE: PRT
<213> ORGANISM: Artificial Sequence
<220> FEATURE:
<223> OTHER INFORMATION: Description of Artificial Sequence: Synthetic
      peptide TAT-HA 2.1

<400> SEQUENCE: 15

Tyr Gly Arg Lys Lys Arg Arg Gln Arg Arg Tyr Pro Tyr Asp Val
1               5                   10                  15

Pro Asp Tyr Ala Asn Ala Gln Glu Lys Met Val Tyr Ser Leu Val Ser
                20                  25                  30

Val Pro Glu Gly Asn Asp Ile Ser Ser Ile Phe Glu Leu Asp Pro Thr
            35                  40                  45

Thr Leu Arg Gly Gly Asp Ser Leu Val Pro Arg Asn Ser Tyr Val Arg
50                  55                  60

Leu Arg His Leu Cys Thr Asn Thr Trp Val His Ser Thr Asn Ile Pro
65                  70                  75                  80

Ile Asp Lys Glu Glu Glu Lys Pro Val Met Leu Lys Ile Gly Thr Ser
                85                  90                  95

Pro Val Lys Glu Asp Lys Glu Ala Phe Ala Ile Val Pro Val Ser Pro
            100                 105                 110

Ala Glu Val Arg Asp Leu Asp Phe Ala Asn Asp Ala Ser Lys Val Leu
        115                 120                 125

Gly Ser Ile Ala Gly Lys Leu Glu Lys Gly Thr Ile Thr Gln Asn Glu
    130                 135                 140

Arg Arg Ser Val Thr Lys Leu Leu Glu Asp Leu Val Tyr Phe Val Thr
145                 150                 155                 160

Gly Gly Thr Asn Ser
                165

<210> SEQ ID NO 16
<211> LENGTH: 183
<212> TYPE: PRT
<213> ORGANISM: Artificial Sequence
<220> FEATURE:
<223> OTHER INFORMATION: Description of Artificial Sequence: Synthetic
      peptide TAT-HA Delta 18

<400> SEQUENCE: 16

Tyr Gly Arg Lys Lys Arg Arg Gln Arg Arg Tyr Pro Tyr Asp Val
1               5                   10                  15

Pro Asp Tyr Ala Asn Ala Gln Glu Lys Met Val Tyr Ser Leu Val Ser
                20                  25                  30

Val Pro Glu Gly Asn Asp Ile Ser Ser Ile Phe Glu Leu Asp Pro Thr
            35                  40                  45
```

```
Thr Leu Arg Gly Gly Asp Ser Leu Val Pro Arg Asn Ser Tyr Val Arg
 50                  55                  60
Leu Arg His Leu Cys Thr Asn Thr Trp Val His Ser Thr Asn Ile Pro
 65                  70                  75                  80
Ile Asp Lys Glu Glu Lys Pro Val Met Leu Lys Ile Gly Thr Ser
                 85                  90                  95
Pro Val Lys Glu Asp Lys Glu Ala Phe Ala Ile Val Pro Val Ser Pro
                100                 105                 110
Ala Glu Val Arg Asp Leu Asp Phe Ala Asn Asp Ala Ser Lys Val Leu
                115                 120                 125
Gly Ser Ile Ala Gly Lys Leu Glu Lys Gly Thr Ile Thr Gln Asn Glu
130                 135                 140
Arg Arg Ser Val Thr Lys Leu Leu Glu Asp Leu Val Tyr Phe Val Thr
145                 150                 155                 160
Gly Gly Thr Asn Ser His Ser Thr Asn Ile Pro Ile Asp Lys Glu Glu
                165                 170                 175
Glu Lys Pro Val Met Leu Lys
            180
```

<210> SEQ ID NO 17
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

```
Thr Ser Thr Thr Ile Pro Ile Asp Thr Glu Glu Glu Arg Pro Val Met
 1               5                  10                  15
Leu Lys
```

<210> SEQ ID NO 18
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

```
Gln Ser Thr Asn Ala Pro Ile Asp Val Glu Glu Glu Arg Pro Ile Arg
 1               5                  10                  15
Leu Met Leu Gly
            20
```

<210> SEQ ID NO 19
<211> LENGTH: 18
<212> TYPE: PRT
<213> ORGANISM: Homo sapiens

<400> SEQUENCE: 19

```
His Ser Thr Asn Ile Pro Ile Asp Lys Glu Glu Glu Lys Pro Val Met
 1               5                  10                  15
Leu Lys
```

<210> SEQ ID NO 20
<211> LENGTH: 18
<212> TYPE: PRT
<213> ORGANISM: Canis lupus

```
<400> SEQUENCE: 20

His Ser Thr Asn Ile Pro Ile Asp Lys Glu Glu Glu Lys Pro Val Met
1               5                   10                  15

Leu Lys

<210> SEQ ID NO 21
<211> LENGTH: 18
<212> TYPE: PRT
<213> ORGANISM: Rattus norvegicus

<400> SEQUENCE: 21

His Ser Thr Asn Ile Pro Ile Asp Lys Glu Glu Glu Lys Pro Val Met
1               5                   10                  15

Leu Lys

<210> SEQ ID NO 22
<211> LENGTH: 18
<212> TYPE: PRT
<213> ORGANISM: Cavia porcellus

<400> SEQUENCE: 22

His Ser Thr Asn Ile Pro Ile Asp Lys Glu Glu Glu Lys Pro Val Met
1               5                   10                  15

Leu Lys

<210> SEQ ID NO 23
<211> LENGTH: 18
<212> TYPE: PRT
<213> ORGANISM: Orcinus orca

<400> SEQUENCE: 23

His Ser Thr Asn Ile Pro Ile Asp Lys Glu Glu Glu Lys Pro Val Met
1               5                   10                  15

Leu Lys

<210> SEQ ID NO 24
<211> LENGTH: 18
<212> TYPE: PRT
<213> ORGANISM: Gallus gallus

<400> SEQUENCE: 24

His Ser Thr Asn Ile Pro Ile Asp Lys Glu Glu Glu Lys Pro Val Met
1               5                   10                  15

Leu Lys

<210> SEQ ID NO 25
<211> LENGTH: 18
<212> TYPE: PRT
<213> ORGANISM: Danio rerio

<400> SEQUENCE: 25

His Ser Thr Asn Ile Pro Ile Asp Lys Glu Glu Glu Lys Pro Val Met
1               5                   10                  15

Leu Lys
```

MODULATION OF T CELL SIGNALING VIA SLAT ASSOCIATION WITH IP3R1

RELATED APPLICATION INFORMATION

This application claims priority to U.S. Provisional Application No. 61/988,028, filed May 2, 2014, which application is expressly incorporated herein by reference in its entirety.

GOVERNMENT SUPPORT

This invention was made with government support under grant R01AI068320 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Jul. 14, 2015, is named liai0438918_ST25.txt and is 5,566 bytes in size.

INTRODUCTION

The modulation of intracellular $Ca^{2+}$ concentration ($[Ca^{2+}]i$) is a common signaling mechanism shared by many biological systems and cells. $Ca^{2+}$ signaling plays a crucial role in immune responses by regulating many aspects of lymphocyte biology including development, activation and effector functions (1). Impaired $Ca^{2+}$ signaling in T lymphocytes has been linked to pathophysiological processes in several autoimmune and inflammatory diseases (2).

Antigen recognition through the T-cell receptor (TCR) results in the activation and recruitment of protein tyrosine kinases such as Lck and Zap-70 (ζ-chain-associated protein kinase of 70 kDa) to the TCR-associated CD3 chains, which in turn leads to the phosphorylation of enzymes and adaptor proteins. Activating phosphorylation of phospholipase-Cγ1 (PLCγ1) and its recruitment to the plasma membrane (PM) leads to the hydrolysis of phosphatidylinositol 4,5-bisphosphate (PIP2), generating inositol 1,4,5-triphosphate (IP3) and diacylglycerol second messengers. IP3 triggers $Ca^{2+}$ release from intracellular stores through binding to, and opening of inositol triphosphate receptors (IP3Rs) in the endoplasmic reticulum (ER). ER $Ca^{2+}$ store depletion leads to the activation of calcium release-activated calcium (CRAC) channels at the plasma membrane (PM) and results in a sustained cellular $Ca^{2+}$ influx. Elevated $[Ca^{2+}]i$ results in the activation of $Ca^{2+}$-dependent enzymes, including calcineurin, which dephosphorylates, and induces subsequent nuclear translocation of, nuclear factor of activated T cells (NFAT), a transcription factor that controls multiple target genes involved in T cell activation and differentiation.

Functional IP3Rs are large tetrameric proteins that reside primarily in the ER although their localization has also been reported in the Golgi and at the PM (3, 4). Each monomer harbors an N-terminal IP3 ligand-binding domain (LBD) followed by a large coupling domain and a C-terminal domain that contains the channel region (5). Lymphocytes express the three IP3R isoforms (1) referred to as IP3R type I (IP3R1), IP3R type II (IP3R2), and IP3R type III (IP3R3). IP3R regulation is complex and involves many mechanisms including IP3 and $Ca^{2+}$ binding (5), but also post-translational modifications such as tyrosine phosphorylation (6) and protein-protein interactions. Many proteins have been reported to interact with IP3Rs and to modulate their affinity and/or conductivity as well as their localization and cellular distribution (3, 7-9).

SWAP-70-like adaptor of T cells (SLAT) (10), also known as Def6 (11) or IBP (12), is a guanine nucleotide exchange factor (GEF) for Rho GTPases and is predominantly expressed in thymocytes and peripheral T cells (10, 12, 13). Structurally, SLAT harbors, beginning at its N-terminus, a putative $Ca^{2+}$-binding EF-hand domain, followed by an imperfect ITAM-like sequence, a PIP3-binding pleckstrin-homology (PH) domain (10), and a catalytic Dbl-homology (DH) domain exhibiting GEF activity towards Cdc42 and Rac1 (14-16). Phosphorylation of the ITAM-like sequence following T cell stimulation localizes SLAT at the PM and the T cell immunological synapse (IS), a prerequisite for its effector activity (16). SLAT regulates the activation and differentiation of CD4+ T cells by controlling $Ca^{2+}$ release from ER stores in response to TCR/CD28 costimulation (13). Hence, SLAT-deficient (Def6−/−) T cells display a severe defect in $Ca^{2+}$ signaling and NFAT activation, despite normal PLCγ1 activation and intact IP3 production (13). However, the molecular mechanism underlying this defect has not been identified.

SUMMARY

A direct, TCR-induced and $Ca^{2+}$-sensitive association between SLAT and the IP3R1 has been discovered and characterized herein. Both the N-terminal EF-hand domain and the PH domain of SLAT interacted with IP3R1 and were important for SLAT-mediated $Ca^{2+}$ regulation. It was further demonstrated that a short motif within the LBD of IP3R1 binds SLAT. The biological relevance of this association was established by demonstrating that its disruption in CD4+ T cells impaired TCR-induced $Ca^{2+}$/NFAT signaling and cytokine production. Thus, SLAT is an IP3R1-interacting protein that regulates the TCR-mediated $Ca^{2+}$/NFAT signaling pathway.

Thus, in one embodiment, there is provided a method of modulating an immune response, comprising contacting SLAT or IP3R1 with an agent that modulates binding of SLAT to IP3R1, thereby modulating an immune response. In another embodiment, there is provided a method of modulating activation or differentiation of CD4+ T cells, comprising contacting SLAT or IP3R1 with an agent that modulates binding of SLAT to IP3R1, thereby modulating activation or differentiation of CD4+ T cells. In another embodiment, the invention provides for use of an agent for modulating binding of SLAT to IP3R1, to modulate an immune response. In another embodiment, the invention provides for use of an agent for modulating binding of SLAT to IP3R1, to modulate activation or differentiation of CD4+ T cells. In another embodiment, the invention provides for use of an agent in the manufacture of a medicament for modulating binding of SLAT to IP3R1, thereby modulating an immune response. In another embodiment, the invention provides for use of an agent in the manufacture of a medicament for modulating binding of SLAT to IP3R1, thereby modulating activation or differentiation of CD4+ T cells. In another embodiment, the invention provides for use of an agent for modulating binding of SLAT to IP3R1 in the manufacture of a medicament for modulating an immune response. In another embodiment, the invention provides for use of an agent for modulating binding of SLAT to IP3R1 in the manufacture of a medicament for modulating activation or differentiation of CD4+ T cells. In particular aspects the method comprises contacting SLAT with an agent that modulates binding of SLAT to IP3R1. In additional aspects, the method comprises contacting IP3R1 with an agent that modulates binding of SLAT to IP3R1. In further aspects the agent decreases, reduces inhibits, suppresses or disrupts binding of SLAT to IP3R1. In additional aspects the agent enhances, stimulates, or promotes binding of SLAT to IP3R1. In further aspects, the agent comprises an antibody or an antibody fragment thereof that binds to SLAT or IP3R1. In additional aspects, the antibody that binds to SLAT comprises Abiocode R0522-5, R0522-4; Biorbyt orb67082, orb67083, orb67084; MyBioSource MBS710184; Amsbio TA305730; GeneTex GTX107700; or Novus Biologicals NB300-837. In further aspects, the antibody that binds to IP3R1 comprises LifeSpan BioSciences S24-18; antibodies online pSer1764; Novus Biologicals H00003708-A01; MyBioSource MBS854969, MBS716770; Bethyl Laboratories A302-158A; Bioorbyt orb88327; LifeSpan BioSciences LS-C138426-100; antibodies-online ABIN1493424; or Cell Signaling Technology 8568S, OriGene TA309404; Aviva Systems Biology OAEC04090; Abcam ab5804, ab111615; Bioss bs-8869R; Santa Cruz sc-6093, sc-26382; Acris Antibodies SP5415, SP5333P; Atlas Antibodies HPA016487, HPA014765; Alomone Labs ACC-019; GeneTex GTX63315; Enzo Life Sciences BML-SA254-0100, ALX-210-169-R100; Proteintech 19962-1-AP; Thermo Scientific Pierce Pa.3-901A; EMD Millipore ABS55; Abnova Corporation clone 2B6 H00003708-M01, PAB18402; Creative Biomart CABT-15622MH; St John's Laboratory STJ24266. In additional aspects, the antibody is humanized and comprises the CDRs of any of the antibodies that bind to SLAT set forth as Abiocode R0522-5, R0522-4; Biorbyt orb67082, orb67083, orb67084; MyBioSource MBS710184; Amsbio TA305730; GeneTex GTX107700; or Novus Biologicals NB300-837, or any of the antibodies that bind to IP3R1 set forth as LifeSpan BioSciences S24-18; antibodies online pSer1764; Novus Biologicals H00003708-A01; MyBioSource MBS854969, MBS716770; Bethyl Laboratories A302-158A; Bioorbyt orb88327; LifeSpan BioSciences LS-C138426-100; antibodies-online ABIN1493424; or Cell Signaling Technology 8568S. In further aspects the IP3R1 antibody is humanized and comprises the CDR of any of the antibodies that bind to IP3R1 set forth as LifeSpan BioSciences S24-18; antibodies online pSer1764; Novus Biologicals H00003708-A01; MyBioSource MBS854969, MBS716770; Bethyl Laboratories A302-158A; Bioorbyt orb88327; LifeSpan BioSciences LS-C138426-100; antibodies-online ABIN1493424; or Cell Signaling Technology 8568S, OriGene TA309404; Aviva Systems Biology OAEC04090; Abcam ab5804, ab111615; Bioss bs-8869R; Santa Cruz sc-6093, sc-26382; Acris Antibodies SP5415, SP5333P; Atlas Antibodies HPA016487, HPA014765; Alomone Labs ACC-019; GeneTex GTX63315; Enzo Life Sciences BML-SA254-0100, ALX-210-169-R100; Proteintech 19962-1-AP; Thermo Scientific Pierce Pa.3-901A; EMD Millipore ABS55; Abnova Corporation clone 2B6 H00003708-M01, PAB18402; Creative Biomart CABT-15622MH; St John's Laboratory STJ24266. In additional aspects, the agent comprises a peptide or a fragment of SLAT or IP3R1 polypeptide sequence. In further aspects, the SLAT peptide or fragment comprises or consists of the sequence MALRKELLKSIWYAFTALDVEKSGK-VSKSQLKVLSHNLYTVLHIPHDPVALEEHFRD DDDG-PVSSQGYMPYL (EF-hand domain, SEQ ID NO:1) or VLKQGYLWKRGHLRRNWAERWFQLQPSCLCYFG-SEECKEKRGIIPLDAHCCVEVLP DRDGKRCMFCVK-TANRTYEMSASDTRQRQEWTAAIQMAIR (PH domain, SEQ ID NO:2), or a subsequence thereof. In additional aspects, the IP3R1 peptide or fragment comprises or consists of the sequence NAQEKMVYSLVSVPEGNDIS-SIFELDPTTLRGGDSLVPRNSYVRLRHLCTNTWVH-STNI PIDKEEEKPVMLKIGTSPVKEDKEAFAIVPVS-PAEVRDLDFANDASKVLGSIAGKLEK GTITQNERRSVTKLLEDLVYFVTGGTNS (SEQ ID NO:3), or a subsequence thereof. In particular aspects, the IP3R1 peptide or fragment comprises or consists of the sequence HSTNIPIDKEEEKPVMLK (SEQ ID NO:4), or a subsequence thereof.

Exemplary SLAT sequences typically have a length from 5 to about 631 amino acid sequence includes all or portion of a SLAT amino acid sequence, or does not include all or a portion of a SLAT amino acid sequence. Additional examples of a SLAT amino acid sequence comprises, consists or consists essentially of from about residue 1 to residue 72, or from about residue 217 to residue 312 of SLAT or a subsequence portion, homologue, variant or derivative thereof. In further particular aspects, a SLAT sequence has a length of about 5-10, 10-20, 20-30, 30-40, 40-50, 50-75, 75-100, 100-150, 150-200, 200-250, 250-300, 300-350, 350-400, 400-500, 500-600 or 600-631 amino acid residues.

Exemplary IP3R1 sequences typically have a length from 5 to about 2710 amino acid sequence includes all or portion of an IP3R1 amino acid sequence, or does not include all or a portion of an IP3R1 amino acid sequence. Additional examples of an IP3R1 amino acid sequence comprises, consists or consists essentially of from about residue 346 to residue 490, or from about residue 346 to residue 441 of IP3R1 or a subsequence, portion, homologue, variant or derivative thereof. In further particular aspects, an IP3R1 sequence has a length of about 5-10, 10-20, 20-30, 30-40, 40-50, 50-75, 75-100, 100-150, 150-200, 200-250, 250-500, 500-750, 750-1000, 1000-1250, 1250-1500, 1500-1750, 1750-2000, 2000-2250, 2250-2500 or 2500-2710 amino acid residues.

In additional particular aspects, the agent comprises an inhibitory nucleic acid that reduces expression or activity of SLAT or IP3R1. In additional aspects, the inhibitory nucleic acid comprises a single or double strand RNA or DNA nucleic acid that binds to a genomic, transcribed or mRNA sequence of any of SLAT or IP3R1. In additional aspects, the agent comprises an aptamer. In further aspects, the agent comprises a fusion polypeptide or chimeric polypeptide. In further aspects, the fusion polypeptide or chimeric polypeptide comprises a TAT fusion polypeptide or chimeric polypeptide. In further aspects, the agent comprises a small molecule.

In another embodiment, the method comprises decreasing, reducing, inhibiting, suppressing, limiting or controlling an undesirable or aberrant immune response, disorder or disease, an inflammatory response, disorder or disease, inflammation, or an autoimmune response, disorder or disease, or an adverse symptom of an undesirable or aberrant immune response, disorder or disease, an inflammatory response, disorder or disease, inflammation, or an autoimmune response, disorder or disease. In particular aspects, the method comprises increasing, stimulating, enhancing, promoting, inducing or activating an immune response, inflammatory response or inflammation.

In another embodiment, the invention provides for a method of modulating activation or differentiation of CD4+ T cells in a subject comprising administering an agent that modulates binding of SLAT to IP3R1 thereby modulating activation or differentiation of CD4+ T cells in the subject. In further embodiments, the invention provides for a method of modulating an immune response in a subject comprising administering an agent that modulates binding of SLAT to IP3R1 thereby modulating the immune response in the subject. In particular aspects, the subject has or has had an undesirable or aberrant immune response, disorder or disease, an inflammatory response, disorder or disease, inflammation, or an autoimmune response, disorder or disease or an adverse symptom of an undesirable or aberrant immune response, disorder or disease, an inflammatory response, disorder or disease, inflammation, or an autoimmune response, disorder or disease. In further aspects, the subject is in need of treatment for an undesirable or aberrant immune response, disorder or disease, an inflammatory response, disorder or disease, inflammation, or an autoimmune response, disorder or disease or an adverse symptom of an undesirable or aberrant immune response, disorder or disease, an inflammatory response, disorder or disease, inflammation, or an autoimmune response, disorder or disease. In additional aspects, the subject is at risk of an undesirable or aberrant immune response, disorder or disease, an inflammatory response, disorder or disease, inflammation, or an autoimmune response, disorder or disease or an adverse symptom of an undesirable or aberrant immune response, disorder or disease, an inflammatory response, disorder or disease, inflammation, or an autoimmune response, disorder or disease. In further aspects, the undesirable or aberrant immune response, disorder or disease, inflammatory response, disorder or disease, inflammation, or autoimmune response, disorder or disease comprises rheumatoid arthritis, juvenile rheumatoid arthritis, osteoarthritis, psoriatic arthritis, multiple sclerosis (MS), encephalomyelitis, myasthenia gravis, systemic lupus erythematosus (SLE), asthma, allergic asthma, autoimmune thyroiditis, atopic dermatitis, eczematous dermatitis, psoriasis, Sjögren's Syndrome, Crohn's disease, aphthous ulcer, iritis, conjunctivitis, keratoconjunctivitis, ulcerative colitis (UC), inflammatory bowel disease (IBD), cutaneous lupus erythematosus, scleroderma, vaginitis, proctitis, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, interstitial lung fibrosis, Hashimoto's thyroiditis, autoimmune polyglandular syndrome, insulin-dependent diabetes mellitus (IDDM, type I diabetes), insulin-resistant diabetes mellitus (type 2 diabetes), immune-mediated infertility, autoimmune Addison's disease, pemphigus vulgaris, pemphigus foliaceus, dermatitis herpetiformis, autoimmune alopecia, vitiligo, autoimmune hemolytic anemia, autoimmune thrombocytopenic purpura, pernicious anemia, Guillain-Barre syndrome, stiff-man syndrome, acute rheumatic fever, sympathetic ophthalmia, Goodpasture's syndrome, systemic necrotizing vasculitis, antiphospholipid syndrome or an allergy, Behcet's disease, severe combined immunodeficiency (SCID), recombinase activating gene (RAG 1/2) deficiency, adenosine deaminase (ADA) deficiency, interleukin receptor common_chain (_c) deficiency, Janus-associated kinase 3 (JAK3) deficiency and reticular dysgenesis; primary T cell immunodeficiency such as DiGcorge syndrome, Nude syndrome, T cell receptor deficiency, MHC class II deficiency, T AP-2 deficiency (MHC class I deficiency), ZAP70 tyrosine kinase deficiency and purine nucleotide phosphorylase (PNP) deficiency, antibody deficiencies, X-linked agammaglobulinemia (Bruton's tyrosine kinase deficiency), autosomal recessive agammaglobulinemia, Mu heavy chain deficiency, surrogate light chain (_5/14 0.1) deficiency, Hyper-lgM syndrome: X-linked (CD40 ligand deficiency) ornon-X-linked, Ig heavy chain gene deletion, IgA deficiency, deficiency of IgG subclasses (with or without IgA deficiency), common variable immunodeficiency (CVID), antibody deficiency with normal immunoglobulins; transient hypogammaglobulinemia of infancy, interferon_receptor (IFNGR1, IFNGR2) deficiency, interleukin 12 or interleukin 12 receptor deficiency, immunodeficiency with thymoma, Wiskott-Aldrich syndrome (WAS protein deficiency), ataxia telangiectasia (ATM deficiency), X-linked lymphoproliferative syndrome (SH2D1A/SAP deficiency), hyper IgE syndrome or Graft vs. Host Disease (GVHD). In further aspects, the immune response or inflammatory response is an anti-cancer or anti-pathogen immune response or inflammatory response. In further aspects, the subject is a mammal or a human.

In additional embodiments, the invention provides a method of screening for an agent for binding of SLAT to IP3R1, the method comprising: a) contacting SLAT with IP3R1 in the presence of a test agent under conditions allowing binding of SLAT to IP3R1; and b) determining if the test agent modulates binding of SLAT to IP3R1, wherein determination that the test agent modulates binding of SLAT to IP3R1 indicates that the test agent is an agent that modulates binding of SLAT to IP3R1. In another embodiment, the invention provides a method of identifying an agent that modulates binding of SLAT to IP3R1, comprising: a) contacting SLAT with IP3R1 in the presence a test agent under conditions allowing binding of SLAT to IP3R1; and b) determining if the test agent modulates binding of SLAT to IP3R1, wherein determination that the test agent modulates binding of SLAT to IP3R1 indicates that the test agent is an agent that modulates binding of SLAT to IP3R1. In particular aspects, the method comprises screening for or identifying an agent for decreasing, reducing, inhibiting, suppressing, limiting or controlling undesirable or aberrant immune response, disorder or disease, an inflammatory response, disorder or disease, inflammation, or an autoimmune response, disorder or disease. In particular aspects, the contacting is in vivo or in vitro.

In additional embodiments, the invention provides a peptide comprising or consisting of a fragment of an IP3R1 amino acid sequence that binds to a SLAT amino acid sequence. In particular aspects, the SLAT peptide or fragment comprises or consists of the sequence MALRKELLKSIWYAFTALDVEKSGKVSKSQLKVLSHNLYTVLHIPHDPVALEEHFRD DDDGPVSSQGYMPYL (EF-hand domain, SEQ ID NO:1) or VLKQGYLWKRGHLRRNWAERWFQLQPSCLCYFGSEECKEKRGIIPLDAHC-CVEVLP DRDGKRCMFCVKTANRTYEMSAS-DTRQRQEWTAAIQMAIR (PH domain, SEQ ID NO:2), or a subsequence thereof.

In another embodiment, the invention provides a peptide comprising or consisting of a fragment of a SLAT amino acid sequence that binds to an IP3R1 amino acid sequence. In particular aspects, the IP3R1 peptide or fragment comprises or consists of the sequence NAQEKMVYSLVSVPEGNDISSIFELDPTTLRGGDSLVPRNSYVRLRHLCTNTWVHSTNI PIDKEEEKPVMLKIGTSPVKEDKEAFAIVPVS-PAEVRDLDFANDASKVLGSIAGKLEK GTITQNERRS-VTKLLEDLVYFVTGGTNS (SEQ ID NO:3), or a subsequence thereof. In additional aspects, the IP3R1 peptide or fragment comprises or consists of the sequence HSTNIPIDKEEEKPVMLK (SEQ ID NO:4), or a subsequence thereof. In another embodiment, the invention provides for a pharmaceutical composition comprising one or more of the SLAT or IP3R1 peptides.

BRIEF DESCRIPTION OF DRAWINGS

In the figures, which illustrate, by way of example only, embodiments described herein:

SLAT interacts with IP3R1 in stimulated CD4+ T cells.

Mapping of the SLAT-binding IP3R1 region.

Mapping of the IP3R1-binding SLAT domains.

$Ca^{2+}$ binding to SLAT and $Ca^{2+}$ dependence of the SLAT-IP3R1 interaction.

In FIG. 4b purified calmodulin (CaM) and GST alone were used as positive or negative controls, respectively.

Mapping of a minimal SLAT-binding motif in the IP3R1.

Effect of disrupting the SLAT-IP3R1 interaction on T cell functions. FIG. 6a Schematic representation of the TAT-HA peptide and its fusions with IP3R1 fragments f2.1 and f2.1 Δ 18.

FIG. 6b SLAT IPs (left) or whole cell lysates (right) of B6 CD4+ T cells stimulated with crosslinked anti-CD3 plus-CD28 mAbs, which were pretreated with the indicated TAT-HA proteins, were Immunoblotted with anti-IP3R1 (top row) or anti-SLAT (bottom row) Abs. Percentage of inhibition relative to the control TAT-HA protein was quantified by densitometry using the ImageJ software.

FIGS. 6c-6d $[Ca^{2+}]i$ recordings of T cells pretreated with the indicated TAT-HA proteins and stimulated as in (b). Stimulations and recordings were performed in absence (FIG. 6c) or presence (FIG. 6d) of EGTA. In (FIG. 6c), Def6−/− CD4+ T cells were used as a control.

FIG. 7 shows the SLAT-IP3R1 interaction is direct. Far-western blots were performed as described. Recombinant proteins corresponding to the GST or GST-IP3R1-f2 were resolved by SDS-PAGE and transferred to nitrocellulose membranes. Proteins were denatured, renatured, and incubated with purified His-SLAT recombinant protein. After washing, bound proteins were detected by anti-SLAT, followed by anti-GST Ab immunoblotting.

FIG. 8a shows immunoblots of anti-Myc SLAT IPs (IP: Myc; left panels) or whole cell lysates (WCL; right panels). HEK-293T cells cotransfected with the indicated Myc-tagged SLAT (or empty; EV) vectors plus Flag-tagged IP3R1. Arrowheads indicate the position of the Myc-SLAT proteins.

FIG. 8b shows schematic representation of GST-SLAT recombinant proteins.

FIG. 8c shows cell lysates from HEK-293T overexpressing Flag-tagged IP3R1 were precleared and incubated with gluthatione-bound GST fusion proteins for 1 h at 4° C. Eluted proteins were subjected to SDS-PAGE and immunoblotted with the indicated antibodies. Data shown are representative of 2 experiments.

FIG. 9 shows Alignment of the 18-amino acid IP3R1 motif critical for the interaction with SLAT in mouse IP3R1, IP3R2 and IP3R3 (top), and IP3R1 proteins from the indicated organisms (bottom). Motifs were aligned using the T-Coffee program, and residues were shaded according to % of similarity using the Boxshade software. Black shading indicates amino acid identity.

FIG. 11a shows B6 CD4+ T cells were pre-incubated with TAT fusion proteins and stimulated as in FIG. 6e for the indicated times (min). Equal protein amounts were resolved by SDS-PAGE and immunoblotted with the indicated Abs. Data shown are representative of 2 experiments.

FIG. 11b shows TAT fusion peptide transduction does not alter proximal TCR signaling. Jurkat (JA16) T cells were cotransfected with empty vector (EV), or with Myc-tagged SLAT in the absence or presence of a pEF vector expressing TAT-HA 2.1, together with NF-κB-Luc and β-Gal reporter plasmids. Cells were stimulated or not, and normalized Luc activity was determined as in FIG. 6f. Data shown are representative of 3 experiments.

DETAILED DESCRIPTION

Figure 1A:
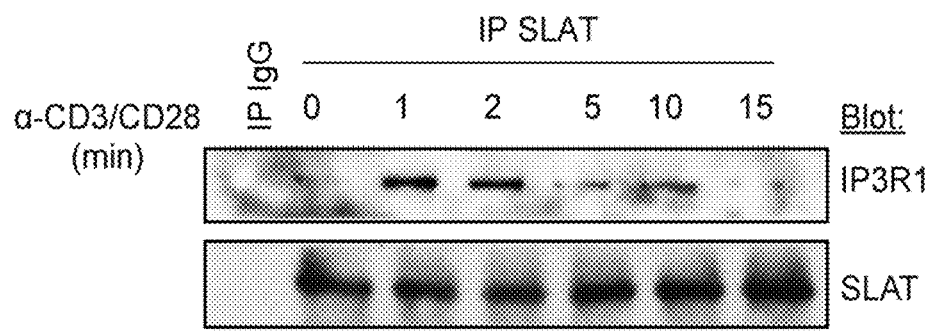
FIG. 1a B6 CD4+ T cells were stimulated with anti-CD3 plus-CD28 mAbs for the indicated times. SLAT was immunoprecipitated and proteins separated by SDS-PAGE were immunoblotted with an anti-IP3R1 mAb (top row) or with an anti-SLAT Ab (bottom row). IP IgG, normal IgG IP control.

A direct, TCR-induced and $Ca^{2+}$-sensitive association between SLAT and the IP3R1 has been discovered and characterized. Both the N-terminal EF-hand domain and the PH domain of SLAT interacted with IP3R1 and were important for SLAT-mediated $Ca^{2+}$ regulation. It has further been indicated that a short motif within the LBD of IP3R1 binds SLAT. The biological relevance of this association was established by demonstrating that its disruption in CD4+ T cells impaired TCR-induced $Ca^{2+}$/NFAT signaling and cytokine production. Thus, SLAT is an IP3R1-interacting protein that critically regulates the TCR-mediated $Ca^{2+}$/NFAT signaling pathway.

As disclosed herein, methods and uses include modulating (e.g., reducing, inhibiting, suppressing, or limiting) binding between SLAT and IP3R1. Methods and uses can be performed in vivo, such as in a subject, in vitro, ex vivo, in a cell, in solution, in solid phase or in silica. In one embodiment, a method or use includes contacting an inhibitor of binding between SLAT and IP3R1 thereby reducing, inhibiting, decreasing, suppressing, or limiting binding between SLAT and IP3R1.

As used herein, the term "modulate," means an alteration or effect of the term modified. For example, the term modulate can be used in various contexts to refer to an alteration or effect of an activity, a function, or expression of a polypeptide, gene or signaling pathway, or a physiological condition or response of an organism. Methods and uses include modulating (e.g., decrease, reduce, inhibit, suppress, limit or control) one or more functions, activities or expression of SLAT or IP3R1 in solution, in solid phase, in a cell, in vitro, ex vivo or in vivo. Thus, where the term "modulate" is used to modify the term "SLAT" or "IP3R1" this means that a SLAT or IP3R1 activity, function, or expression is altered or affected (e.g., decreased, reduced, inhibited, suppressed, limited, controlled or prevented, etc.). Detecting an alteration or an effect on SLAT or IP3R1 activity, function or expression can be determined as set forth herein using cell based, in vitro or in vivo assays, such as an animal model.

As disclosed herein, inhibition of binding between SLAT and IP3R1 polypeptide can lead to various consequences, such as effects on a SLAT and IP3R1 function or activity. Accordingly, SLAT and IP3R1 sequences, subsequences, variants and derivatives, and polymorphisms as disclosed herein, including compositions including SLAT and/or IP3R1, are useful in various methods and uses such as modulation and treatment methods and uses, including, for example, treatment of numerous responses, disorders and diseases, both chronic and acute. In one embodiment, a method of treating a SLAT mediated or dependent response, disorder, or disease, includes administering an inhibitor of binding between SLAT and IP3R1 to a subject in an amount that treats the SLAT mediated or dependent response, disorder, or disease.

Thus, in one embodiment, there is provided a method of modulating an immune response, comprising contacting SLAT or IP3R1 with an agent that modulates binding of SLAT to IP3R1, thereby modulating an immune response. In another embodiment, there is provided a method of modulating activation or differentiation of CD4+ T cells, comprising contacting SLAT or IP3R1 with an agent that modulates binding of SLAT to IP3R1, thereby modulating activation or differentiation of CD4+ T cells. In another embodiment, the invention provides for use of an agent for modulating binding of SLAT to IP3R1, to modulate an immune response. In another embodiment, the invention provides for use of an agent for modulating binding of SLAT to IP3R1, to modulate activation or differentiation of CD4+ T cells. In another embodiment, the invention provides for use of an agent in the manufacture of a medicament for modulating binding of SLAT to IP3R1, thereby modulating an immune response. In another embodiment, the invention provides for use of an agent in the manufacture of a medicament for modulating binding of SLAT to IP3R1, thereby modulating activation or differentiation of CD4+ T cells. In another embodiment, the invention provides for use of an agent for modulating binding of SLAT to IP3R1 in the manufacture of a medicament for modulating an immune response. In another embodiment, the invention provides for use of an agent for modulating binding of SLAT to IP3R1 in the manufacture of a medicament for modulating activation or differentiation of CD4+ T cells. In particular aspects the method comprises contacting SLAT with an agent that modulates binding of SLAT to IP3R1. In additional aspects, the method comprises contacting IP3R1 with an agent that modulates binding of SLAT to IP3R1. In further aspects the agent decreases, reduces inhibits, suppresses or disrupts binding of SLAT to IP3R1. In additional aspects the agent enhances, stimulates, or promotes binding of SLAT to IP3R1.

Non-limiting examples of agents include small molecules, such as small organic molecules having a molecular weight of less than about 1,000 Daltons (1 kDa), for example less than about 800 Daltons, or less than about 500 Daltons. Small organic compounds, whether naturally-occurring or artificially created (e.g., via chemical synthesis) that have relatively low molecular weight are not proteins, polypeptides, or nucleic acids. Small molecules typically have multiple carbon-carbon bonds.

Additional non limiting examples of immune response modulators include polypeptides, peptides and proteins. As used herein, the terms "peptide," "polypeptide" and "protein" are used interchangeably and refer to two or more amino acids covalently linked by an amide bond or non-amide equivalent. Polypeptides include full length native polypeptide, and "modified" forms such as subsequences, variant sequences, and fusion/chimeric sequences.

Peptides include L- and D-isomers, and combinations thereof. Peptides can include modifications typically associated with post-translational processing of proteins, for example, cyclization (e.g., disulfide or amide bond), phosphorylation, glycosylation, carboxylation, ubiquitination, myristylation, or lipidation. Modified peptides can have one or more amino acid residues substituted with another residue, added to the sequence or deleted from the sequence. Specific examples include one or more amino acid substitutions, additions or deletions (e.g., 1-3, 3-5, 5-10, 10-15, 10-20, or more).

Subsequences and fragments refer to polypeptides having one or more fewer amino acids in comparison to a reference (e.g., native) polypeptide sequence. An antibody subsequence that specifically binds to SLAT or IP3R1 will retain at least partial binding affinity for as full length reference antibody that specifically binds to SLAT or IP3R1.

Additional non-limiting examples of agents include antibodies and subsequences/fragments that have SLAT or IP3R1 binding activity. The term "antibody" refers to a protein that binds to another molecule (antigen) via heavy and light chain variable domains, denoted $V_H$ and $V_L$, respectively. An antibody typically includes a constant and/or variable (e.g., hypervariable, such as CDR or FR) region. Regions in the CDRs (CDR1, CDR2, and/or CDR3) are considered to confer antigen binding specificity and/or affinity. "Antibody" may refer to any polyclonal or monoclonal immunoglobulin molecule, or mixtures thereof, such as IgM, IgG, IgA, IgE, IgD. Antibodies belong to any antibody class or subclass. Exemplary subclasses for IgG are $IgG_1$, $IgG_2$, $IgG_3$ and $IgG_4$.

"Monoclonal," when used in reference to an antibody, refers to an antibody that is based upon, obtained from or derived from a single clone, including any eukaryotic, prokaryotic, or phage clone. A "monoclonal" antibody is therefore defined herein structurally, and not the method by which it is produced.

Antibodies include kappa or lambda light chain sequences, either full length as in naturally occurring antibodies, mixtures thereof (i.e., fusions of kappa and lambda chain sequences), and subsequences/fragments thereof. Naturally occurring antibody molecules contain two kappa and two lambda light chains. The primary difference between kappa and lambda light chains is in the sequences of the constant region.

An antibody that includes or consists of a Heavy (H) chain and/or Light (L) chain or fragment of a Heavy (H) chain or Light (L) chain can include a single H or L chain or a single H or L chain fragment, or a plurality (2, 3, 4 or more) of Heavy (H) chains and/or Light (L) chains, or a plurality of fragments of Heavy (H) chains and/or Light (L) chains. A fusion polypeptide that includes a Heavy (H) chain and/or Light (L) chain of an antibody or fragment can but is not required to include 2 Heavy (H) chains and 2 Light (L) chains and therefore fusion polypeptides as set forth herein. An antibody or fragment thereof may be an oligomeric (higher order or valent) forms, such as a trimer, tetramer, pentamer, hexamer, heptamer, and so forth, with other antibodies, fragments thereof, Heavy (H) chain, Light (L) chain, or polypeptides distinct from an antibody Heavy (H) or Light (L) chain.

An "antibody" subsequence refers to a functional fragment or subsequence of an immunoglobulin having antigen (e.g., SLAT or IP3R1) binding affinity. Non-limiting examples of antibody subsequences include an Fab, Fab', $F(ab')_2$, Fv, Fd, single-chain Fv (scFv), disulfide-linked Fvs (sdFv), $V_L$, $V_H$, diabody (($V_L$—$V_H$)$_2$ or ($V_H$—$V_L$)$_2$), triabody (trivalent), tetrabody (tetravalent), minibody (($scF_V$-$C_H3$)$_2$), IgGdeltaCH2, scFv-Fc or $(scFv)_2$-Fc fragment. In particular aspects, an Fab, Fab', $F(ab')_2$, Fv, Fd, single-chain Fv (scFv), disulfide-linked Fvs (sdFv), $V_L$, $V_H$, diabody (($V_L$-$V_H$)$_2$ or ($V_H$—$V_L$)$_2$), triabody (trivalent), tetrabody (tetravalent), minibody ((scFv-$C_H3$)$_2$), IgGdeltaCH2, scFv-Fc or $(scFv)_2$-Fc subsequence.

Antibody subsequences, including single-chain antibodies, can include all or a portion of heavy or light chain variable region(s) (e.g., CDR1, CDR2 or CDR3) alone or in combination with all or a portion of one or more of the following: hinge region, CH1, CH2, and CH3 domains. Also included are antigen-binding subsequences of any combination of heavy or light chain variable region(s) (e.g., CDR1, CDR2 or CDR3) with a hinge region, CH1, CH2, and CH3 domains.

Antibodies include mammalian, human, humanized, and primatized sequences. The term "human," in reference to an antibody means that the amino acid sequence is fully human. A "human antibody" therefore refers to an antibody having human immunoglobulin amino acid sequences, i.e., human heavy and light chain variable and constant regions that specifically bind to target. That is, all of the antibody amino acids are human or can or do exist in a human antibody. Thus, for example, an antibody that is non-human may be made fully human by substituting the non-human amino acid residues with amino acid residues that can or do exist in a human antibody. Amino acid residues present in human antibodies, CDR region maps and human antibody consensus residues are known in the art (see, e.g., Kabat, *Sequences of Proteins of Immunological Interest*, 4$^{th}$ Ed. US Department of Health and Human Services. Public Health Service (1987); and Chothia and Lesk *J. Mol. Biol.* 186:651 (1987)). A consensus sequence of human $V_H$ subgroup III, based on a survey of 22 known human $V_H$ III sequences, and a consensus sequence of human $V_L$ kappa-chain subgroup I, based on a survey of 30 known human kappa I sequences is described in Padlan *Mol. Immunol.* 31:169 (1994); and Padlan *Mol. Immunol.* 28:489 (1991)). Human antibodies therefore include antibodies in which one or more amino acid residues have been substituted with one or more amino acids present in another human antibody.

The term "humanized" when used in reference to an antibody, means that the amino acid sequence of the antibody has non-human amino acid residues (e.g., mouse, rat, goat, rabbit, non-human primate, etc.) of one or more determining regions (CDRs) that specifically bind to a target in an acceptor human immunoglobulin molecule, and one or more human amino acid residues in the Fv framework region (FR), which are amino acid residues that flank the CDRs. Human framework region residues of the immunoglobulin can be replaced with corresponding non-human residues. Residues in the human FRs can therefore be substituted with a corresponding residue from the non-human CDR donor antibody to alter, generally to improve, antigen affinity or specificity, for example. In addition, a humanized antibody may include residues, which are found neither in the human antibody nor in the donor CDR or FR sequences. For example, a FR substitution at a particular position that is not found in a human antibody or the donor non-human antibody may be predicted to improve binding affinity or specificity human antibody at that position.

Any mouse, rat, guinea pig, goat, non-human primate (e.g., ape, chimpanzee, macaque, orangutan, etc.) or other animal antibody may be used as a CDR donor for producing humanized antibody. Human framework region residues can be replaced with corresponding non-human residues (e.g., from the donor variable region). Residues in the human framework regions can therefore be substituted with a corresponding residue from the non-human CDR donor antibody. A humanized antibody may include residues, which are found neither in the human antibody nor in the donor CDR or framework sequences.

Antibodies referred to as "primatized" are within the meaning of "humanized" as used herein, except that the acceptor human immunoglobulin molecule and framework region amino acid residues may be any primate amino acid residue (e.g., ape, gibbon, gorilla, chimpanzees orangutan, macaque), in addition to any human residue.

Antibodies can be generated using techniques including conventional hybridoma technology using splenocytes isolated from immunized animals that respond to the antigen and fused with myeloma cells, recombinant, and phage display technologies, or a combination thereof (see U.S. Pat. Nos. 4,902,614, 4,543,439, and 4,411,993; see, also *Monoclonal Antibodies, Hybridomas: A New Dimension in Biological Analyses*, Plenum Press, Kennett, McKearn, and Bechtol (eds.), 1980, and Harlow et al., *Antibodies: A Laboratory Manual*, Cold Spring Harbor Laboratory Press, 2nd ed. 1988). Monoclonal antibodies can also be obtained by direct cloning of immunoglobulin sequences from animals, including primate or human subjects. Additional methods for producing human polyclonal antibodies and human monoclonal antibodies are described (see, e.g., Kuroiwa et al., *Nat. Biotechnol.* 20:889 (2002); WO 98/24893; WO 92/01047; WO 96/34096; WO 96/33735; U.S. Pat. Nos. 5,413,923; 5,625,126; 5,633,425; 5,569,825; 5,661,016; 5,545,806; 5,814,318; 5,885,793; 5,916,771; and 5,939,598). An overview of the technology for producing human antibodies is described in Lonberg and Huszar (*Int. Rev. Immunol.* 13:65 (1995)).

Transgenic animals with one or more human immunoglobulin genes (kappa or lambda) that do not express endogenous immunoglobulins are described, for example in, U.S. Pat. No. 5,939,598. Such animals can therefore be used to produce human antibodies. A specific non-limiting example is the human transchromosomic KM Mice™ (Tomizuka et al., *Proc. Natl. Acad. Sci. USA* 97:722 (2000); and Ishida et al., Cloning Stem Cells 4:91 (2004)) which can produce human immunoglobulin genes (WO02/43478) or HAC mice (WO02/092812).

Antibody subsequences can also be produced by proteolytic hydrolysis. An antibody, for example, can be digested with pepsin or papain. Antibody fragments produced by enzymatic cleavage with pepsin provide a 5S fragment denoted F(ab')$_2$. This fragment can be further cleaved using a thiol reducing agent to produce 3.5S Fab' monovalent fragments. Alternatively, an enzymatic cleavage using pepsin produces two monovalent Fab' fragments and the Fc fragment directly (see, e.g., U.S. Pat. Nos. 4,036,945 and 4,331,647; and Edelman et al., *Methods Enymol* 1:422 (1967)). Other methods of cleaving antibodies, such as separation of heavy chains to form monovalent light-heavy chain fragments, further cleavage of fragments, or other enzymatic or chemical may also be used.

Antibodies can be humanized using a variety of techniques known in the art including, for example, CDR-grafting (EP 239,400; WO91/09967; U.S. Pat. Nos. 5,225,539; 5,530,101; and 5,585,089), veneering or resurfacing (EP 592,106; EP 519,596; Padlan, *Molecular Immunol.* 28:489 (1991); Studnicka et al., *Protein Engineering* 7:805 (1994); Roguska. et al., *Proc. Nat'l. Acad. Sci. USA* 91:969 (1994)), and chain shuffling (U.S. Pat. No. 5,565,332). Human consensus sequences (Padlan, *Mol. Immunol.* 31:169 (1994); and Padlan, *Mol. Immunol.* 28:489 (1991)) can be used to humanize antibodies (Carter et al., *Proc. Natl. Acad. Sci. USA* 89:4285 (1992); and Presta et al., *J. Immunol.* 151:2623 (1993)).

Methods for producing chimeric antibodies are known in the art (e.g., Morrison, *Science* 229:1202 (1985); Oi et al., *BioTechniques* 4:214 (1986); Gillies et al., *J. Immunol. Methods* 125:191 (1989); and U.S. Pat. Nos. 5,807,715; 4,816,567; and 4,816,397). Chimeric antibodies in which a variable domain from an antibody of one species is substituted for the variable domain of another species are described, for example, in Munro, *Nature* 312:597 (1984); Neuberger et al., *Nature* 312:604 (1984); Sharon et al., *Nature* 309:364 (1984); Morrison et al., *Proc. Nat'l. Acad. Sci. USA* 81:6851 (1984); Boulianne et al., *Nature* 312:643 (1984); Capon et al., *Nature* 337:525 (1989); and Traunecker et al., *Nature* 339:68 (1989).

Particular non-limiting examples of an antibody that binds to SLAT comprises Abiocode R0522-5, R0522-4; Biorbyt orb67082, orb67083, orb67084; MyBioSource MBS710184; Amsbio TA305730; GeneTex GTX107700; or Novus Biologicals NB300-837. Particular non-limiting examples of an antibody that binds to IP3R1 comprises LifeSpan BioSciences S24-18; antibodies online pSer1764; Novus Biologicals H00003708-A01; MyBioSource MBS854969, MBS716770; Bethyl Laboratories A302-158A; Bioorbyt orb88327; LifeSpan BioSciences LS-C138426-100; antibodies-online ABIN1493424; or Cell Signaling Technology 8568S, OriGene TA309404; Aviva Systems Biology OAEC04090; Abcam ab5804, ab111615; Bioss bs-8869R; Santa Cruz sc-6093, sc-26382; Acris Antibodies SP5415, SP5333P; Atlas Antibodies HPA016487, HPA014765; Alomone Labs ACC-019; GeneTex GTX63315; Enzo Life Sciences BML-SA254-0100, ALX-210-169-R100; Proteintech 19962-1-AP; Thermo Scientific Pierce Pa.3-901A; EMD Millipore ABS55; Abnova Corporation clone 2B6 H00003708-M01, PAB18402; Creative Biomart CABT-15622MH; St John's Laboratory STJ24266.

An antibody that is humanized can include one or more (2 or all 3) CDRs of any of the antibodies that bind to SLAT set forth as Abiocode R0522-5, R0522-4; Biorbyt orb67082, orb67083, orb67084; MyBioSource MBS710184; Amsbio TA305730; GeneTex GTX107700; or Novus Biologicals NB300-837, or any of the antibodies that bind to IP3R1 set forth as LifeSpan BioSciences S24-18; antibodies online pSer1764; Novus Biologicals H00003708-A01; MyBioSource MBS854969, MBS716770; Bethyl Laboratories A302-158A; Bioorbyt orb88327; LifeSpan BioSciences LS-C138426-100; antibodies-online ABIN1493424; or Cell Signaling Technology 8568S. In further aspects the IP3R1 antibody is humanized and comprises the CDR of any of the antibodies that bind to IP3R1 set forth as LifeSpan BioSciences S24-18; antibodies online pSer1764; Novus Biologicals H00003708-A01; MyBioSource MBS854969, MBS716770; Bethyl Laboratories A302-158A; Bioorbyt orb88327; LifeSpan BioSciences LS-C138426-100; antibodies-online ABIN1493424; or Cell Signaling Technology 8568S, OriGene TA309404; Aviva Systems Biology OAEC04090; Abcam ab5804, ab111615; Bioss bs-8869R; Santa Cruz sc-6093, sc-26382; Acris Antibodies SP5415, SP5333P; Atlas Antibodies HPA016487, HPA014765; Alomone Labs ACC-019; GeneTex GTX63315; Enzo Life Sciences BML-SA254-0100, ALX-210-169-R100; Proteintech 19962-1-AP; Thermo Scientific Pierce Pa.3-901A; EMD Millipore ABS55; Abnova Corporation clone 2B6 H00003708-M01, PAB18402; Creative Biomart CABT-15622MH; St John's Laboratory STJ24266.

In additional aspects, the agent comprises a peptide or a fragment of SLAT or IP3R1 polypeptide sequence. In further aspects, the SLAT peptide or fragment comprises or consists of the sequence MALRKELLKSIWYAFTALDVEKSGK-VSKSQLKVLSHNLYTVLHIPHDPVALEEHFRD DDDG-PVSSQGYMPYL (EF-hand domain, SEQ ID NO:1) or VLKQGYLWKRGHLRRNWAERWFQLQPSCLCYFG-SEECKEKRGIIPLDAHCCVEVLP DRDGKRCMFCVK-TANRTYEMSASDTRQRQEWTAAIQMAIR (PH domain, SEQ ID NO:2), or a subsequence thereof. In additional aspects, the IP3R1 peptide or fragment comprises or consists of the sequence NAQEKMVYSLVSVPEGNDIS-SIFELDPTTLRGGDSLVPRNSYVRLRHLCTNTWVH-STNI PIDKEEEKPVMLKIGTSPVKEDKEAFAIVPVS-PAEVRDLDFANDASKVLGSIAGKLEK GTITQNERRSVTKLLEDLVYFVTGGTNS (SEQ ID NO:3), or a subsequence thereof. In particular aspects, the IP3R1 peptide or fragment comprises or consists of the sequence HSTNIPIDKEEEKPVMLK (SEQ ID NO:4), or a subsequence thereof.

Exemplary SLAT sequences typically have a length from 5 to about 631 amino acid sequence includes all or portion of a SLAT amino acid sequence, or does not include all or a portion of a SLAT amino acid sequence. Additional examples of a SLAT amino acid sequence comprises, consists or consists essentially of from about residue 1 to residue 72, or from about residue 217 to residue 312 of SLAT or a subsequence portion, homologue, variant or derivative thereof. In further particular aspects, a SLAT sequence has a length of about 5-10, 10-20, 20-30, 30-40, 40-50, 50-75, 75-100, 100-150, 150-200, 200-250, 250-300, 300-350, 350-400, 400-500, 500-600 or 600-631 amino acid residues.

Exemplary IP3R1 sequences typically have a length from 5 to about 2710 amino acid sequence includes all or portion of an IP3R1 amino acid sequence, or does not include all or a portion of an IP3R1 amino acid sequence. Additional examples of an IP3R1 amino acid sequence comprises, consists or consists essentially of from about residue 346 to residue 490, or from about residue 346 to residue 441 of IP3R1 or a subsequence, portion, homologue, variant or derivative thereof. In further particular aspects, an IP3R1 sequence has a length of about 5-10, 10-20, 20-30, 30-40, 40-50, 50-75, 75-100, 100-150, 150-200, 200-250, 250-500, 500-750, 750-1000, 1000-1250, 1250-1500, 1500-1750, 1750-2000, 2000-2250, 2250-2500 or 2500-2710 amino acid residues.

A "functional sequence" or "functional variant," or "functional polymorphism," as used herein refers to a sequence, subsequence, variant or derivative, or polymorphism that possesses at least one partial function or activity characteristic of a native wild type or full length counterpart polypeptide. For example, SLAT or IP3R1 polypeptide subsequence, variant or derivative, or polymorphism, as disclosed herein, can function to modulate (e.g., inhibit, reduce or decrease) binding between SLAT and IP3R1. Embodiments herein include SLAT and IP3R1 sequences, subsequences, and fragments, variants and derivatives, and polymorphisms that typically retain, at least a part of, one or more functions or activities of a corresponding reference or an unmodified native wild type or full length counterpart SLAT or IP3R1 sequence. Compositions, methods and uses therefore include SLAT and IP3R1 polypeptide sequences, subsequences, variants and derivatives, and polymorphisms, having one or more functions or activities of wild type native SLAT and/or IP3R1.

In additional particular aspects, the agent comprises an inhibitory nucleic acid that reduces expression or activity of SLAT or IP3R1. In additional aspects, the inhibitory nucleic acid comprises a single or double strand RNA or DNA nucleic acid that binds to a genomic, transcribed or mRNA sequence of any of SLAT or IP3R1. Such inhibitory nucleic acids can be readily incorporated into various vectors (e.g., liposomes, nanoparticles, viral vectors, etc.) for introduction into cells using methods known to one of skill in the art.

Inhibitory nucleic acids can be a single-stranded sequence, or form a double- or triple-stranded sequence. In particular aspects, an inhibitory nucleic acid is a micro-RNA (miRNA), siRNA, shRNA, trans-splicing RNA, antisense RNA or triplex forming RNA.

Inhibitory, antisense, siRNA (small interfering RNA), miRNA (micro RNA), shRNA (small hairpin RNA), RNAi and antisense oligonucleotides can modulate expression of a SLAT or IP3R1 encoding gene, thereby modulating an immune response, response, activation or differentiation of CD4+ T cells, etc. Such molecules include those able to inhibit expression or activity of a SLAT or IP3R1 gene involved in mediation of a disease process, thereby reducing, inhibiting or alleviating one or more symptoms of a disease.

Antisense includes single, double or triple stranded polynucleotides and peptide nucleic acids (PNAs) that bind RNA transcript or DNA (e.g., genomic DNA). Oligonucleotides derived from the transcription initiation site of a SLAT or IP3R1 gene, e.g., between positions −10 and +10 from the start site, are another particular example. Triplex forming antisense can bind to double strand DNA thereby inhibiting transcription of the gene. "RNAi" is the use of single or double stranded RNA sequences for inhibiting gene expression (see, e.g., Kennerdell et al., Cell 95:1017 (1998); and Fire et al., Nature, 391:806 (1998)). Double stranded RNA sequences from a SLAT or IP3R1 gene may therefore be used to inhibit or prevent gene expression/transcription in accordance with the methods and uses of the invention. Antisense and RNAi can be produced based upon nucleic acids encoding a SLAT or IP3R1 protein. For example, a single or double stranded nucleic acid (e.g., RNA) can target a SLAT or IP3R1 gene.

A "siRNA" refers to a therapeutic molecule involved in the RNA interference process for a sequence-specific post-transcriptional gene silencing or gene knockdown. siRNAs have homology with the sequence of the cognate mRNA of a SLAT or IP3R1 gene. Small interfering RNAs (siRNAs) can be synthesized in vitro or generated by ribonuclease III cleavage from longer dsRNA and are the mediators of sequence-specific mRNA degradation. siRNA or other such nucleic acids of the invention can be chemically synthesized using appropriately protected ribonucleoside phosphoramidites and a conventional DNA/RNA synthesizer. The siRNA can be synthesized as two separate, complementary RNA molecules, or as a single RNA molecule with two complementary regions.

Specific siRNA constructs for inhibiting mRNA of a target gene may be between 15-50 nucleotides in length, and more typically about 20-30 nucleotides in length. Such nucleic acid molecules can be readily incorporated into various vectors for introduction into cells using methods known to one of skill in the art. Commercial suppliers of synthetic RNA molecules or synthesis reagents include Applied Biosystems (Foster City, Calif., USA), Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA) and Cruachem (Glasgow, UK).

In additional aspects, the agent comprises an aptamer. In further aspects, the agent comprises a fusion polypeptide or chimeric polypeptide. In particular aspect, a fusion can comprise SLAT or IP3R1 protein, such as a fragment (e.g., EF-hand domain or PH domain) fused to an immunoglobulin sequence, such as an Fc domain. In further aspects, the fusion polypeptide or chimeric polypeptide comprises a TAT fusion polypeptide or chimeric polypeptide. Combination fusions are also provided.

SLAT and IP3R1 sequences, subsequences, variants and derivatives, and polymorphisms may have an activity or function substantially the same or greater or less than 2-5, 5-10, 10-100, 100-1000 or 1000-10,000-fold activity or function than a comparison SLAT and IP3R1 sequence. For example, a SLAT or IP3R1 sequence, subsequence or a variant or derivative could have a function or activity greater or less than 2-5, 5-10, 10-100, 100-1000 or 1000-10,000-fold function or activity of a reference SLAT or IP3R1 to modulate (e.g., decrease, reduce, or inhibit) binding between SLAT and IP3R1, or to modulate an undesirable or aberrant immune response, immune disorder, inflammatory response, or inflammation; modulate an autoimmune response, disorder or disease; or modulate regulatory T cell function.

In particular embodiments, a functional sequence shares at least 50% identity with a reference sequence, for example, a SLAT or IP3R1 polypeptide sequence that is capable of modulating (e.g., inhibiting, reducing or decreasing) binding of SLAT to IP3R1, or modulating an activity, function or expression of SLAT and/or IP3R1. In other embodiments, the sequences have at least 60%, 70%, 75% or more identity (e.g., 80%, 85% 90%, 95%, 96%, 97%, 98%, 99% or more identity) to a reference sequence, e.g., SLAT or IP3R1.

The term "identity" and grammatical variations thereof, mean that two or more referenced entities are the same. Thus, where two polypeptide (e.g., SLAT or IP3R1) sequences are identical, they have the same amino acid sequence, at least within the referenced region or portion. Where two nucleic acid sequences are identical, they have the same polynucleotide sequence, at least within the referenced region or portion. The identity can be over a defined area (region or domain) of the sequence. An "area of identity" refers to a portion of two or more referenced entities that are the same. Thus, where two protein or nucleic acid sequences are identical over one or more sequence regions they share identity within that region.

The percent identity can extend over the entire sequence length of the polypeptide (e.g., SLAT or IP3R1). In particular aspects, the length of the sequence sharing the percent identity is 5 or more contiguous amino acids, e.g., 5, 6, 7, 8, 9, 10, 11, 12, 13, 14, 15, 16, 17, 18, 19, 20, 21, 22, 23, 24, 25, 26, 27, 28, 29, 30, etc. contiguous amino acids. In additional particular aspects, the length of the sequence sharing the percent identity is 31 or more contiguous amino acids, e.g., 32, 33, 34, 35, 36, 37, 38, 39, 40, etc. contiguous amino acids. In further particular aspects, the length of the sequence sharing the percent identity is 41 or more contiguous amino acids, e.g., 42, 43, 44, 45, 45, 47, 48, 49, 50, etc., contiguous amino acids. In yet additional particular aspects, the length of the sequence sharing the percent identity is 50 or more contiguous amino acids, e.g., 50-55, 55-60, 60-65, 65-70, 70-75, 75-80, 80-85, 85-90, 90-95, 95-100, 100-110, 110-120, 120-130, 130-140, 140-150, 150-175, 175-200, etc. contiguous amino acids.

The terms "homologous" or "homology" mean that two or more referenced entities share at least partial identity over a given region or portion. "Areas, regions or domains" of homology or identity mean that a portion of two or more referenced entities share homology or are the same. Thus, where two sequences are identical over one or more sequence regions they share identity in these regions. "Substantial homology" means that a molecule is structurally or functionally conserved such that it has or is predicted to have at least partial structure or function of one or more of the structures or functions (e.g., a biological function or activity) of the reference molecule, or relevant/corresponding region or portion of the reference molecule to which it shares homology. A SLAT or IP3R1 sequence, or a subsequence, variant or derivative, or polymorphism with substantial homology has or is predicted to have at least partial activity or function as the reference sequence.

The extent of identity (homology) between two sequences can be ascertained using a computer program and mathematical algorithm known in the art. Such algorithms that calculate percent sequence identity (homology) generally account for sequence gaps and mismatches over the comparison region or area. For example, a BLAST (e.g., BLAST 2.0) search algorithm (see, e.g., Altschul et al., J. Mol. Biol. 215:403 (1990), publicly available through NCBI) has exemplary search parameters as follows: Mismatch −2; gap open 5; gap extension 2. For polypeptide sequence comparisons, a BLASTP algorithm is typically used in combination with a scoring matrix, such as PAM100, PAM 250, BLOSUM 62 or BLOSUM 50. FASTA (e.g., FASTA2 and FASTA3) and SSEARCH sequence comparison programs are also used to quantitate extent of identity (Pearson et al., Proc. Natl. Acad. Sci. USA 85:2444 (1988); Pearson, Methods Mol. Biol. 132:185 (2000); and Smith et al., J. Mol. Biol. 147:195 (1981)). Programs for quantitating protein structural similarity using Delaunay-based topological mapping have also been developed (Bostick et al., Biochem Biophys Res Commun. 304:320 (2003)).

Variant and derivative polypeptides include, for example, non-conservative and conservative substitutions of SLAT and/or IP3R1 sequences. In particular embodiments, a variant protein has one or a few (e.g., 1-5%, 5-10%, 10-20%) of the residues of total protein length, or 1-2, 2-3, 3-4, 5-10, 10-20, 20-50 residues substituted, with conservative or non-conservative substitutions or conservative and non-conservative amino acid substitutions. A "conservative substitution" denotes the replacement of an amino acid residue by another, chemically or biologically similar residue. Biologically similar means that the substitution does not destroy a biological activity or function. Structurally similar means that the amino acids have side chains with similar length, such as alanine, glycine and serine, or a similar size. Chemical similarity means that the residues have the same charge or are both hydrophilic or hydrophobic.

Particular examples of conservative substitutions include the substitution of a hydrophobic residue such as isoleucine, valine, leucine or methionine for another, the substitution of a polar residue for another, such as the substitution of arginine for lysine, glutamic for aspartic acids, or glutamine for asparagine, and the like. A "conservative substitution" also includes the use of a substituted amino acid in place of an unsubstituted parent amino acid.

Variant and derivative proteins also include one or more D-amino acids substituted for L-amino acids (and mixtures thereof), structural and functional analogues, for example, peptidomimetics having synthetic or non-natural amino acids or amino acid analogues and derivatized forms. Variant and derivative proteins further include "chemical derivatives," in which one or more amino acids has have a side chain chemically altered or derivatized. Such derivatized polypeptides include, for example, amino acids in which free amino groups form amine hydrochlorides, p-toluene sulfonyl groups, carobenzoxy groups; the free carboxy groups form salts, methyl and ethyl esters; free hydroxl groups that form O-acyl or O-alkyl derivatives as well as naturally occurring amino acid derivatives, for example, 4-hydroxyproline, for proline, 5-hydroxylysine for lysine, homoserine for serine, ornithine for lysine etc. Also included are amino acid derivatives that can alter covalent bonding, for example, the disulfide linkage that forms between two cysteine residues that produces a cyclized polypeptide.

Additions and insertions include, for example, heterologous domains. A heterologous domain refers to one or more regions or portions that are derived from, obtained or isolated from, or based upon other physical or chemical entities. That is, for example, one portion of the fusion or chimera, such as SLAT or IP3R1, includes or consists of a region or portion that does not exist together in nature, and is structurally distinct.

An addition (e.g., heterologous domain) can be a covalent or non-covalent attachment of any type of molecule to a composition, such as a protein (e.g. SLAT or IP3R1) or other chemical entity (e.g. organic or inorganic compound). Typically additions and insertions (e.g., a heterologous domain) confer a complementary or a distinct function or activity.

Additions and insertions include chimeric and fusion sequences, which is a protein sequence having one or more molecules not normally present in a reference native wild type sequence covalently attached to the sequence. The terms "fusion" or "chimeric" and grammatical variations thereof, when used in reference to a molecule, such as SLAT or IP3R1, means that a portions or part of the molecule contains a different entity distinct (heterologous) from the molecule (e.g., SLAT or IP3R1) as they do not typically exist together in nature. A particular example is a molecule, such as amino acid residues or a polypeptide sequence of another protein (e.g., cell targeting or penetrating moiety or protein such as HIV tat, or immunoglobulin such as an Fc domain, or antibody)) attached to SLAT or IP3R1 subsequence to produce a chimera, or a chimeric polypeptide, to impart a distinct function (e.g., increased cell penetration, increased stability and/or half-life, etc.).

In particular embodiments, additions and insertions include a cell-penetrating moiety (CPM), or a cell-penetrating peptide (CPP). As used herein, a "cell-penetrating moiety (CPM)" is a molecule that penetrates or passes through cell membranes, typically without a need for binding to a cell membrane receptor. A cell penetrating peptide (CPP) can penetrate membranes, and is typically a peptide sequence of less that 25-50 (more typically, 30) amino acid residues in length. In particular non-limiting aspects, a CPM or CPP includes HIV Tat, *Drosophila antennapedia* (RQIKIWFQNRRMKWKK, SEQ ID NO:5), polyarginine (RRRRRRRRR, SEQ ID NO6), polylysine (KKKKKKKKK, SEQ ID NO:7), PTD-5 (RRQRRTSKLMKR, SEQ ID NO:8), or a Transportan (GWTLNSAGYLLGKINLKA-LAALAKKIL, SEQ ID NO:9), or KALA (WEAKLAKA-LAKALAKHLAKALAKALKACEA, SEQ ID NO:10) sequence.

Linkers, such as amino acid(s) or peptidomimetic sequences may be inserted between the sequence and the addition (e.g., heterologous domain) so that the two entities maintain, at least in part, a distinct function or activity. Linkers may have one or more properties that include a flexible conformation, an inability to form an ordered secondary structure or a hydrophobic or charged character, which could promote or interact with either domain. Amino acids typically found in flexible protein regions include Gly, Asn and Ser. Other near neutral amino acids, such as Thr and Ala, may also be used in the linker sequence. The length of the linker sequence may vary without significantly affecting a function or activity of the fusion protein (see, e.g., U.S. Pat. No. 6,087,329). Linkers further include chemical moieties and conjugating agents, such as sulfo-succinimidyl derivatives (sulfo-SMCC, sulfo-SMPB), disuccinimidyl suberate (DSS), disuccinimidyl glutarate (DSG) and disuccinimidyl tartrate (DST).

Additions and insertions further include labels, tags or detectable moieties, which can be used to provide a means of isolation or identification, or that is useful for detection the tagged entity (e.g., SLAT or IP3R1 sequence). A detectable label can be attached (e.g., linked or conjugated), for example, to a SLAT or IP3R1 sequence, or be within or comprise one or more atoms that comprise the molecule. If necessary, additional reagents can be used in combination with the detectable moieties to provide or enhance the detection signal.

Non-limiting exemplary detectable labels also include a radioactive material, such as a radioisotope, a metal or a metal oxide. Radioisotopes include radionuclides emitting alpha, beta or gamma radiation. In particular embodiments, a radioisotope can be one or more of: $^{3}$H, $^{10}$B, $^{18}$F, $^{11}$C, $^{14}$C, $^{13}$N, $^{18}$O, $^{15}$O, $^{32}$P, P$^{33}$, $^{35}$S, $^{35}$Cl, $^{45}$Ti, $^{46}$Sc, $^{47}$Sc, $^{51}$Cr, $^{52}$Fe, $^{59}$Fe, $^{57}$Co, $^{60}$Cu, $^{61}$Cu, $^{62}$Cu, $^{64}$Cu, $^{67}$Cu, $^{67}$Ga, $^{68}$Ga, $^{72}$As, $^{76}$Br, $^{77}$Br, $^{81m}$Kr, $^{82}$Rb, $^{85}$Sr, $^{89}$Sr, $^{86}$Y, $^{90}$Y, $^{95}$Nb, $^{94m}$Tc, $^{99m}$Tc, $^{97}$Ru, $^{103}$Ru, $^{105}$Rh, $^{109}$Cd, $^{111}$In, $^{113}$Sn, $^{113m}$In, $^{114}$In, I$^{125}$, I$^{131}$, $^{140}$La, $^{141}$Ce, $^{149}$Pm, $^{153}$Gd, $^{157}$Gd, $^{153}$Sm, $^{161}$Tb, $^{166}$Dy, $^{166}$Ho, $^{169}$Er, $^{169}$Y, $^{175}$Yb, $^{177}$Lu, $^{186}$Re, $^{188}$Re, $^{201}$Tl, $^{203}$Pb, $^{211}$At, $^{212}$Bi or $^{225}$Ac.

Additional non-limiting exemplary detectable labels include a metal or a metal oxide. In particular embodiments, a metal or metal oxide is one or more of: gold, silver, copper, boron, manganese, gadolinium, iron, chromium, barium, europium, erbium, praseodynium, indium, or technetium. In additional embodiments, a metal oxide includes one or more of: Gd(III), Mn(II), Mn(III), Cr(II), Cr(III), Cu(II), Fe(III), Pr(III), Nd(III) Sm(III), Tb(III), Yb(III) Dy(III), Ho(III), Eu(II), Eu(III), or Er(III).

Further non-limiting exemplary detectable labels include contrast agents (e.g., gadolinium; manganese; barium sulfate; an iodinated or noniodinated agent; an ionic agent or nonionic agent); magnetic and paramagnetic agents (e.g., iron-oxide chelate); nanoparticles; an enzyme (horseradish peroxidase, alkaline phosphatase, β-galactosidase, or acetylcholinesterase); a prosthetic group (e.g., streptavidin/ biotin and avidin/biotin); a fluorescent material (e.g., umbelliferone, fluorescein, fluorescein isothiocyanate, rhodamine, dichlorotriazinylamine fluorescein, dansyl chloride or phycoerythrin); a luminescent material (e.g., luminol); or a bioluminescent material (e.g., luciferase, luciferin, aequorin).

Additional non-limiting examples of tags and/or detectable labels include enzymes (horseradish peroxidase, urease, catalase, alkaline phosphatase, beta-galactosidase, chloramphenicol transferase); enzyme substrates; ligands (e.g., biotin); receptors (avidin); GST-, T7-, His-, myc-, HA- and FLAG-tags; electron-dense reagents; energy transfer molecules; paramagnetic labels; fluorophores (fluorescein, fluorscamine, rhodamine, phycoerthrin, phycocyanin, allophycocyanin); chromophores; chemi-luminescent (imidazole, luciferase, acridinium, oxalate); and bio-luminescent agents.

As set forth herein, a detectable label or tag can be linked or conjugated (e.g., covalently) to the agent (e.g., SLAT or IP3R1 polypeptide, peptide, fragment, or antibody that binds to SLAT or IP3R1). In various embodiments a detectable label, such as a radionuclide or metal or metal oxide can be bound or conjugated to the agent, either directly or indirectly. A linker or an intermediary functional group can be used to link the molecule to a detectable label or tag. Linkers include amino acid or peptidomimetic sequences inserted between the agent and a label or tag so that the two entities maintain, at least in part, a distinct function or activity. Linkers may have one or more properties that include a flexible conformation, an inability to form an ordered secondary structure or a hydrophobic or charged character which could promote or interact with either domain. Amino acids typically found in flexible protein regions include Gly, Asn and Ser. The length of the linker sequence may vary without significantly affecting a function or activity.

Linkers further include chemical moieties, conjugating agents, and intermediary functional groups. Examples include moieties that react with free or semi-free amines, oxygen, sulfur, hydroxy or carboxy groups. Such functional groups therefore include mono and bifunctional crosslinkers, such as sulfo-succinimidyl derivatives (sulfo-SMCC, sulfo-SMPB), in particular, disuccinimidyl suberate (DSS), BS3 (Sulfo-DSS), disuccinimidyl glutarate (DSG) and disuccinimidyl tartrate (DST). Non-limiting examples include diethylenetriaminepentaacetic acid (DTPA) and ethylene diaminetetracetic acid.

Invention agents that modulate binding between SLAT and IP3R1, or modulate an immune response, or modulate activation of CD4+ T cells can be introduced into cells via various techniques.

A cell into which a nucleic acid or protein has been introduced is referred to as a "transduced cell." For example, in a cell having a polynucleotide, the polynucleotide has been introduced/transferred, "transduction" or "transfection" of the cell. Accordingly, a "transduced" cell (e.g., in a mammal, such as a cell or tissue or organ cell), means a change in a cell following incorporation of an exogenous molecule, for example, a protein or polynucleotide into the cell. The term "transfect" typically refers to introduction of a polynucleotide into a cell or host organism, e.g., a genetic change. The cell(s) can be propagated and the introduced protein expressed, or nucleic acid transcribed and optionally translated. For invention methods and uses, a transduced or transfected cell can be in a subject.

A polynucleotide introduced into a cell may or may not be integrated into nucleic acid of the recipient cell. If an introduced polynucleotide becomes integrated into the nucleic acid (genomic DNA) of the recipient cell it can be stably maintained in that cell and further passed on to or inherited by progeny cells or organisms of the recipient cell or organism. Finally, the introduced nucleic acid may exist in the recipient cell (or host organism) as an episome or even only transiently.

The term "vector" refers to a plasmid, virus or other vehicle that can be manipulated by insertion or incorporation of a polynucleotide. Such vectors can be used for genetic manipulation (i.e., "cloning vectors"), to introduce/transfer polynucleotides into cells, and to provide, transcribe or translate the inserted polynucleotide in cells. A vector nucleic acid sequence generally contains elements, such as a polynucleotide, expression control element and other sequences positioned 5' or 3' of a polynucleotide, or an intron.

As disclosed herein, vectors and other delivery vehicles may be used to introduce the agents set forth herein into cells, e.g., cells of a subject. Non-limiting examples include virus vectors, liposomes and particles, such as nanoparticles.

Viral vectors such as lend- and parvo-virus vectors, including AAV vectors provide a means for delivery of polynucleotide sequences into cells ex vivo, in vitro and in vivo. The introduced polynucleotide can encode proteins or provide or be transcribed into inhibitory nucleic acids. For example, a recombinant AAV vector can include a polynucleotide encoding a SLAT and/or IP3R1 peptide or fragment. Vector delivery or administration to a subject (e.g., mammal) therefore provides encoded proteins/peptides and inhibitory nucleic acid to the cell, e.g. of a subject. Thus, viral vectors such as lend- and parvo-virus vectors, including AAV vectors, can be used to transfer/deliver polynucleotides, such as a polynucleotide encoding a protein/peptide, into a cell of a subject, optionally for modulating an immune response, and/or modulating activation of CD4+ T cells, and/or treating a variety of diseases.

In particular embodiments, the agents comprise liposomes. As used herein, a "liposome" refers to a generally spherical vesicle generally comprised of amphipathic molecules (e.g., having both a hydrophobic (nonpolar) portion and a hydrophilic (polar) portion). Typically, the liposome can be produced as a single (unilamellar) closed bilayer or a multicompartment (multilamellar) closed bilayer. The liposome can be formed by natural lipids, synthetic lipids, or a combination thereof. In a preferred embodiment, the liposome comprises one or more phospholipids. Lipids known in the art for forming liposomes include, but are not limited to, lecithin (soy or egg; phosphatidylcholine), dipalmitoylphosphatidylcholine, dimyristoylphosphatidylcholine, distearoylphosphatidylcholine, dicetylphosphate, phosphatidylglycerol, hydrogenated phosphatidylcholine, phosphatidic acid, cholesterol, phosphatidylinositol, a glycolipid, phosphatidylethanolamine, phosphatidylserine, a maleimidyl-derivatized phospholipid (e.g., N-[4(p-maleimidophenyhbutyryl]phosphatidylethanolamine), dioleylphosphatidylcholine, dipalmitoylphosphatidylglycerol, dimyristoylphosphatidic acid, and a combination thereof. Invention compositions include liposomes formulated with agents, methods to deliver the agents to cells, methods of modulating an immune response, methods of modulating activation or differentiation of CD4+ T cells, and methods of treatment as set forth herein.

Nanoparticles include a matrix of polymers. In general, a "nanoparticle" refers to a polymer particle having a diameter of less than 1000 nm. A characteristic dimension of a particle is the diameter of a sphere having the same volume as the particle. For example, a characteristic dimension of the particle may be less than about 500 nm, less than about 400 nm, less than about 300 nm, less than about 200 nm, less than about 150 nm, less than about 100 nm, less than about 50 nm, less than about 30 nm, less than about 10 nm, less than about 3 nm, or less than about 1 nm in some cases.

An agent can be associated with the polymer matrix. An agent can be associated with the surface of, encapsulated within, surrounded by, and/or dispersed throughout the polymeric matrix. Optionally, a cell-penetrating or cell-targeting moiety can be covalently associated with the surface of a polymeric matrix. Covalent association of the agent and/or cell-penetrating or cell-targeting moiety can optionally be mediated by a linker.

A "polymer," as used herein is a molecular structure comprising one or more repeat units (monomers), connected by covalent bonds. The repeat units may all be identical, or in some cases, there may be more than one type of repeat unit present within a polymer. Polymers may be homopolymers or copolymers comprising two or more monomers. In terms of sequence, copolymers may be random, block, or comprise a combination of random and block sequences. If more than one type of repeat unit is present within the polymer, then the polymer is said to be a "copolymer."

A wide variety of polymers and methods for forming nanoparticles therefrom are known. In some embodiments, the matrix of a particle comprises one or more polymers. Any polymer may be used in accordance with the invention. Typically, polymers in are organic polymers. Polymers may be natural or unnatural (synthetic) polymers. In some embodiments, the polymer is biologically derived, i.e., a biopolymer.

In some embodiments, the polymer (e.g., copolymer, block copolymer) is amphiphilic, i.e., having a hydrophilic portion and a hydrophobic portion, or a relatively hydrophilic portion and a relatively hydrophobic portion. A hydrophilic polymer generally attracts water and a hydrophobic polymer generally repels water. In some cases, the hydrophilicity of two or more polymers may be different from each other, i.e., a first polymer may be more hydrophilic than a second polymer.

Expression of an operably linked polynucleotide is at least in part controllable by an expression control element such that the element modulates transcription of the polynucleotide and, as appropriate, translation of the transcript. A specific example of an expression control element is a promoter, which is usually located 5' of the transcribed polynucleotide sequence. Another example of an expression control element is an enhancer, which can be located 5', 3' of the transcribed sequence, or within the transcribed sequence.

A "promoter" as used herein can refer to a nucleic acid (e.g., DNA) sequence that is located adjacent to a polynucleotide sequence that is transcribed into an inhibitory nucleic acid or encodes a protein. A promoter is typically operatively linked to an adjacent sequence, e.g., heterologous polynucleotide. A promoter typically increases an amount expressed from a heterologous polynucleotide as compared to an amount expressed when no promoter exists.

An "enhancer" as used herein can refer to a sequence that is located adjacent to the heterologous polynucleotide. Enhancer elements are typically located upstream of a promoter element but also function and can be located downstream of or within a DNA sequence (e.g., a heterologous polynucleotide). Hence, an enhancer element can be located 100 base pairs, 200 base pairs, or 300 or more base pairs upstream or downstream of a heterologous polynucleotide.

Expression control elements (e.g., promoters) include those active in a particular tissue or cell type, referred to herein as a "tissue-specific expression control elements/promoters." Tissue-specific expression control elements are typically active in specific cell or tissue (e.g., immune cells such as T cells, etc.). Expression control elements are typically active in these cells, tissues or organs because they are recognized by transcriptional activator proteins, or other regulators of transcription, that are unique to a specific cell, tissue or organ type.

Expression control elements also include ubiquitous or promiscuous promoters/enhancers which are capable of driving expression of a polynucleotide in many different cell types. Such elements include, but are not limited to viral promoters/enhancers active in a variety of mammalian cell types such as cytomegalovirus (CMV) immediate early promoter/enhancer sequences, and Rous sarcoma virus (RSV) promoter/enhancer sequences (see, e.g., Boshart et al, *Cell*, 41:521-530 (1985)), the SV40 promoter. Such elements also include the dihydrofolate reductase promoter, the cytoplasmic β-actin promoter and the phosphoglycerol kinase (PGK) promoter.

Expression control elements also can confer expression in a manner that is regulatable, that is, a signal or stimuli increases or decreases expression of the operably linked heterologous polynucleotide. A regulatable element that increases expression of the operably linked polynucleotide in response to a signal or stimuli is also referred to as an "inducible element" (i.e., is induced by a signal) or a "de-repressible element," which is activated upon withdrawal of a signal or stimuli (i.e., the signal decreases expression such that when the signal is removed or absent, expression is increased). Particular examples include, but are not limited to, a hormone (e.g., steroid) inducible promoter. Typically, the amount of increase or decrease conferred by such elements is proportional to the amount of signal or stimuli present; the greater the amount of signal or stimuli, the greater the increase or decrease in expression.

As used herein, the term "operable linkage" or "operably linked" refers to a physical or functional juxtaposition of the components so described as to permit them to function in their intended manner. In the example of an expression control element in operable linkage with a nucleic acid, the relationship is such that the control element modulates expression of the nucleic acid. More specifically, for example, two DNA sequences operably linked means that the two DNAs are arranged (cis or trans) in such a relationship that at least one of the DNA sequences is able to exert a physiological effect upon the other sequence.

Undesirable or aberrant immune responses, inflammatory responses, or inflammation are characterized by many different physiological adverse symptoms or complications, which can be humoral, cell-mediated or a combination thereof. Responses, disorders and diseases that can be treated in accordance with embodiments herein include, but are not limited to, those that either directly or indirectly lead to or cause cell or tissue/organ damage in a subject. At the whole body, regional or local level, an immune response, inflammatory response, or inflammation can be characterized by swelling, pain, headache, fever, nausea, skeletal joint stiffness or lack of mobility, rash, redness or other discoloration. At the cellular level, an immune response, inflammatory response, or inflammation can be characterized by one or more of T cell activation and/or differentiation, cell infiltration of the region, production of antibodies, production of cytokines, lymphokines, chemokines, interferons and interleukins, cell growth and maturation factors (e.g., proliferation and differentiation factors), cell accumulation or migration and cell, tissue or organ damage. Thus, methods and uses include treatment of and an ameliorative effect upon any such physiological symptoms or cellular or biological responses characteristic of immune responses, inflammatory response, or inflammation.

Autoimmune responses, disorders and diseases are generally characterized as an undesirable or aberrant response, activity or function of the immune system characterized by increased or undesirable humoral or cell-mediated immune responsiveness or memory, or decreased or insufficient tolerance to self-antigens. Autoimmune responses, disorders and diseases that may be treated in accordance with embodiments herein include but are not limited to responses, disorders and diseases that cause cell or tissue/organ damage in the subject. The terms "immune disorder" and "immune disease" mean an immune function or activity, which is characterized by different physiological symptoms or abnormalities, depending upon the disorder or disease.

In another embodiment, the method comprises decreasing, reducing, inhibiting, suppressing, limiting or controlling an undesirable or aberrant immune response, disorder or disease, an inflammatory response, disorder or disease, inflammation, or an autoimmune response, disorder or disease, or an adverse symptom of an undesirable or aberrant immune response, disorder or disease, an inflammatory response, disorder or disease, inflammation, or an autoimmune response, disorder or disease. In particular aspects, the method comprises increasing, stimulating, enhancing, promoting, inducing or activating an immune response, inflammatory response or inflammation.

In another embodiment, the invention provides for a method of modulating activation or differentiation of CD4+ T cells in a subject comprising administering an agent that modulates binding of SLAT to IP3R1 thereby modulating activation or differentiation of CD4+ T cells in the subject.

In further embodiments, the invention provides for a method of modulating an immune response in a subject comprising administering an agent that modulates binding of SLAT to IP3R1 thereby modulating the immune response in the subject. In particular aspects, the subject has or has had an undesirable or aberrant immune response, disorder or disease, an inflammatory response, disorder or disease, inflammation, or an autoimmune response, disorder or disease or an adverse symptom of an undesirable or aberrant immune response, disorder or disease, an inflammatory response, disorder or disease, inflammation, or an autoimmune response, disorder or disease. In further aspects, the subject is in need of treatment for an undesirable or aberrant immune response, disorder or disease, an inflammatory response, disorder or disease, inflammation, or an autoimmune response, disorder or disease or an adverse symptom of an undesirable or aberrant immune response, disorder or disease, an inflammatory response, disorder or disease, inflammation, or an autoimmune response, disorder or disease. In additional aspects, the subject is at risk of an undesirable or aberrant immune response, disorder or disease, an inflammatory response, disorder or disease, inflammation, or an autoimmune response, disorder or disease or an adverse symptom of an undesirable or aberrant immune response, disorder or disease, an inflammatory response, disorder or disease, inflammation, or an autoimmune response, disorder or disease. In further aspects, the undesirable or aberrant immune response, disorder or disease, inflammatory response, disorder or disease, inflammation, or autoimmune response, disorder or disease comprises rheumatoid arthritis, juvenile rheumatoid arthritis, osteoarthritis, psoriatic arthritis, multiple sclerosis (MS), encephalomyelitis, myasthenia gravis, systemic lupus erythematosus (SLE), asthma, allergic asthma, autoimmune thyroiditis, atopic dermatitis, eczematous dermatitis, psoriasis, Sjögren's Syndrome, Crohn's disease, aphthous ulcer, iritis, conjunctivitis, keratoconjunctivitis, ulcerative colitis (UC), inflammatory bowel disease (IBD), cutaneous lupus erythematosus, scleroderma, vaginitis, proctitis, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, interstitial lung fibrosis, Hashimoto's thyroiditis, autoimmune polyglandular syndrome, insulin-dependent diabetes mellitus (IDDM, type I diabetes), insulin-resistant diabetes mellitus (type 2 diabetes), immune-mediated infertility, autoimmune Addison's disease, pemphigus vulgaris, pemphigus foliaceus, dermatitis herpetiformis, autoimmune alopecia, vitiligo, autoimmune hemolytic anemia, autoimmune thrombocytopenic purpura, pernicious anemia, Guillain-Barre syndrome, stiff-man syndrome, acute rheumatic fever, sympathetic ophthalmia, Goodpasture's syndrome, systemic necrotizing vasculitis, antiphospholipid syndrome or an allergy, Behcet's disease, severe combined immunodeficiency (SCID), recombinase activating gene (RAG 1/2) deficiency, adenosine deaminase (ADA) deficiency, interleukin receptor common_chain (_c) deficiency, Janus-associated kinase 3 (JAK3) deficiency and reticular dysgenesis; primary T cell immunodeficiency such as DiGeorge syndrome, Nude syndrome, T cell receptor deficiency, MHC class II deficiency, T AP-2 deficiency (MHC class I deficiency), ZAP70 tyrosine kinase deficiency and purine nucleotide phosphorylase (PNP) deficiency, antibody deficiencies, X-linked agammaglobulinemia (Bruton's tyrosine kinase deficiency), autosomal recessive agammaglobulinemia, Mu heavy chain deficiency, surrogate light chain (_5/14 0.1) deficiency, Hyper-lgM syndrome: X-linked (CD40 ligand deficiency) ornon-X-linked, Ig heavy chain gene deletion, IgA deficiency, deficiency of IgG subclasses (with or without IgA deficiency), common variable immunodeficiency (CVID), antibody deficiency with normal immunoglobulins; transient hypogammaglobulinemia of infancy, interferon_receptor (IFNGR1, IFNGR2) deficiency, interleukin 12 or interleukin 12 receptor deficiency, immunodeficiency with thymoma, Wiskott-Aldrich syndrome (WAS protein deficiency), ataxia telangiectasia (ATM deficiency), X-linked lymphoproliferative syndrome (SH2D1A/SAP deficiency), hyper IgE syndrome or Graft vs. Host Disease (GVHD). In further aspects, the immune response or inflammatory response is an anti-cancer or anti-pathogen immune response or inflammatory response. In further aspects, the subject is a mammal or a human.

Agents as set forth herein, such as small molecules, nucleic acids, vectors (e.g., viral vectors) proteins and other compositions, agents, drugs, biologics (proteins) can be incorporated into pharmaceutical compositions, e.g., a pharmaceutically acceptable carrier or excipient. Such pharmaceutical compositions are useful for, among other things, administration and delivery to a subject in vivo or ex vivo.

As used herein the terms "pharmaceutically acceptable" and "physiologically acceptable" mean a biologically acceptable formulation, gaseous, liquid or solid, or mixture thereof, which is typically suitable for one or more routes of administration, in vivo delivery or contact. A "pharmaceutically acceptable" or "physiologically acceptable" composition is a material that is not biologically or otherwise undesirable, e.g., the material may be administered to a subject without causing substantial undesirable biological effects. Thus, such a pharmaceutical composition may be used, for example, in administering an agent to a subject.

Such compositions include solvents (aqueous or non-aqueous), solutions (aqueous or non-aqueous), emulsions (e.g., oil-in-water or water-in-oil), suspensions, syrups, elixirs, dispersion and suspension media, coatings, isotonic and absorption promoting or delaying agents, compatible with pharmaceutical administration or in vivo contact or delivery. Aqueous and non-aqueous solvents, solutions and suspensions may include suspending agents and thickening agents. Such pharmaceutically acceptable carriers include tablets (coated or uncoated), capsules (hard or soft), microbeads, powder, granules and crystals. Supplementary active compounds (e.g., preservatives, antibacterial, antiviral and antifungal agents) can also be incorporated into the compositions.

Pharmaceutical compositions can be formulated to be compatible with a particular route of administration or delivery, as set forth herein or known to one of skill in the art. Thus, pharmaceutical compositions include carriers, diluents, or excipients suitable for administration by various routes.

Compositions suitable for parenteral administration comprise aqueous and non-aqueous solutions, suspensions or emulsions of the active compound, which preparations are typically sterile and can be isotonic with the blood of the intended recipient. Non-limiting illustrative examples include water, saline, dextrose, fructose, ethanol, animal, vegetable or synthetic oils.

Cosolvents and adjuvants may be added to the formulation. Non-limiting examples of cosolvents contain hydroxyl groups or other polar groups, for example, alcohols, such as isopropyl alcohol; glycols, such as propylene glycol, polyethyleneglycol, polypropylene glycol, glycol ether; glycerol; polyoxyethylene alcohols and polyoxyethylene fatty acid esters. Adjuvants include, for example, surfactants such as, soya lecithin and oleic acid; sorbitan esters such as sorbitan trioleate; and polyvinylpyrrolidone.

Pharmaceutical compositions and delivery systems appropriate for the compositions, methods and uses of the invention are known in the art (see, e.g., *Remington: The Science and Practice of Pharmacy* (2003) 20th ed., Mack Publishing Co., Easton, Pa.; *Remington's Pharmaceutical Sciences* (1990) 18th ed., Mack Publishing Co., Easton, Pa.; *The Merck Index* (1996) 12th ed., Merck Publishing Group, Whitehouse, N.J.; *Pharmaceutical Principles of Solid Dosage Forms* (1993), Technomic Publishing Co., Inc., Lancaster, Pa.; Ansel and Stoklosa, *Pharmaceutical Calculations* (2001) 11th ed., Lippincott Williams & Wilkins, Baltimore, Md.; and Poznansky et al., *Drug Delivery Systems* (1980), R. L. Juliano, ed., Oxford, N.Y., pp. 253-315).

Agents and pharmaceutical compositions as set forth herein can be packaged in unit dosage form (capsules, troches, cachets, lozenges, or tablets) for ease of administration and uniformity of dosage. "Unit dosage form" as used herein refers to physically discrete units suited as dosages for treatment or therapy. Each unit contains a predetermined quantity of agent in association with the pharmaceutical carrier (excipient, diluent, vehicle or filling agent) which, when administered in one or more doses, is calculated to produce a desired beneficial effect. Unit dosage forms also include, for example, ampules and vials, which may include a composition in a freeze-dried or lyophilized state; a sterile liquid carrier, for example, can be added prior to administration or delivery in vivo. Unit dosage forms additionally include, for example, ampules and vials with liquid compositions disposed therein. Unit dosage forms further include compositions for transdermal administration, such as "patches" adapted to remain in contact with the epidermis of the intended recipient for an extended or brief period of time. The individual unit dosage forms can be included in multi-dose kits or containers.

Dose amounts, frequency and duration for the agents, such as an agent that modulates binding of SLAT to IP3R1, can be can be empirically determined in appropriate animal models. Dose amounts, frequency and duration can also be determined and optimized in human clinical trials.

The dosage amount can range from about 0.0001 mg/kg of subject body weight/day to about 1,000.0 mg/kg of subject body weight/day. Of course, doses can be more or less, as appropriate, for example, 0.00001 mg/kg of subject body weight to about 10,000.0 mg/kg of subject body weight, about 0.001 mg/kg, to about 1,000 mg/kg, about 0.01 mg/kg, to about 100 mg/kg, or about 0.1 mg/kg, to about 10 mg/kg of subject body weight over a given time period, e.g., 1, 2, 3, 4, 5 or more hours, days, weeks, months, years, in single bolus or in divided/metered doses.

Of course, the dosage amount, frequency and duration can vary depending upon the judgment of the skilled artisan which will consider various factors such as whether the treatment is prophylactic or therapeutic, the type or severity of the condition, disorder or disease, the associated symptom to be treated, the clinical endpoint(s) desired such as the type and duration of beneficial or therapeutic effect. Additional non-limiting factors to consider in determining appropriate dosage amounts, frequency, and duration include previous or simultaneous treatments, potential adverse systemic, regional or local side effects, the individual subject (e.g., general health, age, gender, race, bioavailability), condition of the subject such as other disorders or diseases present and other treatments or therapies that the subject has or is undergoing (e.g., medical history). Dosage amount, frequency or duration can be increased, if necessary, or reduced, for example, once control of the condition, disorder or disease is achieved, dose amounts, frequency or duration can be reduced. The skilled artisan will appreciate the factors that may influence the dosage, frequency and duration required to provide an amount sufficient to provide a subject with a beneficial effect, such as a therapeutic benefit.

The invention provides kits and containers including agents suitable for packaging the agents and/or practicing the methods, treatment protocols or therapeutic regimes herein, and suitable packing material. In one embodiment, a kit includes an agent and instructions for administering or treatment of the agent. In another embodiment, a kit includes an agent, an article of manufacture for delivery of the agent to the target area, organ, tissue or system (e.g., locally, regionally or systemically to a subject) and instructions for administering the agent.

The term "packing material" refers to a physical structure housing an agent or a component of the kit. The material can maintain the components sterilely, and can be made of material commonly used for such purposes (e.g.). Containers include but are not limited to ampules, vials, tubes, syringes, injectors, etc. Kits and containers can be made of materials including, but not limited paper, corrugated fiber, glass, plastic, foil, polyethylene, polystyrene, polypropylene, polybutylene, and composites or combinations of such materials/polymers.

Kits and containers of the invention optionally include labels or inserts. Labels or inserts include "printed matter," e.g., paper or cardboard, or separate or affixed to a component, a kit or packing material (e.g., a box), or attached to an ampule, tube or vial containing a kit component. Labels or inserts can additionally include a computer readable medium, such as a disk (e.g., floppy diskette, ZIP disk), optical disk such as CD- or DVD-ROM/RAM, DVD, MP3, magnetic tape, or an electrical storage media such as RAM and ROM or hybrids of these such as magnetic/optical storage media, FLASH media or memory type cards.

Labels or inserts can include identifying information of one or more components therein (e.g., the binding agent or pharmaceutical composition), dose amounts, clinical pharmacology of the active agent(s) including mechanism of action, pharmacokinetics and pharmacodynamics. Labels or inserts can include information identifying manufacturer information, lot numbers, and location and date of manufacture.

Labels or inserts can include information on a condition, disorder or disease for which a kit component may be used. Labels or inserts can include instructions for the clinician or subject for using one or more of the kit components in a method, or treatment protocol or therapeutic regimen. Instructions can include dosage amounts, frequency or duration, and instructions for practicing any of the methods, treatment protocols or therapeutic regimes described herein.

Labels or inserts can include information on any benefit that a component may provide, such as a therapeutic benefit. Labels or inserts can include information on potential adverse side effects, such as warnings to the subject or clinician regarding situations where it would not be appropriate to use a particular agent. For example, adverse side effects are generally more likely to occur at higher dose amounts, frequency or duration of the agent and, therefore, instructions could include recommendations against higher dose amounts, frequency or duration. Adverse side effects could also occur when the subject has, will be or is currently taking one or more other medications that may be incompatible with the composition, or the subject has, will be or is currently undergoing another treatment protocol or therapeutic regimen which would be incompatible with the composition and, therefore, instructions could include information regarding such incompatibilities.

The invention provides methods of screening for an agent for binding of SLAT to IP3R1. In one embodiment, a method includes a) contacting SLAT with IP3R1 in the presence of a test agent under conditions allowing binding of SLAT to IP3R1; and b) determining if the test agent modulates binding of SLAT to IP3R1, wherein determination that the test agent modulates binding of SLAT to IP3R1 indicates that the test agent is an agent that modulates binding of SLAT to IP3R1.

The invention also provides methods of identifying an agent that modulates binding of SLAT to IP3R1. In one embodiment, a method includes a) contacting SLAT with IP3R1 in the presence a test agent under conditions allowing binding of SLAT to IP3R1; and b) determining if the test agent modulates binding of SLAT to IP3R1, wherein determination that the test agent modulates binding of SLAT to IP3R1 indicates that the test agent is an agent that modulates binding of SLAT to IP3R1.

In particular aspects, a method includes screening for or identifying an agent for decreasing, reducing, inhibiting, suppressing, limiting or controlling undesirable or aberrant immune response, disorder or disease, an inflammatory response, disorder or disease, inflammation, or an autoimmune response, disorder or disease. In further particular aspects, the contacting is in vivo or in vitro.

The terms "determining," "assaying" and "measuring" and grammatical variations thereof are used interchangeably herein and refer to either qualitative or quantitative determinations, or both qualitative and quantitative determinations. When the terms are used in reference to measurement or detection, any means of assessing the relative amount, including the various methods set forth herein and known in the art.

Unless otherwise defined, all technical and scientific terms used herein have the same meaning as commonly understood by one of ordinary skill in the art. Although methods and materials similar or equivalent to those described herein can be used in the practice or testing of the present embodiments, suitable methods and materials are described herein.

All applications, publications, patents and other references, GenBank citations and ATCC citations cited herein are incorporated by reference in their entirety. In case of conflict, the specification, including definitions, will control.

As used herein, the singular forms "a", "and," and "the" include plural referents unless the context clearly indicates otherwise. Thus, for example, reference to "a SLAT sequence" or "a IP3R1 sequence" includes a plurality of such SLAT or IP3R1 sequences, subsequences, variants and derivatives, polymorphisms, or combination compositions or pharmaceutical compositions, and reference to "a SLAT or IP3R1 activity or function" can include reference to one or more SLAT or IP3R1 activities or functions, and so forth.

As used herein, numerical values are often presented in a range format throughout this document. The use of a range format is merely for convenience and brevity and should not be construed as an inflexible limitation on the scope of the embodiments herein. Accordingly, the use of a range expressly includes all possible subranges, all individual numerical values within that range. Furthermore, all numerical values or numerical ranges include integers within such ranges and fractions of the values or the integers within ranges unless the context clearly indicates otherwise. This construction applies regardless of the breadth of the range and in all contexts throughout this patent document. Thus, for example, reference to a range of 90-100% includes 91-99%, 92-98%, 93-95%, 91-98%, 91-97%, 91-96%, 91-95%, 91-94%, 91-93%, and so forth. Reference to a range of 90-100%, includes 91%, 92%, 93%, 94%, 95%, 95%, 97%, etc., as well as 91.1%, 91.2%, 91.3%, 91.4%, 91.5%, etc., 92.1%, 92.2%, 92.3%, 92.4%, 92.5%, etc., and so forth.

In addition, reference to a range of 1-5,000 fold includes 1, 2, 3, 4, 5, 6, 7, 8, 9, 10, 11, 12, 13, 14, 15, 16, 17, 18, 19, 20, fold, etc., as well as 1.1, 1.2, 1.3, 1.4, 1.5, fold, etc., 2.1, 2.2, 2.3, 2.4, 2.5, fold, etc., and any numerical range within such a ranges, such as 1-2, 5-10, 10-50, 50-100, 100-500, 100-1000, 500-1000, 1000-2000, 1000-5000, etc.

As also used herein a series of range formats are used throughout this document. The use of a series of ranges includes combinations of the upper and lower ranges to provide a range. This construction applies regardless of the breadth of the range and in all contexts throughout this patent document. Thus, for example, reference to a series of ranges such as 5 to 10, 10 to 20, 20 to 30, 30, to 50, 50 to 100, 100 to 150, 150 to 200, 200 to 300, or 300 to 400, 400-500, 500-600, or 600-705, includes ranges such as 5-20, 5-30, 5-40, 5-50, 5-75, 5-100, 5-150, 5-171, and 10-30, 10-40, 10-50, 10-75, 10-100, 10-150, 10-171, and 20-40, 20-50, 20-75, 20-100, 20-150, 20-200, 50 to 200, 50 to 300, 50, to 400, 50 to 500, 100 to 300, 100 to 400, 100 to 500, 100 to 600, 200-400, 200-500, 200 to 600, 200 to 700, and so forth.

Embodiments herein are generally disclosed herein using affirmative language to describe the numerous embodiments. Embodiments herein also specifically include those in which particular subject matter is excluded, in full or in part, such as substances or materials, method steps and conditions, protocols, procedures, assays or analysis. Thus, even though embodiments herein are generally not expressed herein in terms of what they do not include aspects that are not expressly included in various embodiments are nevertheless disclosed herein.

A number of embodiments have been described. Nevertheless, it will be understood that various modifications may be made without departing from the spirit and scope of the embodiments. Accordingly, the following examples are intended to illustrate but not limit the scope of the embodiments described in the claims.

Embodiments herein are further exemplified by way of the following non-limited examples.

EXAMPLES

Example 1: TCR-Induced Association Between SLAT and the IP3R1

Figure 1B:
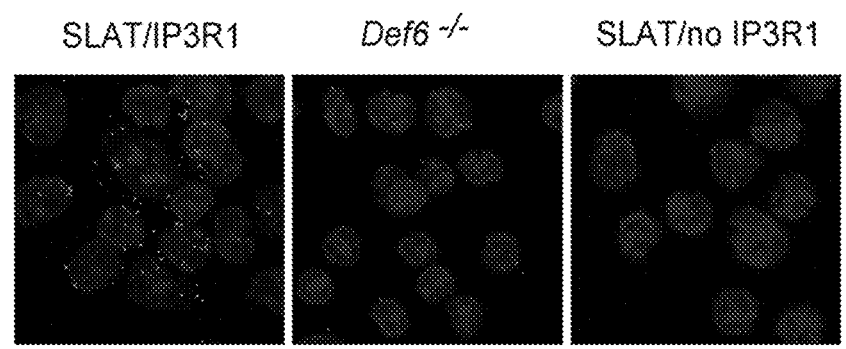
FIG. 1b WT or Def6–/– CD4+ T cells were adhered to poly-L-lysine coverslips, fixed, and stained with anti-SLAT and -IP3R1 Abs. Proximity of the molecules stained with each pair of Abs was then assessed using the Duolink technology. Background, non-specific signals were determined by performing the assay on Def6–/– CD4+ T cells, or by omitting the anti-IP3R1 antibody from WT T cells.
Figure 1C:
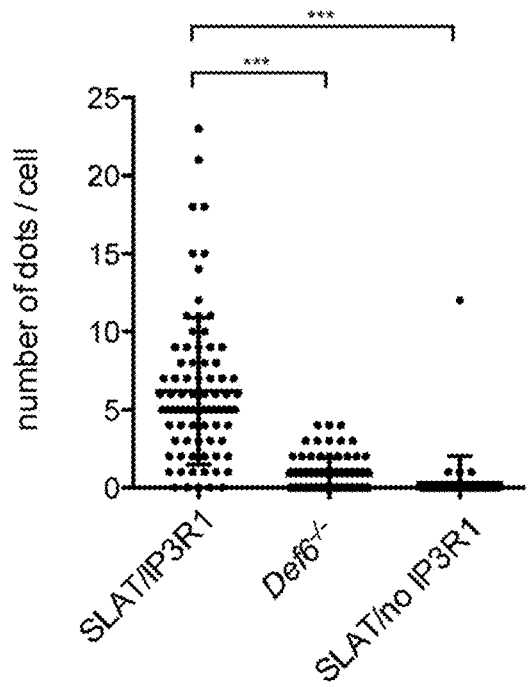
FIG. 1c Quantitation of spots indicative of molecular proximity. Number of spots/cell in different microscopy fields ±SD is plotted. Each dot represents a single cell. A total of 80 cells for the SLAT/IP3R1 and the Def6–/– conditions and a total of 49 cells for the SLAT/no IP3R1 condition were analyzed. Statistical differences were determined using a two-tailed Student's t test. ***, p<0.0001, WT vs. Def6–/– T cells (p<0.0001), and IP3R1/SLAT Abs vs. anti-SLAT Ab alone (p<0.0001).

Upon TCR stimulation, Def6−/− CD4+ T cells exhibited a profound defect in $Ca^{2+}$/NFAT signaling that was traced to a severe reduction in $Ca^{2+}$ release from ER stores (13). Given the intact production of IP3 by stimulated Def6−/− CD4+ T cells (13), it was hypothesized that SLAT participates in proper IP3R1 function in T lymphocytes, potentially via its physical interaction with the IP3R1. Using immunoprecipitation (IP) studies on anti-CD3/CD28-stimulated CD4+ T cells, it was found that within minutes after TCR engagement, endogenous SLAT interacted with IP3R1, peaking at two minutes post-stimulation and returning to its basal level after 15 minutes (FIG. 1a). Using an in situ Duolink proximity ligation assay (17), it was also demonstrated that there is a close proximity between SLAT and the IP3R1 in stimulated CD4+ T cells (FIG. 1b,c).

Figure 1D:
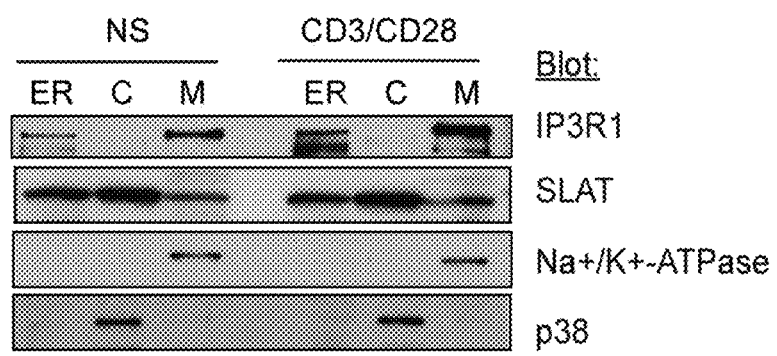
FIG. 1d Subcellular fractionation of MCC-T cells. Endoplasmic reticulum (ER), cytosolic (C) and membrane (M) fractions prepared from MCC-T cells stimulated with anti-CD3 plus-CD28 mAbs for 2 min were separated by SDS-PAGE and immunoblotted with the indicated Abs. Data shown are representative of at least 3 (FIG. 1a, FIG. 1d) or 2 (FIG. 1b, FIG. 1c) independent studies.

Upon TCR stimulation, SLAT translocates from the cytosol to the PM and the IS in a process dependent on phosphorylation of its ITAM-like motif (16). To determine whether SLAT and the IP3R1 are localized within the same cellular compartment in T cells, subcellular fractionation of MCC-T cells, an antigen-specific T cell hybridoma (18) was performed. It was found that SLAT resided in the cytosol and PM fractions but, in addition, it was also detected in the ER fraction, where IP3R1 was present (FIG. 1d). Thus, TCR stimulation induces an interaction between SLAT and the IP3R1 in CD4+ T cells, and both can be found in the ER.

Example 2: SLAT Directly Binds the IP3R1 LBD

Figure 2A:
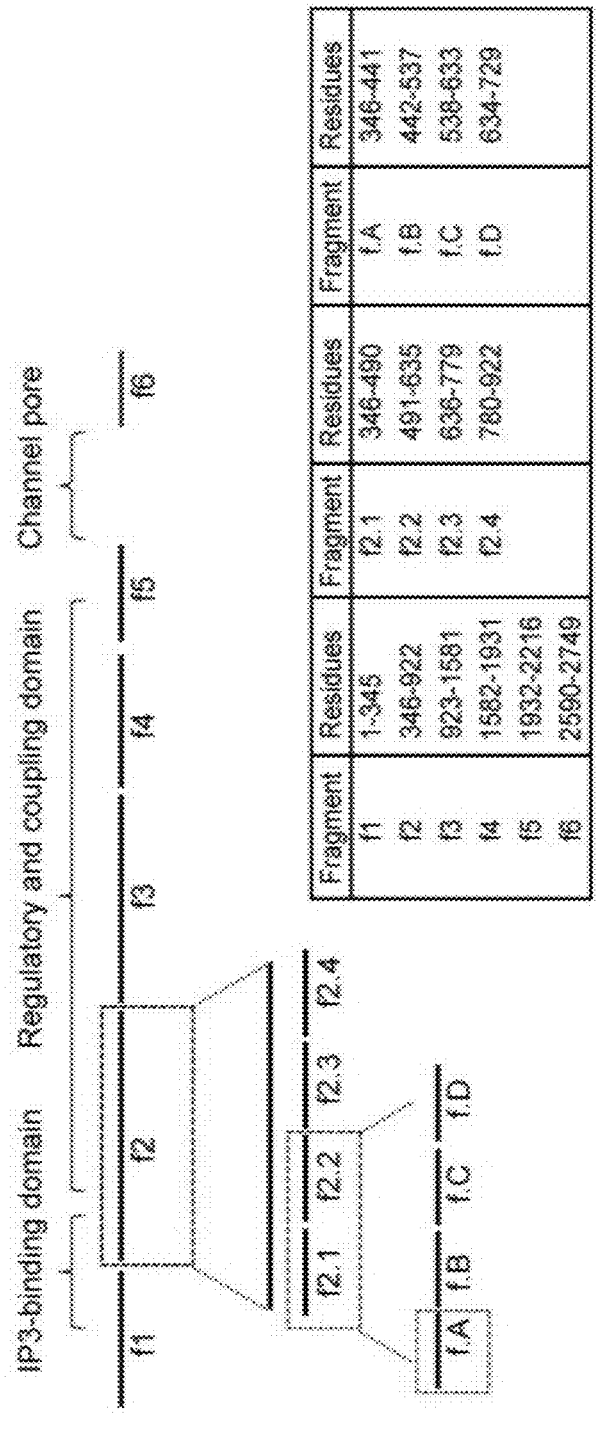
FIG. 2a Schematic representation of IP3R1 functional domains (without the channel pore), including the IP3 (ligand)-binding domain (LBD), the regulatory and coupling domains, and the C-terminal intracellular domain. The six fragments (f1-f6) used as initial baits in GST pull-down studies, as well as smaller fragments derived from f2 are indicated with numbering of the corresponding amino acid residues.
Figure 2B:
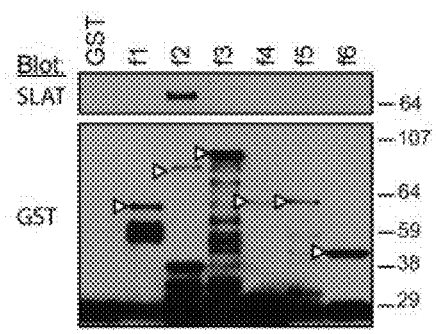
FIGS. 2b-2d Lysates of anti-CD3/CD28-stimulated MCC-T cells were pre-cleared and incubated with the indicated gluthatione-bound GST-IP3R1 fusion proteins for 1 h at 4° C. Eluted proteins were subjected to SDS-PAGE and immunoblotted with the indicated Abs. Arrowheads indicate the position of the GST-IP3R1 fusion proteins detected by an anti-GST immunoblot.
Figure 2C:
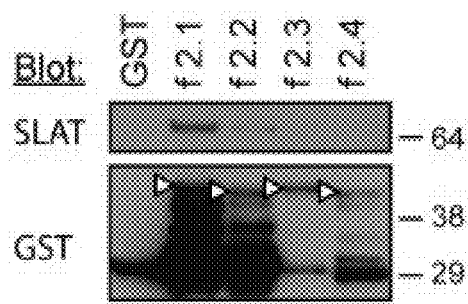
Figure 2D:
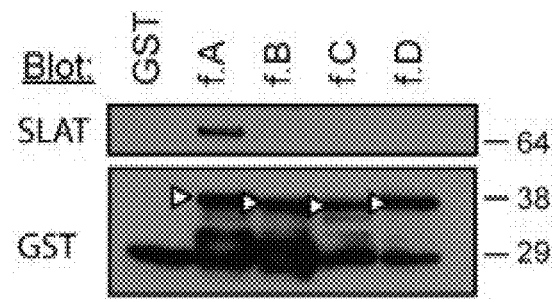

Each IP3R monomer comprises five distinct domains: An N-terminal IP3-binding domain, a central regulatory/coupling domain, a transmembrane channel, a gatekeeper domain and, finally, a short cytoplasmic C-terminal domain (19, 20). To map the SLAT-binding site in IP3R1, a series of GST-IP3R1 recombinant proteins (FIG. 2a) were used in pull-down studies. These proteins correspond to six fragments (f1-f6) covering the entire length of the IP3R1, with the exception of the transmembrane channel domain. SLAT interacted exclusively with the f2 protein corresponding to IP3R1 residues 346-922 (FIG. 2b), a region that overlaps the IP3-binding and the regulatory/coupling domains. To further narrow down the IP3R1 region responsible for SLAT binding, shorter (~140 residues) recombinant fragments (f2.1-f2.4) of f2 were generated (FIG. 2a) and it was found that SLAT was predominantly bound to fragment f2.1 (residues 346-490) and, to a much lesser extent, to fragment f2.2 (residues 491-635; FIG. 2c). Further division of these two fragments into shorter fragments of ~96 residues each (f.A-f.D) revealed that SLAT interacted substantially with one IP3R1 fragment, f.A, which corresponds to residues 366-441 (FIG. 2d), thereby defining a short SLAT-binding IP3R1 region within its LBD.

Figure 2E:
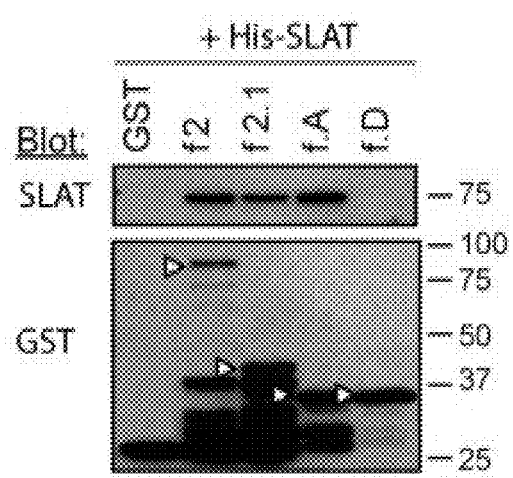
FIG. 2e Recombinant His-SLAT protein was incubated with the indicated immobilized GST-IP3R1 fusion proteins (or a control GST protein) as in (FIG. 2b-FIG. 2d), Eluted proteins were subjected to SDS-PAGE and immunoblotting. Data shown are representative of at least 3 independent studies.

To determine whether the SLAT-IP3R1 interaction is direct, pull-down studies were performed with various recombinant GST-IP3R1 proteins and purified SLAT. Recombinant SLAT, in the absence of any other accessory proteins, bound all IP3R1 fusion protein containing residues 366-441, i.e., f2, f2.1 and f.A, but not f.D (FIG. 2e), which served as a negative control, thus indicating that the association between SLAT and the IP3R1 is direct. Similarly, Farwestern blots using recombinant proteins also showed direct binding of SLAT to IP3R1 (FIG. 7).

Example 3: Independent Interaction of the SLAT PH and Putative EF-Hand Domains with IP3R1

Figure 3A:
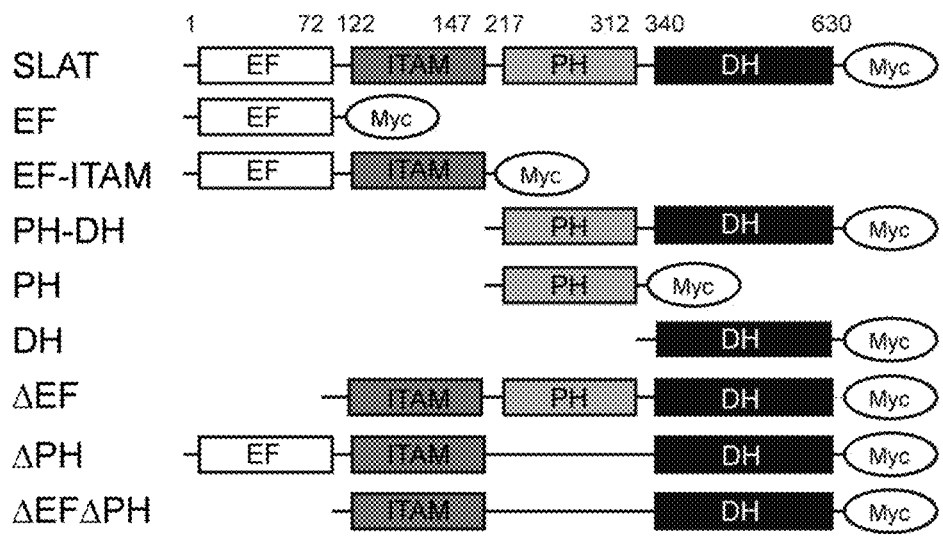
FIG. 3a Schematic representation of SLAT functional domains and SLAT mutants used in IP studies.
Figure 3B:
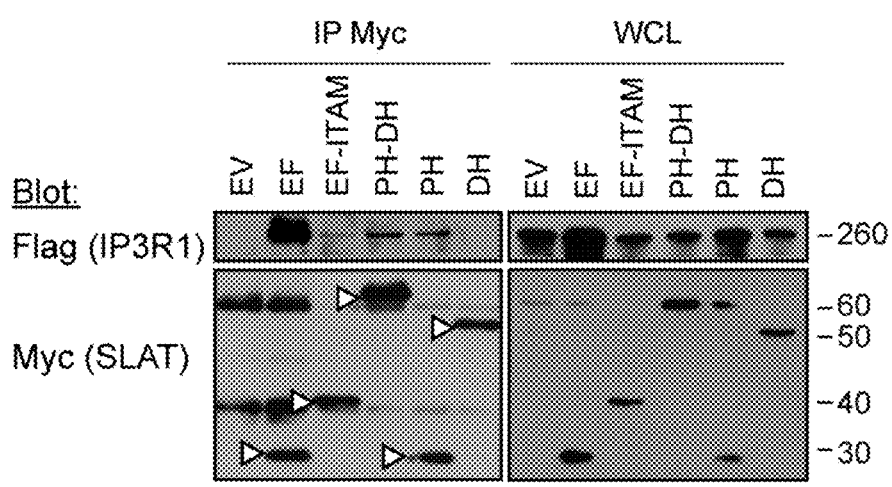
FIG. 3b Immunoblot of anti-Myc SLAT IPs (IP Myc; left panels) or whole cell lysates (WCL; right panels) from Jurkat-TAg T cells cotransfected with the indicated Myc-tagged SLAT mutants (or empty vector; EV) along with Flag-tagged IP3R1. Arrowheads indicate the position of the Myc-SLAT proteins.

To gain further insight into the molecular basis of the SLAT-IP3R1 interaction, a series of Myc-tagged SLAT deletion mutants were ectopically expressed in Jurkat-TAg T cells (FIG. 3a) together with Flag-tagged full-length IP3R1, and their association was analyzed by co-IP (FIG. 3b). The putative EF-hand domain or the PH domain both bound IP3R1 independently and, consistently, all other SLAT mutants that contain either of these domains also associated with the IP3R1 (i.e., EF-ITAM and PH-DH; FIG. 3b). Conversely, the ΔEFAPH SLAT mutant, deleted of both domains, poorly interacted with IP3R1 compared to full-length SLAT (FIG. 8a). Similar results were obtained by performing pull-down studies with GST-SLAT fusion proteins and lysates from IP3R1-transfected 293T cells (FIG. 8b,c).

Figure 3C:
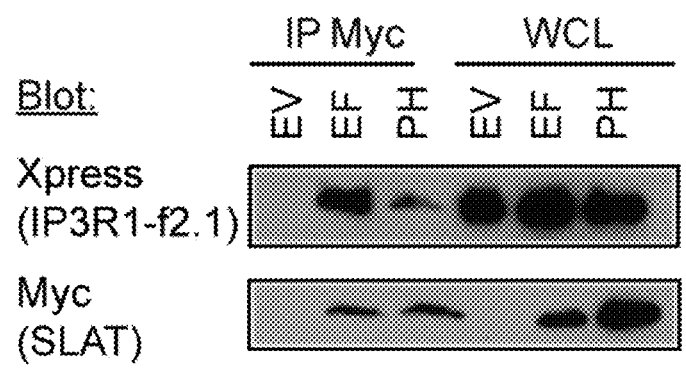
FIG. 3c Immunoblots SLAT IPs or WCL from Jurkat-TAg T cells cotransfected with the indicated Myc tagged SLAT domains plus Flag-tagged IP3R1-f2.1 analyzed as in FIG. 3b.

Co-IP studies were also performed with lysates from Jurkat-TAg cells cotransfected with IP3R1-f2.1 (residues 346-490) along with the putative EF-hand or PH domains of SLAT. Both SLAT domains co-immunoprecipitated with f2.1, with the EF-hand domain displaying more effective interaction than the PH domain (FIG. 3c).

Figure 3D:
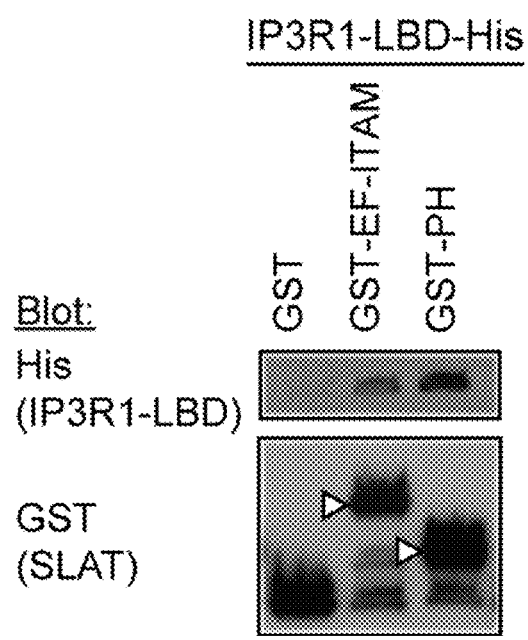
FIG. 3d The indicated immobilized recombinant GST-SLAT proteins (or GST) were incubated with recombinant His-IP3R1-LBD, and eluted proteins were analyzed as in FIG. 2e.

To determine whether the EF-hand or PH domains of SLAT can independently and directly bind the IP3R1, GST pull-down studies were performed with gluthatione bead-immobilized GST-SLAT fusion proteins (FIG. 8b) and a recombinant His-tagged protein representing the IP3R1 LBD (residues 1-581). Both the EF-hand and the PH domains of SLAT precipitated the His-tagged IP3R1 LBD (FIG. 3d), indicating that each of these two domains can independently and directly interact with the IP3R1.

Figure 3E:
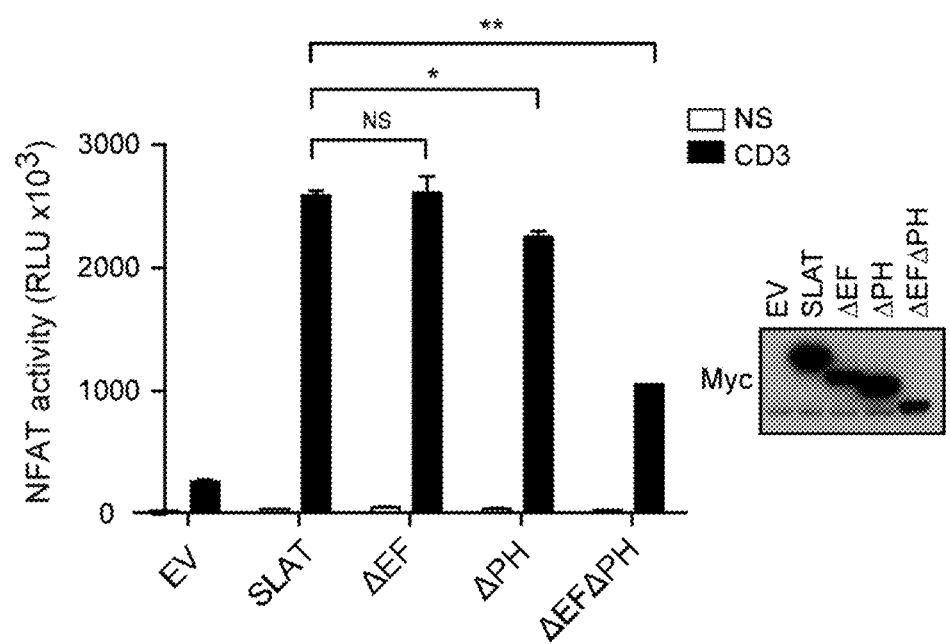
FIG. 3e Jurkat-TAg cells were cotransfected with an empty vector (EV) or the indicated SLAT vectors plus NFAT-Luc and β-Gal reporter genes. Cells were left unstimulated (NS) or stimulated with an anti-CD3 mAb (CD3) for 6 h at 37° C. Normalized Luc activity was determined in duplicates, and bars show means±SD. Expression of the transfected SLAT proteins was detected by anti-Myc immunoblotting (right panel). **, p=0.001, SLAT vs. ΔEFAPH; *, p<0.02, SLAT vs. ΔPH; NS, non-significant. Data shown are representative of at least 3 independent studies.

Ectopic SLAT expression enhances NFAT activation induced by anti-CD3 stimulation (16). To assess the contribution of the SLAT EF-hand and the PH domains to this activity, the ability of SLAT deletion mutants of these two domains to enhance NFAT activation was tested in transfected Jurkat-TAg cells. Upon TCR stimulation, the SLAT mutant lacking the EF-hand domain ($\Delta$EF) as well as the one lacking the PH domain ($\Delta$PH) stimulated NFAT activity to the same extent as WT (full-length) SLAT (FIG. 3e). Only the simultaneous deletion of both domains ($\Delta$EF$\Delta$PH) detectably reduced NFAT activity, demonstrating that each domain alone appears sufficient to promote NFAT activation.

Figure 4A:
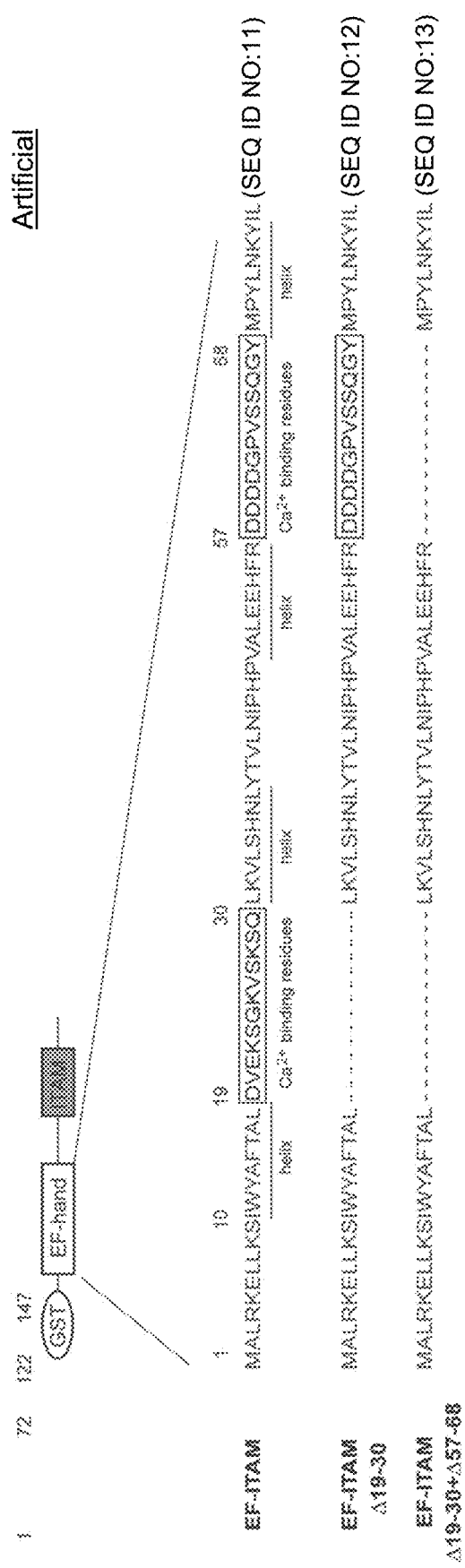
FIG. 4a Schematic representation of SLAT GST-EF-ITAM recombinant proteins used in the $Ca^{2+}$ overlay assay study.
Figure 4B:
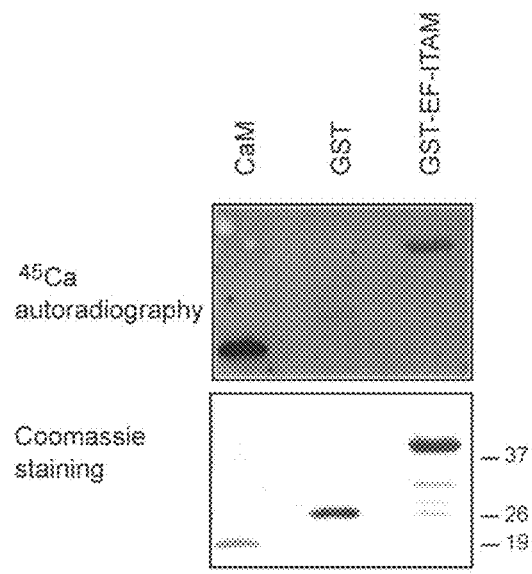
FIGS. 4b-4c The indicated GST fusion proteins were transferred to a nitrocellulose membrane, which was incubated with (45) $CaCl_2$), washed, and subjected to autoradiography (top), followed by Ponceau staining (bottom).
Figure 4C:
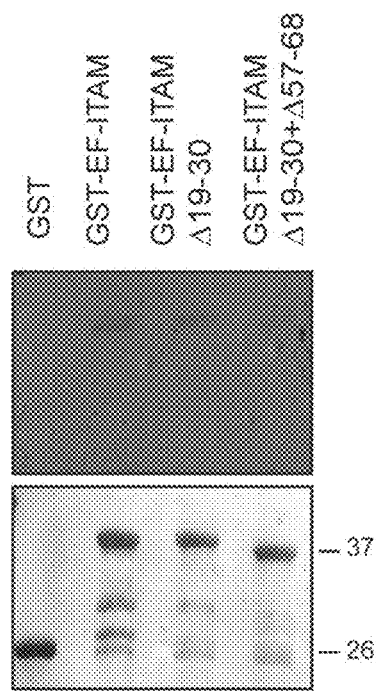

Example 4: The SLAT-IP3R1 Association is $Ca^{2+}$-Dependent: Role of the EF-Hand Domain SLAT harbors at its N-terminus a putative EF-hand domain (residues 1-72) (10) consisting of two potential $Ca^{2+}$ binding motifs (residues 19-30 and 57-68) (15) whose function has not been established. EF-hand domains are highly conserved $Ca^{2+}$-binding motifs found in a large number of intracellular proteins. Typically, this domain assumes a helix-loop-helix structure that binds a single calcium ion through a 12-residue canonical loop, where conserved residues participate in $Ca^{2+}$ binding via their carboxyl or hydroxyl groups (21). To determine whether the N-terminal region of SLAT is a functional $Ca^{2+}$-binding domain, a $^{45}Ca$ overlay assay was performed using a recombinant GST fusion protein consisting of the EF-hand and ITAM domains of SLAT (FIG. 4a), with a GST protein alone and calmodulin (CaM) serving as negative or positive controls, respectively. Autoradiography of the membrane probed with $^{45}Ca$ showed that the GST-EF-ITAM protein bound $Ca^{2+}$ (FIG. 4b). Furthermore, deletion of the two $Ca^{2+}$-binding motifs (EF-ITAM $\Delta$19-30+$\Delta$57-68) greatly, albeit not completely, reduced $Ca^{2+}$ binding, while deletion of a single motif (EF-ITAM $\Delta$ 19-30) had no noticeable effect (FIG. 4c). Thus, SLAT can bind $Ca^{2+}$ and, furthermore, $Ca^{2+}$-binding involves its N-terminal EF-hand domain.

Figure 4D:
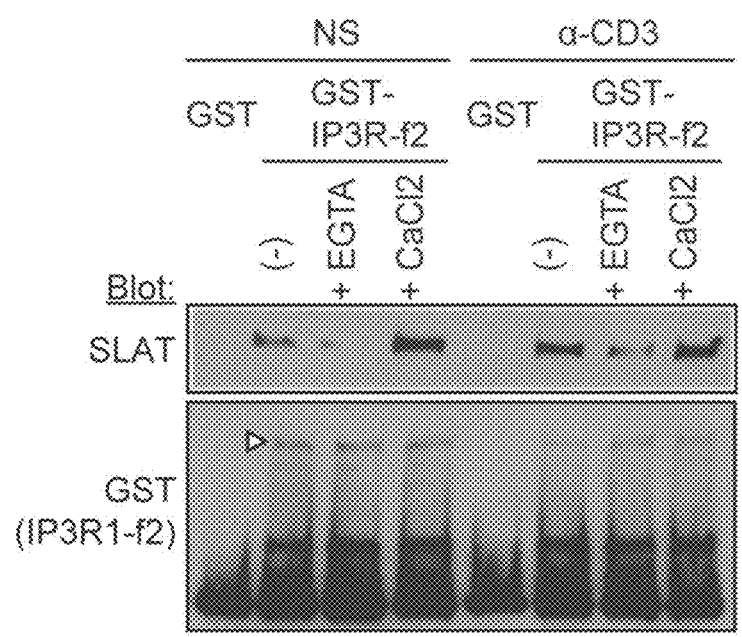
FIG. 4d Lysates of unstimulated or anti-CD3 (OKT3)-stimulated Jurkat-TAg cells were incubated in vitro with GST (negative control) or a GST-IP3R1-f2 fusion protein in the absence (−) or presence of EGTA or CaCl2 (2 mM each). SLAT binding in the absence of $CaCl_2$) or EGTA was assessed in 1% NP-40 lysis buffer (150 nM NaCl, 50 mM Tris-HCl, pH 7.4). Data shown are representative of at least 3 (FIG. 4b, FIG. 4d) and 2 (FIG. 4c) independent studies.

To determine whether the association between SLAT and the IP3R1 is calcium dependent, pull-down studies were carried out by incubating cell lysates from unstimulated or anti-CD3-stimulated Jurkat-TAg cells with a recombinant GST-IP3R1-f2 protein (FIG. 2a) in the presence of $CaCl_2$) or EGTA. As shown in FIG. 4d, inclusion of external $Ca^{2+}$ increased the binding of cellular SLAT to the recombinant IP3R1 protein and, conversely, chelation of $Ca^{2+}$ by EGTA severely reduced this binding relative to the TCR-induced association observed in the absence of either external $Ca^{2+}$ or EGTA.

Example 5: Mapping of a Conserved SLAT-Binding Motif in the IP3R1

Figures 5A, 5B:
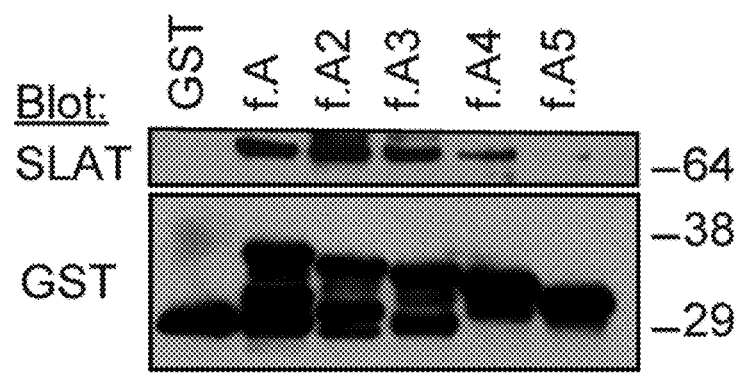
FIG. 5a Schematic representation of IP3R1 fragments used as GST fusion proteins.
FIG. 5b Cell lysates from anti-CD3/CD28-stimulated MCC-T cells were incubated in vitro with the indicated deletion mutants of GSTIP3R1-f.A fragment. Bound proteins were resolved by SDS-PAGE and immunoblotted with anti-SLAT (top panel) or an anti-GST (bottom panel) Abs.
Figure 5C:
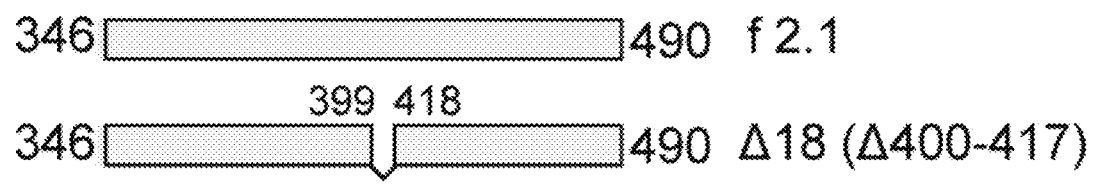
FIG. 5c shows a schematic representation of IP3R1 fragments f2.1 and f2.1 Δ 18.
Figure 5D:
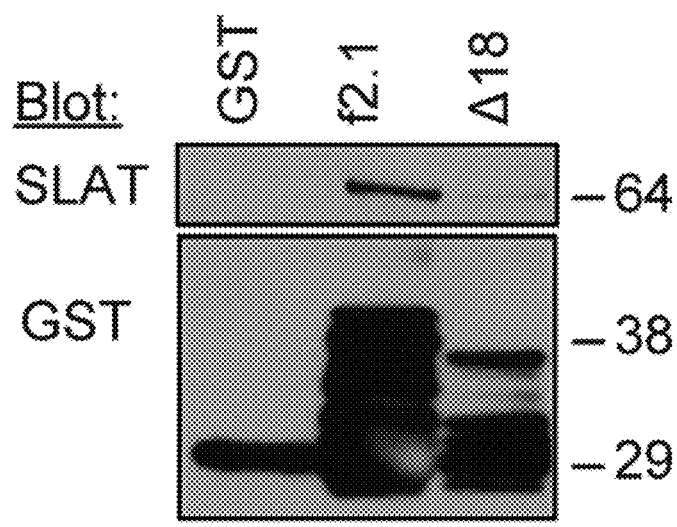
(FIG. 5d shows binding of SLAT in stimulated T cell lysates to the IP3R1 fragments shown in (FIG. 5c) and analyzed as in (FIG. 5b). Data shown are representative of at least 3 independent studies.

Having defined a 96-amino acid IP3R1 region (residues 346-441), which binds SLAT (FIG. 2d), a minimal IP3R1 motif involved in this interaction was identified. Five deletion mutants of IP3R1-f.A (FIG. 2a) were generated, in which stretches of 18 amino acids within this region were successively deleted, for bacterial expression as GST fusion proteins (FIG. 5a). These recombinant proteins were assayed in pull-down studies for their ability to precipitate endogenous SLAT from T cell lysates. The results indicated that deletion of residues 400-417 from IP3R1 f.A abrogated its ability to interact with SLAT (FIG. 5b), whereas all other deletions had minimal, if any, effect on the interaction (with the possible exception of the A4 mutation, which seemed to reduce the interaction by comparison with the non-deleted f.A fusion protein). A function of this 18-amino acid region was confirmed by performing similar pulldown analysis using a larger GST fusion protein of IP3R1 f2.1 (residues 346-490), from which residues 400-417 were deleted (FIG. 5c), and it was found that deletion of these 18 residues abolished interaction with SLAT (FIG. 5d). These results establish the short motif comprising amino acid residues 400-417 in the IP3R1 (FIG. 9) as being important for the interaction with SLAT. The polar motif, which contains four negatively charged and three positively charged residues, is highly conserved evolutionarily and among IP3R subtypes (FIG. 9).

Example 6: Disruption of the SLAT-IP3R1 Interaction Inhibits $Ca^{2+}$ Signaling and Cytokine Expression In order to assess the biological significance of the SLAT-IP3R1 interaction, a strategy was designed to disrupt this interaction in T cells, which relied on a blocking cell-permeable recombinant peptide. The independent binding of both the EF-hand and PH domains of SLAT to the IP3R1 ruled out the feasibility of testing a SLAT-based blocking peptide. Instead, a cell-permeable fusion protein was generated by cloning the cDNA encoding IP3R1-f2.1 (residues 346-490) or, as a control, the same region deleted of residues 400-417, into a bacterial expression vector (pTAT-HA) (22) encoding a hemagglutinin (HA)-tagged HIV-1 TAT protein derived peptide (TAT-HA-2.1 and TAT-HA-2.1418, respectively) (FIG. 6a). Efficient peptide transduction was assessed and confirmed by performing anti-HA immunoblots blots on peptide treated CD4+ T cell lysates. Using co-IP analysis, it was found that pre-incubation of T cells with the TAT-HA-2.1 peptide reduced the stimulation-induced interaction between endogenous SLAT and the IP3R1 by 75% by comparison to the negative control of the TAT-HA protein alone. In contrast, the mutated peptide (TAT-HA-2.1418) caused a mild, ~20% reduction of this interaction (FIG. 6b). This residual inhibitory activity could reflect a more modest contribution of other IP3R1 residues, besides the 18 deleted residues, to the interaction.

Figure 10A:
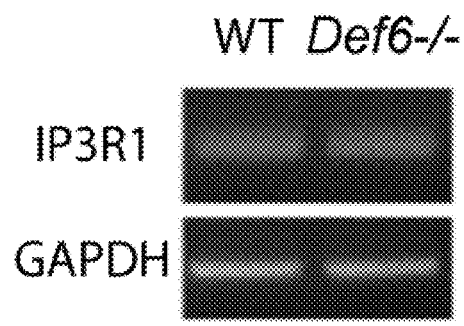
FIG. 10a shows intact IP3R1 expression in Def6−/− T cells. IP3R1 mRNA and protein expression were analyzed by RT-qPCR.
Figure 10B:
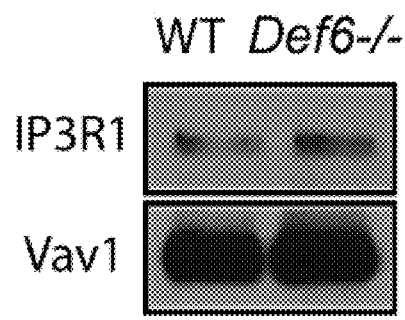
FIG. 10b shows intact IP3R1 expression in Def6−/− T cells. IP3R1 mRNA and protein expression were analyzed by immunoblotting.

The effect of these TAT fusion proteins on different aspects of TCR induced CD4+ T cell activation was analyzed. As shown in FIG. 6c, transduction with the control, mutated TATIP3R1 fusion protein had a minimal, if any, effect on the increase in $[Ca^{2+}]i$; however, treatment with the blocking fusion protein (TAT-HA-2.1) drastically inhibited the TCR-induced increase in [$Ca^{2+}$]i, phenocopying the reduced and delayed response observed in Def6−/− CD4+ T cells (FIG. 6c), despite normal IP3R1 expression (FIG. 10).

Figure 6D:
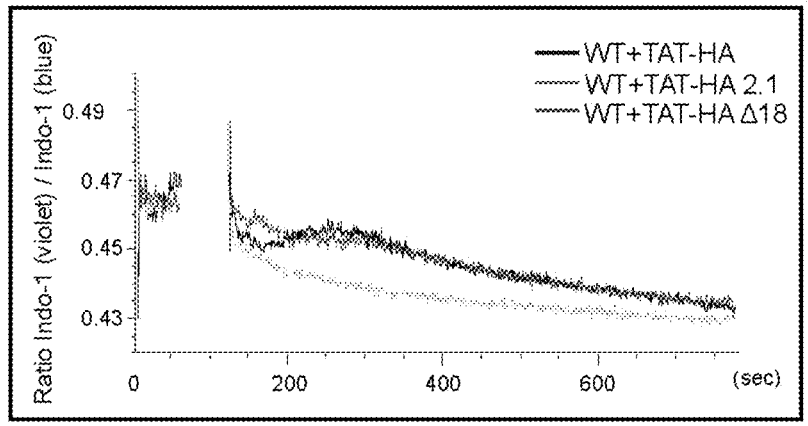

A similar study was performed in the absence of extracellular $Ca^{2+}$ by including EGTA in the culture medium in order to determine whether the blocking peptides prevents $Ca^{2+}$ release from the ER and/or $Ca^{2+}$ influx from the external medium. By comparison with the control TATHA protein, the TAT-HA-2.1 fusion protein abrogated $Ca^{2+}$ release from the ER, in contrast to cells treated with the TAT-HA-2.1418 protein, which displayed intact intracellular $Ca^{2+}$ release (FIG. 6d). It was found that transduction with either of the two fusion proteins did not detectably alter the TCR-induced phosphorylation of ZAP-70 kinase, LAT, PLCγ1, Akt, GSK3, or p38 kinase (FIG. 11a).

Figure 6E:
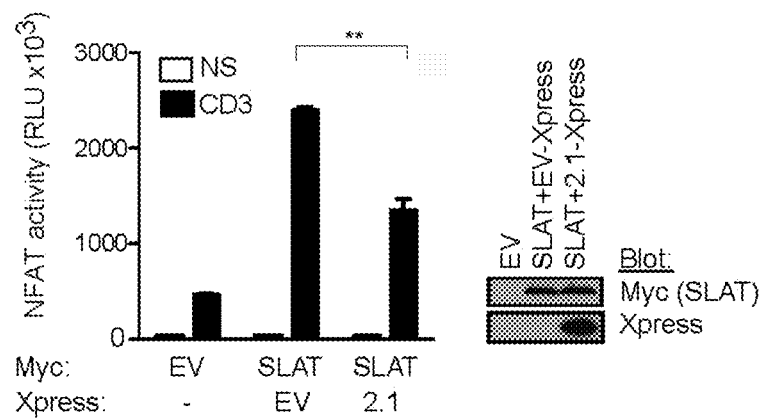
FIG. 6e J-TAg cells cotransfected with empty vector (EV), or a Myc-tagged SLAT expression vector in the absence or presence of Xpress-tagged TAT-HA-2.1, plus NFAT-Luc and β-Gal reporter plasmids were left unstimulated (NS) or stimulated with an anti-CD3 (CD3) mAb for 6 h. Normalized Luc activity was determined in duplicates and bars show means±SD. **, p<0.01, SLAT vs. SLAT+2.1. Expression of transfected SLAT and IP3R1-f2.1 proteins was detected by anti-Myc or anti-Xpress immunoblotting, respectively (right panel).

It was next evaluated the effect of the TAT-HA-2.1 protein on TCR-induced activation of an NFAT-luciferase (Luc) reporter gene. Expression of full-length SLAT enhanced the TCR-stimulated NFAT activity in Jurkat-TAg cells; however, when the cells were additionally cotransfected with the SLAT-2.1 protein, the SLAT-stimulated NFAT activity was reduced, albeit not entirely abolished (FIG. 6e). In contrast, the TCR-induced stimulation of an NF-κB reporter gene, either in the absence or presence of transfected SLAT, was not inhibited by the TAT-HA-2.1 protein (FIG. 11b).

Figure 6F:
FIG. 6f B6 CD4+ T cells were pre-incubated with the indicated TAT proteins for 1 h and stimulated with plate-bound anti-CD3 plus soluble anti-CD28 mAbs (2.5 μg/ml each) in the presence of TAT fusion proteins (150 nM). The culture medium was supplemented with fresh medium plus TAT proteins after 12 and 24 h. Supernatants were collected after 48 h, and IFNγ levels in culture supernatants were determined by an ELISA. *p=0.0001, WT+TAT-HA vs. Def6−/−; p<0.002, WT+TAT-HA vs. WT+TAT-HA 2.1; *p<0.05 WT+TAT-HA 2.1 vs. WT+TAT-HA A 18. Data shown are representative of at least 3 (FIG. 6b, FIG. 6c, FIG. 6e, FIG. 6f) and 2 (FIG. 6d) independent studies.

Lastly, the consequences of disrupting the SLAT-IP3R1 interaction on IFNγ production were investigated. The anti-CD3/CD28-stimulated IFNγ production by CD4+ T cells transduced with the TAT-HA-2.1 fusion protein was reduced by ~50-60% relative to the control TAT-HA protein (FIG. 6f). Cells treated with the TAT-HA-2.1 Δ 18 fusion protein also showed a weak (~15-20%) reduction in cytokine production (FIG. 6f), likely due to the fact that the TAT-HA-2.1 Δ 18 protein retains weak ability to reduce the SLAT-IP3R1 interaction (FIG. 6b).

Example 7: Discussion

During the course of T lymphocyte activation, the rise in [$Ca^{2+}$]i is an important step that regulates the strength and type of immune responses by controlling many biological functions (1, 23, 24). Despite recent breakthroughs made in this area with the identification of the ER $Ca^{2+}$ sensor STIM1, and the Orai1 protein as a subunit of the CRAC channel (25-27), many of the processes that regulate $Ca^{2+}$ entry remain unknown. In TCR-stimulated T cells, $Ca^{2+}$ signaling is initiated by the emptying of intracellular $Ca^{2+}$ stores in response to the binding of the second messenger IP3 to its receptor, the IP3R. However, relatively few studies have addressed the regulation and function of these receptors in T lymphocytes (6, 28-35).

It was hypothesized that SLAT is important for proper IP3R function in response to TCR stimulation, and may reflect a physical SLAT-IP3R1 interaction. Here, a direct TCR-induced association between SLAT and the IP3R1 was identified, and interaction of EF-hand and the PH domains of SLAT independently and directly interact with the IP3R1 shown. In addition, it was shown for the first time that the N-terminal region of SLAT binds $Ca^{2+}$ and was demonstrated that the SLAT-IP3R1 association is $Ca^{2+}$-dependent. Lastly, an 18-residue IP3R1 motif that is required for SLAT binding was identified, and it was found that disruption of the SLAT-IP3R1 association severely inhibited TCR-induced $Ca^{2+}$ signaling and reduced cytokine production. Thus, the data disclosed herein identify SLAT as a novel IP3R1-interacting protein and unravel a novel, potentially T cell-specific mechanism for IP3R1 regulation and function. Given the predominant expression of SLAT in T lymphocytes, the results implicate SLAT as a selective drug target for the treatment of NFAT-dependent, T cell-mediated autoimmune and inflammatory diseases.

The stimulus-induced association between SLAT and the IP3R1 was rapid and declined by ~15 min, suggesting that it is required for the early stages of intracellular $Ca^{2+}$ release. The results of the proximity ligation and co-fractionation assays are consistent with this physical association, and demonstrate that a fraction of SLAT is present in the ER-enriched subcellular fraction. Given the fact that SLAT does not contain an ER retention signal motif (36), it is unlikely that SLAT localizes in the ER lumen but instead it likely interacts with the cytosolic part of the IP3R1 that represents 85% of the protein (9, 37). The IP3R1 was also detected in the membrane fraction, in accordance with previous studies showing IP3R1 expression at the PM of lymphocytes, where it is present as a potentially functional $Ca^{2+}$ channel (4, 28, 38). However, the possibility cannot be excluded that IP3R1 expression in the membrane fraction is due to the coprecipitation of heavy membranes, which include, in addition to the PM, the rough ER, as well as plasma membrane-associated membranes (PAM) and mitochondria, where IP3R1 expression has been previously described (39, 40). SLAT enrichment could not be detected in the membrane fraction, which was previously noted (16), upon TCR stimulation. This difference may reflect the fact that the subcellular fractionation protocol that was used differed substantially from the one originally used to document the TCR-induced translocation of SLAT to the PM (16).

The N-terminal region of SLAT containing a functional $Ca^{2+}$-binding EF-hand domain was identified as important for the SLAT-IP3R1 interaction. Although participation of the ITAM-like domain in $Ca^{2+}$ binding cannot be excluded, it is highly likely that $Ca^{2+}$ binding is mediated by the EF-hand domain since deletion of the two putative $Ca^{2+}$-binding sites greatly reduced $Ca^{2+}$ binding to SLAT. These $Ca^{2+}$-binding motifs share 63% and 68% homology with a consensus EF-hand domain sequence (15, 44) and due to alteration of a single residue in these motifs relative to the consensus sequence, the SLAT EF hand domain may only have a low $Ca^{2+}$ affinity (15). Interestingly, the SLAT region that harbors the EF-hand domain (residues 1-72) is the most conserved part between SLAT and its SWAP-70 homolog, suggesting an important function of this region (10). Together with IP3, $Ca^{2+}$-binding to IP3Rs is a major regulatory feature of IP3R channel activity and eight $Ca^{2+}$-binding sites have been identified in the protein (45). IP3R activity can be regulated through direct $Ca^{2+}$ binding or through IP3R association with $Ca^{2+}$-sensing proteins. One IP3R1 $Ca^{2+}$-binding site is localized in its N-terminal region encompassing residues 378-450 (46), including the 18 residues (400-417) were found to be important for the interaction with SLAT. SLAT may function as a $Ca^{2+}$ sensor via its N-terminal $Ca^{2+}$-binding region and thereby promote IP3R1 activation by facilitating $Ca^{2+}$ binding to the channel. Alternatively, SLAT may compete with other $Ca^{2+}$-binding proteins that bind to the IP3R and negatively regulate its channel activity (7).

The isolated PH-DH tandem domains alone, or deletion of the SLAT N-terminal region (containing the EF-hand domain) have no apparent effect on its biological activities (16) and the simultaneous deletion of both EF-hand and PH domains reduced the ability of SLAT to enhance NFAT activation. On the other hand, the importance of the ITAM-like motif of SLAT localized between the EF-hand and PH domains for its proper localization and downstream functions may indicate that upon TCR stimulation, phosphorylation of this ITAM-like motif induces a conformational change that renders its EF-hand and PH domains accessible for interaction with the IP3R1.

The regulatory interplay between $Ca^{2+}$ signaling and actin cytoskeleton rearrangement is important to sustain and amplify T cell activation and functions (47). Although the SLAT catalytic DH domain was not required for the IP3R1 interaction, it remains to be determined whether the GEF activity of SLAT is directly required for $Ca^{2+}$ signaling or whether SLAT promotes $Ca^{2+}$ release through its IP3R1 association independently of its GEF activity. The ability of a dominant negative Cdc42 (a target of SLAT GEF activity) mutant to inhibit SLAT-mediated $Ca^{2+}$ suggests a role for the GEF activity of SLAT (16).

A minimal, 18-residue region within the IP3R1 LBD was identified, which was important for the interaction with SLAT. The evolutionary and IP3R subtype conservation of this motif indicates that is has an important regulatory role and, furthermore, suggests that IP3R2 and/or IP3R3 may also bind SLAT. However, since TCR/CD28 costimulation has been reported to down-regulate the expression of IP3R2 and IP3R3, but not IP3R1, in CD4+ T cells (50), it is possible that SLAT regulates $Ca^{2+}$ release in T cells by interacting predominantly with the IP3R1. However, the specific contribution of different IP3R subtypes to the overall $Ca^{2+}$ mobilization in TCR stimulated T cells is difficult to evaluate (31). The functional effects of disrupting this interaction, namely, inhibition of $Ca^{2+}$ mobilization, NFAT activation, and IFNγ production, establish the biological relevance of the SLAT-IP3R1 interaction in T cell activation.

IP3R subtypes differentially contribute to the regulation of cytosolic $Ca^{2+}$ oscillations, and this behavior is determined by differences in IP3 affinity (7), relative expression levels (1), and the nature of associated regulatory proteins. These differences may be responsible for initiating distinct $Ca^{2+}$ oscillation patterns and shaping $Ca^{2+}$ signaling profiles in different cell types (8, 51). IP3R regulatory mechanisms functionally similar to those mediated by SLAT in T cells may operate in other cell types, which express very little (or no) SLAT.

SLAT does not appear to affect IP3 binding to IP3R1. Elucidation of the crystal structure of IP3R1-binding SLAT domains, either alone or in combination with the corresponding IP3R1 region may provide insight to specifically target this interaction. Evaluation of the effect of disrupting the SLAT-IP3R interaction in animal models of T cell-mediated autoimmune and inflammatory diseases will facilitate the design of novel inhibitors, which could act selectively to inhibit $Ca^{2+}$ signaling in T cells without (or only minimally) affecting other TCR signaling pathways.

Example 8: Methods

Mice.

C57BL/6 (136) mice and Def6-/- mice on a B6 background (13) were housed and manipulated according to a protocol approved by the La Jolla Institute for Allergy and Immunology Animal Care Committee and in accordance with the Association for Assessment and Accreditation of Laboratory Animal Care International.

Expression Vectors.

Vectors encoding Myc-tagged SLAT or its mutants were generated by PCR and cloned into the pEF-Myc-His A/C mammalian vectors (Life Technologies) encoding an in-frame Myc tag epitope downstream of the insert, or into the pET28a+ bacterial vector (Merck Millipore), resulting in an expressed protein with N- and C-terminal His tags. The various GSTSLAT fusion proteins were generated by PCR and cloned into the pGEX-4T1 vector encoding a N-terminal GST fusion protein. The GST EF-ITAM Δ 19-30 and EF-ITAM Δ 19-30+Δ 57-68 vectors were generated by mutagenesis from the GST EF-ITAM template using QuikChange II XL Site-Directed Mutagenesis Kit (Agilent Technologies) according to the manufacturer's instructions. The Flag-IP3R1 mammalian expression vector has been previously described (56). cDNAs encoding IP3R1 fragments f.1-f.6 fused to GST at their N-terminus cloned into pGEX-6p2 vector as well as IP3R1-LBD-His (residues 1-581) have been described (57, 58). cDNAs encoding other IP3R1 fragments were constructed by PCR and cloned into the pGEX-4T2 vector (GE Healthcare Life Sciences). cDNAs for IP3R1 fragments f2.1 or f2.1 Δ 18 were generated by PCR, cloned into the pTAT-HA bacterial vector, and produced as previously described (22).

Cell Purification, Culture and Stimulation.

After red blood cell lysis, splenic CD4+ T cells were isolated by positive selection using anti-mouse CD4 magnetic particles (BD Biosciences) or by negative selection (CD4+ T cell Isolation kit II, Miltenyi Biotec). T cells were cultured in RPMI 1640 medium (Life Technologies) supplemented with 10% FBS, 2 mM glutamine, 1 mM sodium pyruvate, 10 mM HEPES, 1 mM MEM nonessential amino acid solution, and 100 U/ml each of penicillin G and streptomycin (Life Technologies). For short stimulation (IP studies, GST pull-downs, subcellular fractionation), 5-15× $10^6$ T cells resuspended in serum-free medium were incubated for 30 min on ice with 20 μg/ml each anti-mouse CD3ε monoclonal antibody (mAb; 145-2C11; BioLegend) and anti-CD28 mAb (37.51; BioLegend), followed by crosslinking with goat anti-hamster IgG (Thermo scientific) for the indicated times at 37° C. with gentle shaking. To generate T cell blasts, purified T cells were stimulated with plate-bound anti-CD3 (5 μg/ml) plus soluble anti-CD28 (2.5 μg/ml) mAbs in the presence of human recombinant IL-2 (100 U/ml; Peprotech) for 48-72 h. The mouse MCC-specific T cell hybridoma (MCC-T) (18) was cultured and stimulated as above, and the human Jurkat T cell line derivatives JA1659 or Jurkat-TAg cells (the latter expressing Simian virus 40 large T antigen) were cultured and stimulated with an anti-human CD3 mAb (OKT3; BioXCell) followed by crosslinking with goat anti-mouse IgG (Thermo Scientific).

Immunoprecipitation (IP).

Cells were stimulated as described above and lysed in 1% NP-40, 150 mM NaCl, 50 mM Tris, pH 7.4, 10 mM NaF, 1 mM PMSF, and 10 μg/ml each aprotinin and leupeptin. Lysates were collected after centrifugation at 13,000×g for 10 min. IP was performed by adding the indicated Abs plus 30 μl of protein G-Sepharose (GE Healthcare Life Sciences) and incubating the lysates overnight at 4° C. Samples were washed 4× with lysis buffer, and the IPs were dissolved in 1× Laemmli buffer, subjected to SDS-PAGE, transferred to nitrocellulose membrane, and immunoblotted with an anti Flag M2 mAb (F3165; Sigma), anti-Myc Ab (sc-40; Santa Cruz Biotechnology inc.), or anti-Xpress Ab (R910-25; Life Technologies). To assess the effect of the TAT fusion proteins on the SLAT-IP3R1 interaction, cells were previously stimulated for 72 h, rested overnight with 20 U/ml IL-2, and then restimulated after a 1.5 h incubation with the indicated TAT fusion proteins in RPMI-1640 plus 0.5% FBS at 37° C.

Proximity Ligation Assay.

Proximity between SLAT and IP3R1 was analyzed using the Duolink proximity ligation assay according to the manufacturer's instructions (Olink Bioscience). Briefly, CD4+ T cells were blasted for 3 d, rested overnight, and seeded on anti-CD3 plus-CD28 mAb-coated coverslips for 15 min before fixation and saponin permeabilization. Cells were stained with mouse anti-IP3R1 mAb (clone L24/18; UC Davis/NIH NeuroMab Facility) and rabbit anti-SLAT Ab (10) on WT T cells. Negative controls included staining of Def6−/− T cells with a combination of anti-SLAT plus −IP3R1 Abs or by omitting the anti-IP3R1 mAb from WT T cells. Generated fluorescence spots were counted and the average number of spots per cell was determined.

GST Pull-Downs.

GST fusion proteins (10 µg) were immobilized on glutathione-Sepharose 4B beads (GE Healthcare Life Sciences) at 4° C. for 1 h in TEN buffer (20 mM Tris, pH 7.4, 0.1 mM EDTA, 100 mM NaCl), washed 4× with TEN buffer to remove unbound material and incubated with pre-cleared whole cell extracts of stimulated Jurkat-TAg cells or MCC-T cells at 4° C. for 1 h. Beads were washed 4× with 0.5% NP-40, 20 mM Tris, pH 7.4, 0.1 mM EDTA, 300 mM NaCl, and eluted proteins were analyzed by SDS-PAGE with anti-GST mAb (sc-138; Santa Cruz biotechnology inc.) and anti-His mAb (sc-8036; Santa Cruz biotechnology Inc.). To assess the direct interaction between SLAT and IP3R1, 10 µg of His-SLAT fusion protein were incubated with immobilized GST fusion proteins at 4° C. for 1 h in 1% NP-40, 150 mM NaCl, 50 mM Tris, pH 7.4, 10 mM NaF, 1 mM PMSF, and 10 µg/ml each aprotinin and leupeptin, washed 4× in the same buffer, and eluted before SDS-PAGE analysis and immunoblotting.

Subcellular Fractionation.

$50 \times 10^6$ MCC-specific T hybridoma cells were stimulated as described above with anti-CD3 plus-CD28 mAbs (2 min; 37° C.) with gentle shaking and resuspended in ice-cold buffer (0.25 M sucrose, 1 mM EGTA, 3 mM imidazole). Cells were disrupted by sonication and then homogenized with a 27-gauge needle. Nuclei were pelleted by centrifugation (800×g, 5 min) and supernatants centrifuged at 1,450×g for 10 min at 4° C. to obtain the membrane fraction (P1). Centrifugation at 17,000×g, 10 min, at 4° C. was performed to obtain the organelle fraction (mitochondria, lysosomes, endosomes and peroxisomes) (P2). A final centrifugation at 100,000×g (1 h at 4° C.) was performed to separate the ER and Golgi (P3) from the cytosol (SN3). Fractions were resolved on a 4-12% gradient gel (Life technologies) and blotted with anti-α1 sodium-potassium ATPase (ab7671; Abcam) or anti-p38 (#9212, Cell Signaling Technology) Abs.

Cat Overlay Assay.

Purified SLAT-GST recombinant proteins were transferred to a PVDF membrane after separating on a 12% SDS-PAGE gel. The blot was extensively washed for 3×30 min with binding buffer (60 mM KCl, 5 mM $MgCl_2$ and 10 mM imidazole-HCl, pH 6.8). The overlay assay was performed by incubating the blot with 5 µCi/ml of $^{45}CaCl_2$ (Perkin Elmer) for 1 h at room temperature with gentle shaking, followed by 3×5 min washes in distilled $H_2O$. After autoradiography, the blot was stained with Ponceau S solution for detection of proteins.

Intracellular Calcium Measurements.

Purified T cells were incubated with 150 nM of the indicated TAT fusion proteins for 1.5 h in RPMI-1640/0.5% FBS at 37° C. and then loaded with indol-AM (Invitrogen 11226; 2 µg/ml; Molecular Probes) in cell-loading medium HBSS medium supplemented with $CaCl_2$) and $MgCl_2$ (Life Technologies) in the presence of 4 mM probenecid (45 min at 37° C. in the dark). Loaded cells were washed twice with cell loading medium and were incubated with anti-CD3 (10 µg/ml) plus-CD28 (2.5 µg/ml) mAbs for 30 min at RT. Unbound Abs were removed by centrifugation, and cells were then resuspended in cell-loading medium to determine a baseline $[Ca^{2+}]i$ level. A crosslinking goat anti-hamster Ab (10 µg/ml) was then added. To assess $Ca^{2+}$ release from intracellular stores, cells were washed in HBSS (Life Technologies) and resuspended in 1 mM EGTA-containing HBSS to chelate extracellular $Ca^{2+}$. Cells were analyzed by reading the emission at 500 nm (FL4 channel) and 460 nm (FL5 channel) on an LSRII instrument (BD) and calculating the FL5/FL4 emission ratio.

Luciferase Reporter Gene Assays.

$20 \times 10^6$ Jurkat-TAg or JA16 Jurkat cell line derivatives were cotransfected with empty pEF vector (10 µg) or with pEF vector encoding Myc-tagged SLAT mutants, with or without Xpress-tagged IP3R1-f2.1, together with NFAT-Luc or NF-κB-Luc (5 µg each) plus β-Gal (5 µg) reporter genes. Cells were left unstimulated or stimulated with anti-CD3 (OKT3) mAb for 6 h at 37° C. Normalized Luc activity was determined in duplicates, and graphs show mean±SD. Expression of transfected proteins was detected by immunoblotting.

IFNγ ELISA.

Purified CD4+ T cells were pre-incubated for 2 h at 37° C. with 150 nM of the indicated TAT fusion proteins in RPMI-1640/0.5% FBS. The cells were washed and resuspended in RPMI-1640/10% FBS containing 2.5 µg/ml anti-CD28 mAbs and fresh TAT proteins (150 nM). Cells ($2 \times 10^5$/well) were stimulated at 37° C. in an anti-CD3 mAb-coated 96-well plate (2.5 µg/ml) for 48 h. Fresh TAT proteins (150 nM) in RPMI-1640 (100 µl) were added to the cells after 12 and 24 h. Supernatants were collected after 48 h, and ELISA assays were performed.

Statistics.

Statistical significance was analyzed by 2-tailed Student's t test. Unless otherwise indicated, data represent the mean±SD, with $p<0.05$ considered statistically significant.

REFERENCES

1. Lewis, R. S. Calcium signaling mechanisms in T lymphocytes. Annu Rev Immunol 19, 497-521 (2001).
2. Feske, S. Calcium signalling in lymphocyte activation and disease. Nat Rev Immunol 7, 690-702 (2007).
3. Patterson, R. L., Boehning, D. & Snyder, S. H. Inositol 1,4,5-trisphosphate receptors as signal integrators. Annu Rev Biochem 73, 437-465 (2004).
4. Tanimura, A., Tojyo, Y. & Turner, R. J. Evidence that type I, II, and III inositol 1,4,5-trisphosphate receptors can occur as integral plasma membrane proteins. J Biol Chem 275, 27488-27493 (2000).
5. Taylor, C. W. & Tovey, S. C. IP(3) receptors: toward understanding their activation. Cold Spring Harbor perspectives in biology 2, a004010 (2010).
6. Jayaraman, T., Ondriasova, E., Ondrias, K., Harnick, D. J. & Marks, A. R. The inositol 1,4,5-trisphosphate receptor is essential for T-cell receptor signaling. Proceedings of the National Academy of Sciences of the United States of America 92, 6007-6011 (1995).
7. Foskett, J. K., White, C., Cheung, K. H. & Mak, D. O. Inositol trisphosphate receptor $Ca^{2+}$ release channels. Physiological reviews 87, 593-658 (2007).

8. Zhang, S., Fritz, N., Ibarra, C. & Uhlen, P. Inositol 1,4,5-trisphosphate receptor subtypespecific regulation of calcium oscillations. Neurochemical research 36, 1175-1185 (2011).
9. Choe, C. U. & Ehrlich, B. E. The inositol 1,4,5-trisphosphate receptor (IP3R) and its regulators: sometimes good and sometimes bad teamwork. Sci STKE 2006, re15 (2006).
10. Tanaka, Y. et al. SWAP-70-like adapter of T cells, an adapter protein that regulates early TCR-initiated signaling in Th2 lineage cells. Immunity 18, 403-414 (2003).
11. Hotfilder, M., Baxendale, S., Cross, M. A. & Sablitzky, F. Def-2, -3, -6 and -8, novel mouse genes differentially expressed in the haemopoietic system. Br J Haematol 106, 335-344. (1999).
12. Gupta, S. et al. Molecular cloning of IBP, a SWAP-70 homologous GEF, which is highly expressed in the immune system. Hum Immunol 64, 389-401 (2003).
13. Becart, S. et al. SLAT regulates Th1 and Th2 inflammatory responses by controlling $Ca^{2+}$/NFAT signaling. J Clin Invest 117, 2164-2175 (2007).
14. Gupta, S. et al. T cell receptor engagement leads to the recruitment of IBP, a novel guanine nucleotide exchange factor, to the immunological synapse. J Biol Chem 278, 43541-43549 (2003).
15. Mavrakis, K. J., McKinlay, K. J., Jones, P. & Sablitzky, F. DEF6, a novel PH-DH-like domain protein, is an upstream activator of the Rho GTPases Rac1, Cdc42, and RhoA. Exp Cell Res 294, 335-344 (2004).
16. Becart, S. et al. Tyrosine-phosphorylation-dependent translocation of the SLAT protein to the immunological synapse is required for NFAT transcription factor activation. Immunity 29, 704-719 (2008).
17. Fredriksson, S. et al. Protein detection using proximity-dependent DNA ligation assays. Nature biotechnology 20, 473-477 (2002).
18. So, T., Soroosh, P., Eun, S. Y., Altman, A. & Croft, M. Antigen-independent signalosome of CARMA1, PKCtheta, and TNF receptor-associated factor 2 (TRAF2) determines NFkappaB signaling in T cells. Proceedings of the National Academy of Sciences of the United States of America 108, 2903-2908 (2011).
19. Uchida, K., Miyauchi, H., Furuichi, T., Michikawa, T. & Mikoshiba, K. Critical regions for activation gating of the inositol 1,4,5-trisphosphate receptor. J Biol Chem 278, 16551-16560 (2003).
20. Taylor, C. W., da Fonseca, P. C. & Morris, E. P. IP(3) receptors: the search for structure. Trends in biochemical sciences 29, 210-219 (2004).
21. Lewit-Bentley, A. & Rety, S. EF-hand calcium-binding proteins. Current opinion in structural biology 10, 637-643 (2000).
22. Becker-Hapak, M. & Dowdy, S. F. Protein transduction: generation of full-length transducible proteins using the TAT system. Curr Protoc Cell Biol Chapter 20, Unit 20 22 (2003).
23. Oh-hora, M. & Rao, A. Calcium signaling in lymphocytes. Current opinion in immunology 20, 250-258 (2008).
24. Gwack, Y., Feske, S., Srikanth, S., Hogan, P. G. & Rao, A. Signalling to transcription: store-operated $Ca^{2+}$ entry and NFAT activation in lymphocytes. Cell calcium 42, 145-156 (2007).
25. Vig, M. et al. CRACM1 is a plasma membrane protein essential for store-operated $Ca^{2+}$ entry. Science 312, 1220-1223 (2006).
26. Zhang, S. L. et al. STIM1 is a $Ca^{2+}$ sensor that activates CRAC channels and migrates from the $Ca^{2+}$ store to the plasma membrane. Nature 437, 902-905 (2005).
27. Prakriya, M. et al. Orai1 is an essential pore subunit of the CRAC channel. Nature 443, 230-233 (2006).
28. Khan, A. A., Steiner, J. P., Klein, M. G., Schneider, M. F. & Snyder, S. H. IP3 receptor: localization to plasma membrane of T cells and cocapping with the T cell receptor. Science 257, 815-818 (1992).
29. Khan, A. A., Steiner, J. P. & Snyder, S. H. Plasma membrane inositol 1,4,5-trisphosphate receptor of lymphocytes: selective enrichment in sialic acid and unique binding specificity. Proceedings of the National Academy of Sciences of the United States of America 89, 2849-2853 (1992).
30. Harnick, D. J. et al. The human type 1 inositol 1,4,5-trisphosphate receptor from T lymphocytes. Structure, localization, and tyrosine phosphorylation. J Biol Chem 270, 2833-2840 (1995).
31. Hirota, J. et al. T-cell-receptor signalling in inositol 1,4,5-trisphosphate receptor (IP3R) type-1-deficient mice: is IP3R type 1 essential for T-cell-receptor signalling? The Biochemical journal 333 (Pt 3), 615-619 (1998).
32. Chen, R. et al. Bcl-2 functionally interacts with inositol 1,4,5-trisphosphate receptors to regulate calcium release from the ER in response to inositol 1,4,5-trisphosphate. J Cell Biol 166, 193-203 (2004).
33. Dadsetan, S., Zakharova, L., Molinski, T. F. & Fomina, A. F. Store-operated $Ca^{2+}$ influx causes $Ca^{2+}$ release from the intracellular $Ca^{2+}$ channels that is required for T cell activation. J Biol Chem 283, 12512-12519 (2008).
34. Steinmann, C., Landsverk, M. L., Barral, J. M. & Boehning, D. Requirement of inositol 1,4,5-trisphosphate receptors for tumor-mediated lymphocyte apoptosis. J Biol Chem 283, 13506-13509 (2008).
35. Rong, Y. P. et al. The BH4 domain of Bcl-2 inhibits ER calcium release and apoptosis by binding the regulatory and coupling domain of the IP3 receptor. Proceedings of the National Academy of Sciences of the United States of America 106, 14397-14402 (2009).
36. Pelham, H. R. The retention signal for soluble proteins of the endoplasmic reticulum. Trends in biochemical sciences 15, 483-486 (1990).
37. Jiang, Q. X., Thrower, E. C., Chester, D. W., Ehrlich, B. E. & Sigworth, F. J. Three dimensional structure of the type 1 inositol 1,4,5-trisphosphate receptor at 24 A resolution. The EMBO journal 21, 3575-3581 (2002).
38. Dellis, O. et al. $Ca^{2+}$ entry through plasma membrane IP3 receptors. Science 313, 229-233 (2006).
39. Koziel, K. et al. Plasma membrane associated membranes (PAM) from Jurkat cells contain STIM1 protein is PAM involved in the capacitative calcium entry? The international journal of biochemistry & cell biology 41, 2440-2449 (2009).
40. Paillard, M. et al. Depressing mitochondria-reticulum interactions protects cardiomyocytes from lethal hypoxia-reoxygenation injury. Circulation 128, 1555-1565 (2013).
41. Lemmon, M. A. Pleckstrin homology (PH) domains and phosphoinositides. Biochemical Society symposium, 81-93 (2007).
42. Lemmon, M. A. Pleckstrin homology domains: not just for phosphoinositides. Biochemical Society transactions 32, 707-711 (2004).
43. Scheffzek, K. & Welti, S. Pleckstrin homology (PH) like domains—versatile modules in protein-protein interaction platforms. FEBS letters 586, 2662-2673 (2012).
44. Zhou, Y. et al. Prediction of EF-hand calcium-binding proteins and analysis of bacterial EF-hand proteins. Proteins 65, 643-655 (2006).

45. Sienaert, I. et al. Molecular and functional evidence for multiple $Ca^{2+}$-binding domains in the type 1 inositol 1,4,5-trisphosphate receptor. J Biol Chem 272, 25899-25906 (1997).
46. Joseph, S. K., Brownell, S. & Khan, M. T. Calcium regulation of inositol 1,4,5-trisphosphate receptors. Cell calcium 38, 539-546 (2005).
47. Joseph, N., Reicher, B. & Barda-Saad, M. The calcium feedback loop and T cell activation: How cytoskeleton networks control intracellular calcium flux. Biochimica et biophysica acta (2013).
48. Sylvain, N. R., Nguyen, K. & Bunnell, S. C. Vav1-mediated scaffolding interactions stabilize SLP-76 microclusters and contribute to antigen-dependent T cell responses. Science signaling 4, ra14 (2011).
49. Li, S. Y. et al. The N-terminal 20-amino acid region of guanine nucleotide exchange factor Vav1 plays a distinguished role in T cell receptor-mediated calcium signaling. J Biol Chem 288, 3777-3785 (2013).
50. Nagaleekar, V. K. et al. IP3 receptor-mediated $Ca^{2+}$ release in naive CD4 T cells dictates their cytokine program. Journal of immunology 181, 8315-8322 (2008).
51. Fanger, C. M., Neben, A. L. & Cahalan, M. D. Differential $Ca^{2+}$ influx, KCa channel activity, and $Ca^{2+}$ clearance distinguish Th1 and Th2 lymphocytes. Journal of immunology 164, 1153-1160 (2000).
52. Masat, L. et al. Association of SWAP-70 with the B cell antigen receptor complex. Proceedings of the National Academy of Sciences of the United States of America 97, 2180-2184 (2000).
53. Gross, B. et al. SWAP-70-deficient mast cells are impaired in development and IgE mediated degranulation. European journal of immunology 32, 1121-1128 (2002).
54. Matsuzaki, H. et al. Tespa1 is a novel inositol 1,4,5-trisphosphate receptor binding protein in T and B lymphocytes. FEBS open bio 2, 255-259 (2012).
55. Wang, D. et al. Tespa1 is involved in late thymocyte development through the regulation of TCR-mediated signaling. Nature immunology 13, 560-568 (2012).
56. Cui, J. et al. Regulation of the type 1 inositol 1,4,5-trisphosphate receptor by phosphorylation at tyrosine 353. J Biol Chem 279, 16311-16316 (2004).
57. Lee, B. et al. Phosphorylation of IP3R1 and the regulation of $[Ca^{2+}]i$ responses at fertilization: a role for the MAP kinase pathway. Development 133, 4355-4365 (2006).
58. Sipma, H. et al. Modulation of inositol 1,4,5-trisphosphate binding to the recombinant ligand-binding site of the type-1 inositol 1,4,5-trisphosphate receptor by $Ca^{2+}$ and calmodulin. J Biol Chem 274, 12157-12162 (1999).
59. Bagnasco, M. et al. T cell activation via the CD2 molecule is associated with protein kinase C translocation from the cytosol to the plasma membrane. European journal of immunology 19, 823-827 (1989).

What is claimed:

1. A method of decreasing, reducing, or inhibiting an immune response, comprising contacting SLAT (SWAP-70-like adaptor of T cells) with a sufficient amount of a peptide, said peptide having a length less than or equal to the sequence of SEQ ID NO:3, wherein the peptide comprises SEQ ID NO:4 and is fused to a cell-penetrating or cell targeting moiety, thereby decreasing, reducing, or inhibiting an immune response.

2. A method of decreasing or inhibiting activation or differentiation of CD4+ T cells, comprising contacting SLAT (SWAP-70-like adaptor of T cells) with a sufficient amount of a peptide, said peptide having a length less than or equal to the sequence of SEQ ID NO:3, wherein the peptide comprises SEQ ID NO:4 and is fused to a cell-penetrating or cell targeting moiety, thereby decreasing or inhibiting activation or differentiation of CD4+ T cells.

3. The method of claim 1 or 2, wherein the peptide decreases, reduces, inhibits, suppresses, or disrupts binding of SLAT to IP3R1.

4. The method of claim 1 or 2, wherein the peptide is fused to a TAT fusion polypeptide or an immunoglobulin sequence.

5. The method of claim 1, wherein the method comprises decreasing, reducing, inhibiting, suppressing or limiting an undesirable or aberrant immune response, disorder or disease, an inflammatory response, disorder or disease, inflammation, or an autoimmune response, disorder or disease, or an adverse symptom of an undesirable or aberrant immune response, disorder or disease, an inflammatory response, disorder or disease, inflammation, or an autoimmune response, disorder or disease.

6. The method of claim 1, wherein the method is performed on a subject.

7. The method of claim 6, wherein the subject has or has had an undesirable or aberrant immune response, disorder or disease, an inflammatory response, disorder or disease, inflammation, or an autoimmune response, disorder or disease or an adverse symptom of an undesirable or aberrant immune response, disorder or disease, an inflammatory response, disorder or disease, inflammation, or an autoimmune response, disorder or disease.

8. The method of claim 6, wherein the subject is in need of treatment for an undesirable or aberrant immune response, disorder or disease, an inflammatory response, disorder or disease, inflammation, or an autoimmune response, disorder or disease or an adverse symptom of an undesirable or aberrant immune response, disorder or disease, an inflammatory response, disorder or disease, inflammation, or an autoimmune response, disorder or disease.

9. The method of claim 6, wherein the subject is at risk of an undesirable or aberrant immune response, disorder or disease, an inflammatory response, disorder or disease, inflammation, or an autoimmune response, disorder or disease or an adverse symptom of an undesirable or aberrant immune response, disorder or disease, an inflammatory response, disorder or disease, inflammation, or an autoimmune response, disorder or disease.

10. The method of claim 7, wherein the undesirable or aberrant immune response, disorder or disease, inflammatory response, disorder or disease, inflammation, or autoimmune response, disorder or disease comprises rheumatoid arthritis, juvenile rheumatoid arthritis, osteoarthritis, psoriatic arthritis, multiple sclerosis (MS), encephalomyelitis, myasthenia gravis, systemic lupus erythematosus (SLE), asthma, allergic asthma, autoimmune thyroiditis, atopic dermatitis, eczematous dermatitis, psoriasis, Sjögren's Syndrome, Crohn's disease, aphthous ulcer, iritis, conjunctivitis, keratoconjunctivitis, ulcerative colitis (UC), inflammatory bowel disease (IBD), cutaneous lupus erythematosus, scleroderma, vaginitis, proctitis, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, interstitial lung fibrosis, Hashimoto's thyroiditis, autoimmune polyglandular syndrome, insulin-dependent diabetes mellitus (IDDM, type I diabetes), insulin-resistant diabetes mellitus (type 2 diabetes), immune-mediated infertility, autoimmune Addison's disease, pemphigus vulgaris, pemphigus foliaceus, dermatitis herpetiformis, autoimmune alopecia, vitiligo, autoimmune hemolytic anemia, autoimmune thrombocytopenic purpura, pernicious anemia, Guillain-Barre syndrome, stiff-man syndrome, acute rheumatic fever, sympathetic ophthalmia, Goodpasture's syndrome, systemic necrotizing vasculitis, antiphospholipid syndrome or an allergy, Behcet's disease, severe combined immunodeficiency (SCID), recombinase activating gene (RAG 1/2) deficiency, adenosine deaminase (ADA) deficiency, interleukin receptor common_chain (_c) deficiency, Janus-associated kinase 3 (JAK3) deficiency and reticular dysgenesis; primary T cell immunodeficiency such as DiGcorge syndrome, Nude syndrome, T cell receptor deficiency, MHC class II deficiency, T AP-2 deficiency (MHC class I deficiency), ZAP70 tyrosine kinase deficiency and purine nucleotide phosphorylase (PNP) deficiency, antibody deficiencies, X-linked agammaglobulinemia (Bruton's tyrosine kinase deficiency), autosomal recessive agammaglobulinemia, Mu heavy chain deficiency, surrogate light chain (_5/14 0.1) deficiency, Hyper-lgM syndrome: X-linked (CD40 ligand deficiency) ornon-X-Iinked, Ig heavy chain gene deletion, IgA deficiency, deficiency of IgG subclasses (with or without IgA deficiency), common variable immunodeficiency (CVID), antibody deficiency with normal immunoglobulins; transient hypogammaglobulinemia of infancy, interferon_receptor (IFNGR1, IFNGR2) deficiency, interleukin 12 or interleukin 12 receptor deficiency, immunodeficiency with thymoma, Wiskott-Aldrich syndrome (WAS protein deficiency), ataxia telangiectasia (ATM deficiency), X-linked lymphoproliferative syndrome (SH2D1A/SAP deficiency), hyper IgE syndrome or Graft vs. Host Disease (GVHD).

11. The method of claim 7, wherein the immune response or inflammatory response is an anti-cancer or anti-pathogen immune response or inflammatory response.

* * * * *